(12) United States Patent
Kauffmann-Hefner et al.

(10) Patent No.: US 7,291,642 B2
(45) Date of Patent: Nov. 6, 2007

(54) BRADYKININ-B1 ANTAGONISTS, PROCESS FOR THEIR PREPARATION AND THEIR USE AS MEDICAMENTS

(75) Inventors: Iris Kauffmann-Hefner, Attenweiler (DE); Norbert Hauel, Schemmerhofen (DE); Henri Doods, Warthausen (DE); Angelo Ceci, Mittelbiberach (DE); Stefan Peters, Biberach (DE)

(73) Assignee: Boehringer Ingelheim International GmbH, Ingelheim (DE)

( * ) Notice: Subject to any disclaimer, the term of this patent is extended or adjusted under 35 U.S.C. 154(b) by 183 days.

(21) Appl. No.: 11/256,573

(22) Filed: Oct. 21, 2005

(65) Prior Publication Data

US 2006/0100219 A1 May 11, 2006

(30) Foreign Application Priority Data

Nov. 5, 2004 (DE) .................... 10 2004 054 053
Mar. 26, 2005 (DE) .................... 10 2005 013 967

(51) Int. Cl.
*A61K 31/4164* (2006.01)
*A61K 31/4709* (2006.01)
*A61K 31/4439* (2006.01)
*A61K 31/501* (2006.01)
*A61K 31/5513* (2006.01)
*A61K 31/513* (2006.01)
*A61K 31/454* (2006.01)
*C07D 233/04* (2006.01)
*C07D 233/06* (2006.01)

(52) U.S. Cl. .............. 514/401; 548/349.1; 548/334.1; 548/334.5; 548/311.4; 548/315.1; 548/311.1; 548/315.4; 548/312.4; 546/153; 546/272.7; 546/275.1; 546/210; 544/139; 544/370; 544/300; 540/575; 514/218; 514/235.8; 514/254.05; 514/274; 514/312; 514/326; 514/341

(58) Field of Classification Search .............. 514/401; 548/349.1
See application file for complete search history.

(56) References Cited

U.S. PATENT DOCUMENTS 7,056,937 B2 * 6/2006 Grant et al. ................ 514/353
7,105,172 B1 * 9/2006 Bolla ........................ 424/400

FOREIGN PATENT DOCUMENTS

WO WO 03/106428 A1 12/2003
WO WO 2004/054584 A1 7/2004
WO WO 2004/083173 A2 9/2004
WO WO 2007003411 A2 * 1/2007

OTHER PUBLICATIONS

Conley et al. European Journal of Pharmacology 2005, 527, 44-51.*
Su, Dai-Shi et al; Discovery of a potent, non-peptide bradykinin B1 receptor antagonist; Journal of the American Chemical Society; vol. 125 No. 25, pp. 7516-7517 (2003); American Chemical Society; XP002375613.

* cited by examiner

*Primary Examiner*—Rebecca Anderson
*Assistant Examiner*—Jason M Nolan
(74) *Attorney, Agent, or Firm*—Michael P. Morris; Mary-Ellen M. Devlin; Alan R. Stempel

(57) ABSTRACT

The present invention provides bradykinin-B1 antagonists of the formula

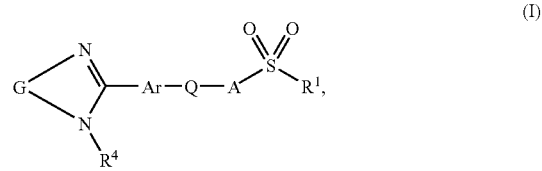

(I)

in which A, Ar, G, Q, $R^1$ and $R^4$ are as defined in claim 1, their enantiomers, their diastereomers, their mixtures and their salts, in particular their physiologically acceptable salts with organic or inorganic acids or bases having useful properties, their preparation, medicaments comprising the pharmacologically effective compounds, their preparation and their use.

8 Claims, No Drawings

BRADYKININ-B1 ANTAGONISTS, PROCESS FOR THEIR PREPARATION AND THEIR USE AS MEDICAMENTS

The present invention provides bradykinin-B1 antagonists of the formula

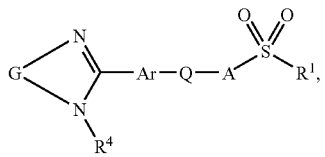
(I)

in which A, Ar, G, Q, $R^1$ and $R^4$ are as defined below, their enantiomers, their diastereomers, their mixtures and their salts, in particular their physiologically acceptable salts with organic or inorganic acids or bases having useful properties, their preparation, medicaments comprising the pharmacologically effective compounds, their preparation and their use.

In the formula (I) above, in a first embodiment, $R^1$ is a phenyl, naphthyl or heteroaryl group, a phenyl-$C_{1-3}$-alkyl or $C_{3-7}$-cycloalkyl group, $R^4$ is a hydrogen atom or a $C_{1-6}$-alkyl group, G is the group —$(CH_2)_m$—, in which m is the number 2 or 3 and in which one to three hydrogen atoms independently of one another may be replaced by $C_{1-3}$-alkyl groups, Ar is a phenylene or heteroarylene group, Q is the group —$(CH_2)_p$—, in which p is the number 2 or 3 and in which one to three hydrogen atoms independently of one another may be replaced by $C_{1-3}$-alkyl groups, A is a group, attached via a nitrogen atom to the sulphonyl group in formula (I), of the formulae (IIa) to (IIi)

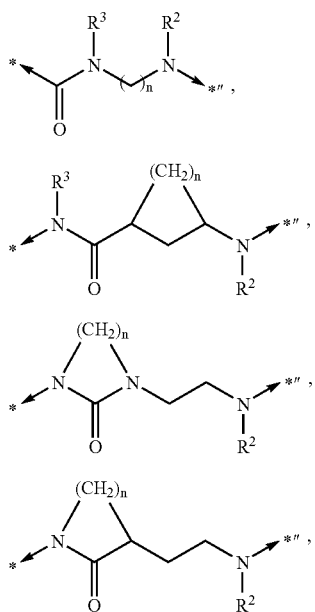

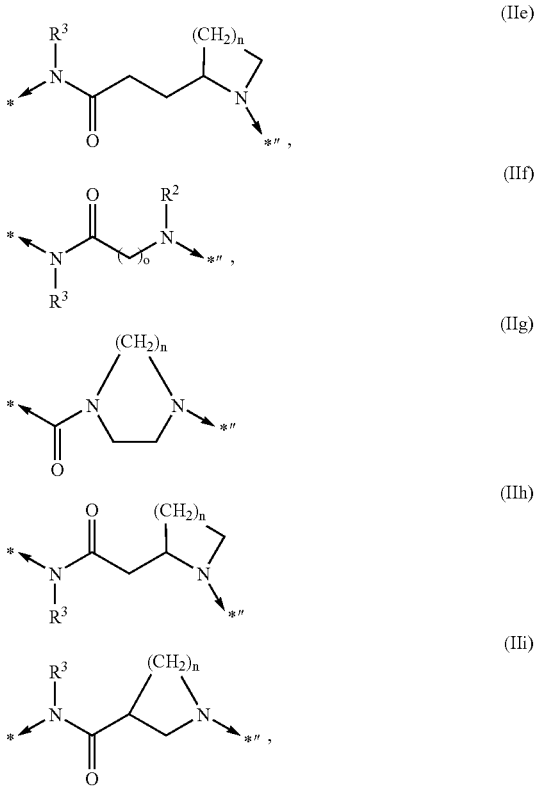

where the groups (IIa) to (IIi) are preferably attached to the sulphonyl group in formula (I) via the position marked *", n is the number 2 or 3, o is the number 1, 2 or 3, $R^2$ is a hydrogen atom, a $C_{1-6}$-alkyl, $C_{2-5}$-alkenyl-methyl, $C_{2-5}$-alkynyl-methyl, $C_{3-7}$-cycloalkyl or a phenyl group and $R^3$ is a hydrogen atom, a phenyl, $C_{1-6}$-alkyl, $C_{2-5}$-alkenyl-methyl, $C_{2-5}$-alkynyl-methyl or $C_{3-7}$-cycloalkyl group or a group —$CH_2$—$CF_3$, —$CH_2$—$CHF_2$ or —$CH_2$—$CH_2F$, where the phenyl and phenylene groups present in the definitions mentioned above may be mono-, di-, tri- or tetrasubstituted by fluorine, chlorine, bromine or iodine atoms, by $C_{1-5}$-alkyl, trifluoromethyl, amino, $C_{1-3}$-alkylamino, di-($C_{1-3}$-alkyl)-amino, di-($C_{1-3}$-alkyl)-amino-carbonylamino, nitro, cyano, $C_{1-3}$-alkylcarbonyl, $C_{1-3}$-alkylsulphonyl, aminocarbonyl, $C_{1-3}$-alkylaminocarbonyl, di-($C_{1-3}$-alkyl)-aminocarbonyl, aminosulphonyl, $C_{1-3}$-alkylaminosulphonyl, di-($C_{1-3}$-alkyl)-aminosulphonyl, $C_{1-3}$-alkylcarbonylamino, carboxy-$C_{1-3}$-alkyl, $C_{1-3}$-alkyloxycarbonyl-$C_{1-3}$-alkyl, phenyl, phenyloxy, hydroxyl, $C_{1-4}$-alkyloxy, monofluoromethyloxy, difluoromethyloxy or trifluoromethyloxy groups or by N-pyrrolidinocarbonyl, N-pyrrolidinosulphonyl, N-piperidinocarbonyl or N-piperidinosulphonyl, where the methylene group present in the piperidine rings mentioned above may be replaced in the 4-position by O, S, SO, $SO_2$, NH or N($C_{1-3}$-alkyl), and the substituents may be identical or different, except for substitution by two, three or four nitro groups, where the naphthyl groups present in the definitions mentioned above may be mono- or disubstituted by fluorine, chlorine, bromine or iodine atoms, by $C_{1-3}$-alkyl, amino or di-($C_{1-3}$-alkyl)-amino groups and the substituents may be identical or different, where, unless indicated otherwise, the term "heteroaryl group" mentioned above in the definitions is to be understood as meaning a monocyclic 5- or 6-membered or a bicyclic 9- or 10-membered heterocyclic aromatic ring system, which, in addition to at least one carbon atom, contains one or more heteroatoms selected from N, O and/or S, for example a monocyclic 5-membered heteroaryl group attached via a carbon or nitrogen atom which contains an imino group which is optionally substituted by a $C_{1-3}$-alkyl, phenyl or phenyl-$C_{1-3}$-alkyl group, an oxygen or sulphur atom or an imino group which is optionally substituted by a $C_{1-3}$-alkyl, phenyl, amino-$C_{2-3}$-alkyl, $C_{1-3}$-alkylamino-$C_{2-3}$-alkyl or di-($C_{1-3}$-alkyl)-amino-$C_{2-3}$-alkyl group, by a 4- to 7-membered cycloalkyleneimino-$C_{1-3}$-alkyl or phenyl-$C_{1-3}$-alkyl group or an oxygen atom or sulphur atom and additionally a nitrogen atom or an imino group which is optionally substituted by a $C_{1-3}$-alkyl or phenyl-$C_{1-3}$-alkyl group and two or three nitrogen atoms, or a monocyclic 6-membered heteroaryl group which contains one, two or three nitrogen atoms, or a bicyclic 9-membered heteroaryl group consisting of one of the 5-membered heteroaryl groups mentioned above which is fused to one of the 6-membered heteroaryl groups mentioned above via two adjacent carbon atoms or a carbon and an adjacent nitrogen atom forming a bicycle, where the 5-membered heteroaryl group may also be replaced by a cyclopentadienyl group or the 6-membered heteroaryl group may also be replaced by a phenyl ring, or a bicyclic 10-membered heteroaryl group which consists of a phenyl ring and one of the 6-membered heteroaryl groups mentioned above or of two of the 6-membered heteroaryl groups mentioned above which are in each case condensed via two adjacent carbon atoms forming a bicycle, where the mono- and bicyclic heteroaryl groups mentioned above may additionally be mono-, di- or trisubstituted in the carbon skeleton by fluorine, chlorine, bromine or iodine atoms or by $C_{1-3}$-alkyl groups and where the substituents may be identical or different, and the term "heteroarylene group" mentioned above in the definitions is to be understood as meaning the mono- or bicyclic heteroaryl groups mentioned above which, however, are attached to the adjacent groups via two carbon atoms or via one carbon and one nitrogen atom, where the alkyl and alkoxy groups present in the definitions mentioned above which have more than two carbon atoms may, unless indicated otherwise, be straight-chain or branched, and where some or all of the hydrogen atoms of the methyl or ethyl groups present in the definitions mentioned above may be replaced by fluorine atoms, or their tautomers, their enantiomers, their diastereomers, their mixtures and their salts.

Examples of monocyclic heteroaryl groups are the pyridyl, N-oxypyridyl, pyrazolyl, pyridazinyl, pyrimidinyl, pyrazinyl, [1,2,3]triazinyl, [1,3,5]triazinyl, [1,2,4]triazinyl, pyrrolyl, imidazolyl, [1,2,4]triazolyl, [1,2,3]triazolyl, tetrazolyl, furanyl, isoxazolyl, oxazolyl, [1,2,3]oxadiazolyl, [1,2,4]oxadiazolyl, [1,2,5]oxadiazolyl, [1,3,4]oxadiazolyl, thiophenyl, thiazolyl, isothiazolyl or [1,2,4]thiadiazolyl group.

Examples of bicyclic heteroaryl groups are the benzimidazolyl, benzofuranyl, benzo[c]furanyl, benzo[b]thiophenyl, benzo[c]thiophenyl, benzothiazolyl, benzo[c]isothiazolyl, benzo[d]isothiazolyl, benzoxazolyl, benzo[c]isoxazolyl, benzo[d]isoxazolyl, benz[1,2,5]oxadiazolyl, benzo[1,2,5]thiadiazolyl, benzo[1,2,3]thiadiazolyl, benzo[d][1,2,3]triazinyl, benzo[1,2,4]triazinyl, benzotriazolyl, cinnolinyl, quinolinyl, N-oxyquinolinyl, indazolyl, purinyl, naphthyridinyl, pteridinyl, isoquinolinyl, quinazolinyl, N-oxyquinazolinyl, quinoxalinyl, phthalazinyl, indolyl, isoindolyl or benz[1,2,3]oxadiazolyl group.

Examples of the $C_{1-6}$-alkyl groups mentioned above in the definitions are the methyl, ethyl, 1-propyl, 2-propyl, n-butyl, sec-butyl, tert.-butyl, 1-pentyl, 2-pentyl, 3-pentyl, neo-pentyl, 1-hexyl, 2-hexyl or 3-hexyl group.

A second embodiment of the present invention consists in the compounds of the above formula (I) in which $R^1$ is a phenyl, naphthyl or heteroaryl group, a phenyl-$C_{1-3}$-alkyl or $C_{3-6}$-cycloalkyl group, $R^4$ is a hydrogen atom or a $C_{1-4}$-alkyl group, G is the group —$(CH_2)_m$—, in which m is the number 2 or 3 and in which one to three hydrogen atoms independently of one another may be replaced by $C_{1-3}$-alkyl groups, for example methyl groups, Ar is a phenylene group or a monocyclic 6-membered heteroarylene group or a monocyclic 5-membered heteroarylene group, attached via a carbon or nitrogen atom, Q is the group —$(CH_2)_p$—, in which p is the number 2 or 3 and in which one to three hydrogen atoms independently of one another may be replaced by $C_{1-3}$-alkyl groups, for example methyl groups, A is a group of the formula (IIa), (IIb), (IIc), (IId), (IIe), (IIf), (IIg), (IIh) or (IIi) attached via a nitrogen atom to the sulphonyl group in formula (I), where the groups (IIa) to (IIi) are preferably attached to the sulphonyl group in formula (I) via the position marked *" and n is the number 2 or 3, o is the number 1, 2 or 3, $R^2$ is a hydrogen atom, a $C_{1-4}$-alkyl, $C_{2-5}$-alkenyl-methyl, $C_{3-6}$-cycloalkyl or a phenyl group and $R^3$ is a hydrogen atom, a $C_{1-4}$-alkyl, $C_{2-5}$-alkenyl-methyl or $C_{3-6}$-cycloalkyl group or a $C_{1-3}$-alkyl group in which each methyl group may be substituted by up to three and each methylene group by up to two fluorine atoms, where the phenyl and phenylene groups present in the definitions mentioned above may be mono-, di-, tri- or tetrasubstituted by fluorine, chlorine or bromine atoms, by $C_{1-5}$-alkyl, trifluoromethyl, amino, $C_{1-3}$-alkylamino, di-($C_{1-3}$-alkyl)-amino, di-($C_{1-3}$-alkyl)-amino-carbonylamino, nitro, cyano, $C_{1-3}$-alkylcarbonyl, $C_{1-3}$-alkylsulphonyl, aminocarbonyl, $C_{1-3}$-alkylaminocarbonyl, di-($C_{1-3}$-alkyl)-aminocarbonyl, aminosulphonyl, $C_{1-3}$-alkylaminosulphonyl, di-($C_{1-3}$-alkyl)-aminosulphonyl, $C_{1-3}$-alkylcarbonylamino, phenyl, phenyloxy, hydroxyl, $C_{1-4}$-alkyloxy, monofluoromethyloxy, difluoromethyloxy or trifluoromethyloxy groups or by N-pyrrolidinocarbonyl, N-pyrrolidinosulphonyl, N-piperidinocarbonyl or N-piperidinosulphonyl, where the methylene group present in the piperidine rings mentioned above may be replaced in the 4-position by O, S, SO, $SO_2$, NH or N($C_{1-3}$-alkyl), and the substituents may be identical or different, except for substitution by two, three or four nitro groups, where the naphthyl groups present in the definitions mentioned above may be mono- or disubstituted by fluorine, chlorine or bromine atoms, by $C_{1-3}$-alkyl, amino or di-($C_{1-3}$-alkyl)-amino groups and the substituents may be identical or different, where, unless indicated otherwise, a "heteroaryl group" is to be understood as meaning a monocyclic 5- or 6-membered or a bicyclic 9- or 10-membered heterocyclic aromatic ring system, for example a monocyclic 5-membered heteroaryl group attached via a carbon or nitrogen atom which contains an imino group which is optionally substituted by a $C_{1-3}$-alkyl, phenyl or phenyl-$C_{1-3}$-alkyl group, an oxygen or sulphur atom or an imino group which is optionally substituted by a $C_{1-3}$-alkyl or phenyl group, by a 5- to 7-membered cycloalkyleneimino-$C_{1-3}$-alkyl or phenyl-$C_{1-3}$-alkyl group or an oxygen atom or sulphur atom and additionally a nitrogen atom or an imino group which is optionally substituted by a $C_{1-3}$-alkyl or phenyl-$C_{1-3}$-alkyl group and additionally two nitrogen atoms, or a monocyclic 6-membered heteroaryl group which contains one or two nitrogen atoms, or a bicyclic 9-membered heteroaryl group consisting of one of the 5-membered heteroaryl groups mentioned above which is fused to one of the 6-membered heteroaryl groups mentioned above via two adjacent carbon atoms or a carbon and an adjacent nitrogen atom forming a bicycle, where the 5-membered heteroaryl group may also be replaced by a cyclopentadienyl group or the 6-membered heteroaryl group may also be replaced by a phenyl ring, or a bicyclic 10-membered heteroaryl group which consists of a phenyl ring and one of the 6-membered heteroaryl groups mentioned above or of two of the 6-membered heteroaryl groups mentioned above which are in each case condensed via two adjacent carbon atoms forming a bicycle, where the mono- and bicyclic heteroaryl groups mentioned above may additionally be mono-, di- or trisubstituted in the carbon skeleton by fluorine, chlorine or bromine atoms or by $C_{1-3}$-alkyl groups and where the substituents may be identical or different, and the term "heteroarylene group" mentioned above in the definitions is to be understood as meaning the mono- or bicyclic heteroaryl groups mentioned above which, however, are attached to the adjacent groups via two carbon atoms or via one carbon and one nitrogen atom, where the alkyl and alkoxy groups present in the definitions mentioned above which have more than two carbon atoms may, unless indicated otherwise, be straight-chain or branched, and where some or all of the hydrogen atoms of the methyl or ethyl groups present in the definitions mentioned above may be replaced by fluorine atoms, or their tautomers, their enantiomers, their diastereomers, their mixtures and their salts.

A third embodiment of the present invention consists in the compounds of the above formula (I) in which $R^1$ is a phenyl or phenylmethyl group which is optionally mono-, di- or trisubstituted by fluorine, chlorine or bromine atoms, nitro, cyano, $C_{1-3}$-alkylsulphonyl, $C_{1-5}$-alkyl, trifluoromethyl, hydroxyl, $C_{1-5}$-alkyloxy, trifluoromethoxy, phenyloxy, morpholin-4-ylsulphonyl, phenyl, dimethylaminocarbonylamino, amino, methylcarbonylamino, dimethylamino, carboxy-$C_{1-3}$-alkyl or $C_{1-3}$-alkyloxycarbonyl-$C_{1-3}$-alkyl groups, where the substituents may be identical or different and polysubstitution by two or three nitro groups is excluded, a phenyl group which is optionally tetrasubstituted by fluorine, chlorine or bromine atoms, cyano, $C_{1-3}$-alkyl, trifluoromethyl, $C_{1-3}$-alkyloxy or trifluoromethoxy groups, where the substituents may be identical or different, a benzo[b]thiophenyl, quinolinyl, naphthyl, benz[1,2,5]oxadiazolyl, furanyl, thiophenyl, imidazolyl, thiazolyl, pyrazolyl, pyridinyl or isoxazolyl group which is optionally mono-, di- or trisubstituted by chlorine or bromine atoms or methyl, amino, methylamino or dimethylamino groups or a $C_{3-6}$-cycloalkyl group, for example the cyclopropyl group, $R^4$ is a hydrogen atom or a methyl group, G is the group —$(CH_2)_m$— in which m is the number 2 or 3 or the group —$(CH_2)_m$— in which m is the number 2 or 3 and in which one, two or three hydrogen atoms independently of one another are replaced by methyl or ethyl groups, Ar is a phenylene group, Q is the group —$(CH_2)_p$— in which p is the number 2 or the group —$(CH_2)_p$— in which p is the number 2 and in which one or two hydrogen atoms independently of one another are replaced by methyl or ethyl groups, A is a group of the formula (IIa), (IIb), (IIc), (IId), (IIe), (IIf), (IIg), (IIh) or (IIi) attached to the sulphonyl group in formula (I) via the position marked *", in which n is the number 2 or 3, o is the number 1, 2 or 3, $R^2$ is a hydrogen atom, a $C_{1-3}$-alkyl, cyclopropyl or a phenyl group and $R^3$ is a hydrogen atom, a cyclopropyl group, a straight-chain or branched $C_{1-3}$-alkyl group, a $F_3C—CH_2—$, $F_2CH—CH_2—$ or $H_2FC—CH_2—$ group, their tautomers, their enantiomers, their diastereomers, their mixtures and their salts.

A fourth embodiment of the present invention consists in the compounds of the above formula (I) in which $R^1$ is an isopropyl, cyclopropyl, phenyl, phenylmethyl, 2,4-dichlorophenylmethyl, 2-chlorophenyl, 3-chlorophenyl, 4-chlorophenyl, 2-bromophenyl, 3-bromophenyl, 4-bromophenyl, 3-fluorophenyl, 4-fluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4,5-trichlorophenyl, 3,4-difluorophenyl, 2-chloro-4-fluorophenyl, 2-chloro-4-cyanophenyl, 5-fluoro-2-methylphenyl, 2-chloro-6-methylphenyl, 2-chloro-4-trifluoromethylphenyl, 3-chloro-2-methylphenyl, 4-amino-3,5-dichlorophenyl, 4-amino-2,5-dichlorophenyl, 4-chloro-2,5-dimethylphenyl, 2,4-dichloro-5-methylphenyl, 3,5-dichloro-4-hydroxyphenyl, 4-(morpholin-4-ylsulphonyl)phenyl, 4-chloro-3-nitrophenyl, 3-methylsulphonylphenyl, 4-methylsulphonylphenyl, 4-cyanophenyl, 2-nitrophenyl, 3-nitrophenyl, 4-nitrophenyl, 4-nitro-3-fluorophenyl, 4-nitro-3-trifluoromethylphenyl, 4-methoxy-2-nitrophenyl, 2-trifluoromethoxyphenyl, 2-methylphenyl, 3-methylphenyl, 4-methylphenyl, 2-trifluoromethylphenyl, 3-trifluoromethylphenyl, 4-trifluoromethylphenyl, 4-propylphenyl, 4-isopropylphenyl, 4-tert.-butylphenyl, 4-pentylphenyl, 4-(3-methoxycarbonylpropyl)phenyl, 2,4,6-trimethylphenyl, 2,5-dimethylphenyl, 3,5-dimethylphenyl, 2,3,5,6-tetramethylphenyl, 4-methoxy-2,3,6-trimethylphenyl, 4-butoxyphenyl, 4-methoxyphenyl, 4-trifluoromethoxyphenyl, 2,5-dimethoxyphenyl, 3,4-dimethoxyphenyl, 4-chloro-2-methoxyphenyl, 5-chloro-2-methoxyphenyl, 4-acetylaminophenyl, 4-acetylamino-3-chlorophenyl, 4-(3,3-dimethylureido)phenyl, 4-phenoxyphenyl, benzyl, 2-chlorobenzyl, 2,4-dichlorobenzyl, biphen-4-yl, benzo[b]thiophen-2-yl, benzo[b]thiophen-3-yl, quinolin-8-yl, isoquinolin-1-yl, isoquinolin-3-yl, naphthalen-1-yl, naphthalen-2-yl, 4-chloronaphthalen-1-yl, 5-chloronaphthalen-1-yl, 5-dimethylaminonaphthalen-1-yl, benz[1,2,5]oxadiazol-4-yl, furan-2-yl, furan-3-yl, thiophen-2-yl, thiophen-3-yl, 4,5-dichlorothiophen-2-yl, 5-chlorothiophen-2-yl, 1,2-dimethyl-1H-imidazol-4-yl, 2-methyl-1H-imidazol-4-yl, 4-bromo-5-chlorothiophen-2-yl, 3-bromo-5-chlorothiophen-2-yl, 2,4-dimethylthiazol-5-yl, 5-chloro-1,3-dimethyl-1H-pyrazol-4-yl, pyridin-2-yl, pyridin-3-yl, pyridin-4-yl, 3,5-dimethylisoxazol-4-yl or 1-methyl-1H-imidazol-4-yl group, $R^4$ is a hydrogen atom or a methyl group, G is the group —$(CH_2)_m$— in which m is the number 2 or 3 or the group —$(CH_2)_m$— in which m is the number 2 or 3 and in which one or two hydrogen atoms independently of one another are replaced by methyl groups, Ar is a phenylene group which is optionally mono- or disubstituted independently of one another by fluorine, chlorine or bromine atoms, cyano, $C_{1-3}$-alkyl, trifluoromethyl, $C_{1-3}$-alkyloxy or trifluoromethoxy groups, but which is preferably unsubstituted, Q is the group —$(CH_2)_p$— in which p is the number 2 or the group —$(CH_2)_p$— in which p is the number 2 and in which one or two hydrogen atoms independently of one another are replaced by methyl groups, A is a group of the formula (IIa), (IIb), (IIc), (IId), (IIe), (IIf), (IIg), (IIh) or (IIi) attached to the sulphonyl group in formula (I) via the position marked *", and is preferably a group of the formula (IIa), (IIb), (IIc), (IIe), (IIf), (IIg), (IIh) or (IIi), in which n is the number 2 or 3, o is the number 1, 2 or 3, $R^2$ is a hydrogen atom, a methyl, ethyl, n-propyl, i-propyl, cyclopropyl or phenyl group and $R^3$ is a hydrogen atom, a methyl, ethyl, n-propyl, i-propyl, 2-monofluoroethyl, 2,2-difluoroethyl, 2,2,2-trifluoroethyl or cyclopropyl group, where the phenyl groups mentioned above or the phenyl groups present in the groups mentioned above independently of one another may, unless indicated otherwise, be mono- or disubstituted by fluorine, chlorine or bromine atoms, cyano, $C_{1-3}$-alkyl, trifluoromethyl, $C_{1-3}$-alkyloxy or trifluoromethoxy groups, but are preferably unsubstituted, their tautomers, their enantiomers, their diastereomers, their mixtures and their salts.

Very particularly preferred compounds of the above formula (I) which may be mentioned are, for example, the following:

(1) 3-[(2,3-Dichlorobenzenesulphonyl)methylamino]-N-{2-[4-(4,5-dihydro-1H-imidazol-2-yl)phenyl]ethyl}-N-methylpropionamide, (2) 4-[(2,3-Dichlorobenzenesulphonyl)methylamino]-N-{2-[4-(4,5-dihydro-1H-imidazol-2-yl)phenyl]ethyl}-N-methylbutyramide, (3) 4-[(2,3-Dichlorobenzenesulphonyl)phenylamino]-N-{2-[4-(4,5-dihydro-1H-imidazol-2-yl)phenyl]ethyl}-N-methylbutyramide, (4) 4-[(2,3-Dichlorobenzenesulphonyl)isopropylamino]-N-{2-[4-(4,5-dihydro-1H-imidazol-2-yl)phenyl]ethyl}-N-methylbutyramide, (5) 4-[(2,3-Dichlorobenzenesulphonyl)cyclopropylamino]-N-{2-[4-(4,5-dihydro-1H-imidazol-2-yl)phenyl]ethyl}-N-methylbutyramide, (6) 2-(Benzenesulphonylmethylamino)-N-{2-[4-(4,5-dihydro-1H-imidazol-2-yl)phenyl]ethyl}-N-methylacetamide, (7) 3-(Benzenesulphonylmethylamino)-N-{2-[4-(4,5-dihydro-1H-imidazol-2-yl)phenyl]ethyl}-N-methylpropionamide, (8) 3-[1-(2,3-Dichlorobenzenesulphonyl)piperidin-2-yl]-N-{2-[4-(4,5-dihydro-1H-imidazol-2-yl)phenyl]ethyl}-N-methylpropionamide, (9) 3-[1-(4-Chloro-2,5-dimethylbenzenesulphonyl)piperidin-2-yl]-N-{2-[4-(4,5-dihydro-1H-imidazol-2-yl)phenyl]ethyl}-N-methylpropionamide,

(10) 3-(1-Benzenesulphonylpiperidin-2-yl)-N-{2-[4-(4,5-dihydro-1H-imidazol-2-yl)phenyl]ethyl}-N-methylpropionamide,

(11) 3-[1-(2,3-Dichlorobenzenesulphonyl)pyrrolidin-2(S)-yl]-N-{2-[4-(4,5-dihydro-1H-imidazol-2-yl)phenyl]ethyl}-N-methylpropionamide,

(12) 1-(2,3-Dichlorobenzenesulphonyl)piperidin-3-yl-N-{2-[4-(4,5-dihydro-1H-imidazol-2-yl)phenyl]ethyl}-N-methylcarboxamide,

(13) N-{3-[(2,3-Dichlorobenzenesulphonyl)methylamino]propyl}-3-[4-(4,5-dihydro-1H-imidazol-2-yl)phenyl]propionamide,

(14) N-{3-[(2,3-Dichlorobenzenesulphonyl)methylamino]propyl}-3-[4-(4,5-dihydro-1H-imidazol-2-yl)phenyl]-N-methylpropionamide,

(15) 3-[4-(4,5-Dihydro-1H-imidazol-2-yl)phenyl]-N-methyl-N-{3-[phenyl(toluene-4-sulphonyl)amino]propyl}propionamide,

(16) N-{2-[(4-Chloro-2,5-dimethylbenzenesulphonyl)methylamino]ethyl}-3-[4-(4,5-dihydro-1H-imidazol-2-yl)phenyl]propionamide,

(17) 2,3-Dichloro-N-[2-(3-{2-[4-(4,5-dihydro-1H-imidazol-2-yl)phenyl]ethyl}-2-oxoimidazolidin-1-yl)ethyl]-N-methylbenzenesulphonamide,

(18) 2,3-Dichloro-N-[2-(3-{2-[4-(4,5-dihydro-1H-imidazol-2-yl)phenyl]ethyl}-2-oxotetrahydropyrimidin-1-yl)ethyl]-N-methylbenzenesulphonamide,

(19) 4-[(2,3-Dichlorobenzenesulphonyl)methylamino]-N-methyl-N-{2-[4-(1-methyl-4,5-dihydro-1H-imidazol-2-yl)phenyl]ethyl}butyramide,

(20) 3-[(2,3-Dichlorobenzenesulphonyl)methylamino]cyclohexane-N-{2-[4-(4,5-dihydro-1H-imidazol-2-yl)phenyl]ethyl}-N-methyl-carboxamide,

(21) 3-[(2,3-Dichlorobenzenesulphonyl)methylamino]cyclopentane-N-{2-[4-(4,5-dihydro-1H-imidazol-2-yl)phenyl]ethyl}-N-methylcarboxamide,

(22) 4-[(2,3-Dichlorobenzenesulphonyl)methylamino]-N-{2-[4-(4,5-dihydro-1H-imidazol-2-yl)phenyl]ethyl}-N-ethylbutyramide,

(23) N-Cyclopropyl-4-[(2,3-dichlorobenzenesulphonyl)methylamino]-N-{2-[4-(4,5dihydro-1H-imidazol-2-yl)phenyl]ethyl}butyramide,

(24) 4-[(2,3-Dichlorobenzenesulphonyl)methylamino]-N-{2-[4-(4,5-dihydro-1H-imidazol-2-yl)phenyl]ethyl}butyramide,

(25) 3-[(2,5-Dichlorobenzenesulphonyl)methylamino]-N-{2-[4-(4,5-dihydro-1H-imidazol-2-yl)phenyl]ethyl}-N-methylpropionamide,

(26) 3-[(Benzo[b]thiophene-2-sulphonyl)methylamino]-N-{2-[4-(4,5-dihydro-1H-imidazol-2-yl)phenyl]ethyl}-N-methylpropionamide,

(27) 3-[(2-Chlorobenzenesulphonyl)methylamino]-N-{2-[4-(4,5-dihydro-1H-imidazol-2-yl)phenyl]ethyl}-N-methylpropionamide,
(28) 2-[1-(2,3-Dichlorobenzenesulphonyl)pyrrolidin-2-yl]-N-{2-[4-(4,5-dihydro-1H-imidazol-2-yl)phenyl]ethyl}-N-methylacetamide,
(29) N-{2-[4-(4,5-Dihydro-1H-imidazol-2-yl)phenyl]ethyl}-N-methyl-3-[methyl-(2,4,6-trimethylbenzenesulphonyl)amino]propionamide,
(30) 3-[(2-Chloro-6-methylbenzenesulphonyl)methylamino]-N-{2-[4-(4,5-dihydro-1H-imidazol-2-yl)phenyl]ethyl}-N-methylpropionamide,
(31) N-{2-[4-(4,5-Dihydro-1H-imidazol-2-yl)phenyl]ethyl}-N-methyl-3-[methyl(quinoline-8-sulphonyl)amino]propionamide,
(32) 3-[4-(4,5-Dihydro-1H-imidazol-2-yl)phenyl]-N-methyl-N-{2-[methyl-(2,4,6-trimethylbenzenesulphonyl)amino]ethyl}propionamide,
(33) N-{2-[4-(4,5-Dihydro-1H-imidazol-2-yl)phenyl]ethyl}-3-[(4-trifluoro-methoxybenzenesulphonyl)methylamino]-N-methylpropionamide,
(34) N-{2-[(4-Chloro-2,5-dimethylbenzenesulphonyl)methylamino]ethyl}-3-[4-(4,5-dihydro-1H-imidazol-2-yl)phenyl]-N-methylpropionamide,
(35) 3-[(5-Chloro-2-methoxybenzenesulphonyl)methylamino]-N-{2-[4-(4,5-dihydro-1H-imidazol-2-yl)phenyl]ethyl}-N-methylpropionamide,
(36) N-{2-[(2,3-Dichlorobenzenesulphonyl)methylamino]ethyl}-3-[4-(4,5-dihydro-1H-imidazol-2-yl)phenyl]-N-methylpropionamide,
(37) 3-(Cyclopropanesulphonylmethylamino)-N-{2-[4-(4,5-dihydro-1H-imidazol-2-yl)phenyl]ethyl}-N-methylpropionamide,
(38) 1-[4-(2,3-Dichlorobenzenesulphonyl)-[1,4]diazepan-1-yl]-3-[4-(4,5-dihydro-1H-imidazol-2-yl)phenyl]propan-1-one,
(39) 1-[4-(2,3-Dichlorobenzenesulphonyl)piperazin-1-yl]-3-[4-(4,5-dihydro-1H-imidazol-2-yl)phenyl]propan-1-one,
(40) 2-[(2,3-Dichlorobenzenesulphonyl)methylamino]-N-{2-[4-(4,5-dihydro-1H-imidazol-2-yl)phenyl]ethyl}-N-methylacetamide,
(41) 3-[(3,5-Dichlorobenzenesulphonyl)methylamino]-N-[2-[4-(4,5-dihydro-1H-imidazol-2-yl)phenyl]ethyl}-N-methylpropionamide,
(42) 3-(Benzenesulphonylmethylamino)-N-{2-[4-(4,5-dihydro-1H-imidazol-2-yl)phenyl]ethyl}-N-methylpropionamide,
(43) N-{2-[4-(4,5-Dihydro-1H-imidazol-2-yl)phenyl]ethyl}-N-methyl-3-[methyl-(4-propylbenzenesulphonyl)amino]propionamide,
(44) 3-[(4-Chloro-3-nitrobenzenesulphonyl)methylamino]-N-{2-[4-(4,5-dihydro-1H-imidazol-2-yl)phenyl]ethyl}-N-methylpropionamide,
(45) 3-[(2-Chloro-6-methylbenzenesulphonyl)methylamino]-N-{2-[4-(4,5-dihydro-1H-imidazol-2-yl)phenyl]ethyl}-N-methylpropionamide,
(46) N-{2-[4-(4,5-Dihydro-1H-imidazol-2-yl)phenyl]ethyl}-3-[(4-isopropyl-benzenesulphonyl)methylamino]-N-methylpropionamide,
(47) 3-[(5-Chloronaphthalene-1-sulphonyl)methylamino]-N-{2-[4-(4,5-dihydro-1H-imidazol-2-yl)phenyl]ethyl}-N-methylpropionamide,
(48) N-{2-[4-(4,5-Dihydro-1H-imidazol-2-yl)phenyl]ethyl}-N-methyl-3-[methyl(toluene-4-sulphonyl)amino]propionamide,
(49) 3-[(2-Bromobenzenesulphonyl)methylamino]-N-{2-[4-(4,5-dihydro-1H-imidazol-2-yl)phenyl]ethyl}-N-methylpropionamide,
(50) 3-[(2,4-Dichloro-5-methylbenzenesulphonyl)methylamino]-N-{2-[4-(4,5-dihydro-1H-imidazol-2-yl)phenyl]ethyl}-N-methylpropionamide,
(51) N-{2-[4-(4,5-Dihydro-1H-imidazol-2-yl)phenyl]ethyl}-N-methyl-3-{methyl-[4-(morpholine-4-sulphonyl)benzenesulphonyl]amino}propionamide,
(52) N-{2-[4-(4,5-Dihydro-1H-imidazol-2-yl)phenyl]ethyl}-N-methyl-3-[methyl-(3-nitrobenzenesulphonyl)amino]propionamide,
(53) N-{2-[4-(4,5-Dihydro-1H-imidazol-2-yl)phenyl]ethyl}-N-methyl-3-[methyl-(2-trifluoromethoxybenzenesulphonyl)amino]propionamide,
(54) 3-[(Benz[1,2,5]oxadiazole-4-sulphonyl)methylamino]-N-{2-[4-(4,5-dihydro-1H-imidazol-2-yl)phenyl]ethyl}-N-methylpropionamide,
(55) 3-[(2-Chloro-4-trifluoromethylbenzenesulphonyl)methylamino]-N-{2-[4-(4,5-dihydro-1H-imidazol-2-yl)phenyl]ethyl}-N-methylpropionamide,
(56) 3-[(4-Butoxybenzenesulphonyl)methylamino]-N-{2-[4-(4,5-dihydro-1H-imidazol-2-yl)phenyl]ethyl}-N-methylpropionamide,
(57) 3-[(3,4-Difluorobenzenesulphonyl)methylamino]-N-{2-[4-(4,5-dihydro-1H-imidazol-2-yl)phenyl]ethyl}-N-methylpropionamide,
(58) 3-[(3,5-Dichloro-4-hydroxybenzenesulphonyl)methylamino]-N-{2-[4-(4,5-dihydro-1H-imidazol-2-yl)phenyl]ethyl}-N-methylpropionamide,
(59) N-{2-[4-(4,5-Dihydro-1H-imidazol-2-yl)phenyl]ethyl}-N-methyl-3-[methyl(naphthalene-1-sulphonyl)amino]propionamide,
(60) 3-[(2,4-Dichlorobenzenesulphonyl)methylamino]-N-{2-[4-(4,5-dihydro-1H-imidazol-2-yl)phenyl]ethyl}-N-methylpropionamide,
(61) N-{2-[4-(4,5-Dihydro-1H-imidazol-2-yl)phenyl]ethyl}-N-methyl-3-[methyl-(4-pentylbenzenesulphonyl)amino]propionamide,
(62) N-{2-[4-(4,5-Dihydro-1H-imidazol-2-yl)phenyl]ethyl}-3-[(3,5-dimethyl-benzenesulphonyl)methylamino]-N-methylpropionamide,
(63) N-{2-[4-(4,5-Dihydro-1H-imidazol-2-yl)phenyl]ethyl}-N-methyl-3-(methylphenylmethanesulphonylamino)propionamide,
(64) 3-[(2-Chloro-4-fluorobenzenesulphonyl)methylamino]-N-{2-[4-(4,5-dihydro-1H-imidazol-2-yl)phenyl]ethyl}-N-methylpropionamide,
(65) 3-[(2-Chloro-4-cyanobenzenesulphonyl)methylamino]-N-{2-[4-(4,5-dihydro-1H-imidazol-2-yl)phenyl]ethyl}-N-methylpropionamide,
(66) N-{2-[4-(4,5-Dihydro-1H-imidazol-2-yl)phenyl]ethyl}-3-[(3-methane-sulphonylbenzenesulphonyl)methylamino]-N-methylpropionamide,
(67) 3-[(Biphenyl-4-sulphonyl)methylamino]-N-{2-[4-(4,5-dihydro-1H-imidazol-2-yl)phenyl]ethyl}-N-methylpropionamide,
(68) N-{2-[4-(4,5-Dihydro-1H-imidazol-2-yl)phenyl]ethyl}-3-[(5-fluoro-2-methylbenzenesulphonyl)methylamino]-N-methylpropionamide,
(69) N-{2-[4-(4,5-Dihydro-1H-imidazol-2-yl)phenyl]ethyl}-N-methyl-3-[methyl-(4-nitrobenzenesulphonyl)amino]propionamide,
(70) N-{2-[4-(4,5-Dihydro-1H-imidazol-2-yl)phenyl]ethyl}-3-{[4-(3,3-dimethylureido)benzenesulphonyl]methylamino}-N-methylpropionamide,

(71) N-{2-[4-(4,5-Dihydro-1H-imidazol-2-yl)phenyl]ethyl}-N-methyl-3-[methyl-(4-trifluoromethylbenzenesulphonyl)amino]propionamide,
(72) N-{2-[4-(4,5-Dihydro-1H-imidazol-2-yl)phenyl]ethyl}-3-[(furan-2-sulphonyl)methylamino]-N-methylpropionamide,
(73) 3-[(2-Chlorophenylmethanesulphonyl)methylamino]-N-{2-[4-(4,5-dihydro-1H-imidazol-2-yl)phenyl]ethyl}-N-methylpropionamide,
(74) 3-[(2,6-Dichlorobenzenesulphonyl)methylamino]-N-{2-[4-(4,5-dihydro-1H-imidazol-2-yl)phenyl]ethyl}-N-methylpropionamide,
(75) N-{2-[4-(4,5-Dihydro-1H-imidazol-2-yl)phenyl]ethyl}-3-[(4-methoxy-2-nitrobenzenesulphonyl)methylamino]-N-methylpropionamide,
(76) N-{2-[4-(4,5-Dihydro-1H-imidazol-2-yl)phenyl]ethyl}-N-methyl-3-[methyl(thiophene-3-sulphonyl)amino]propionamide,
(77) 3-[(Benzo[b]thiophene-3-sulphonyl)methylamino]-N-{2-[4-(4,5-dihydro-1H-imidazol-2-yl)phenyl]ethyl}-N-methylpropionamide,
(78) N-{2-[4-(4,5-Dihydro-1H-imidazol-2-yl)phenyl]ethyl}-3-[(5-dimethyl-aminonaphthalene-1-sulphonyl)methylamino]-N-methylpropionamide,
(79) N-{2-[4-(4,5-Dihydro-1H-imidazol-2-yl)phenyl]ethyl}-N-methyl-3-[methyl(toluene-2-sulphonyl)amino]propionamide,
(80) N-{2-[4-(4,5-Dihydro-1H-imidazol-2-yl)phenyl]ethyl}-N-methyl-3-[methyl-(4-phenoxybenzenesulphonyl)amino]propionamide,
(81) 3-[(2,4-Dichlorophenylmethanesulphonyl)methylamino]-N-{2-[4-(4,5-dihydro-1H-imidazol-2-yl)phenyl]ethyl}-N-methylpropionamide,
(82) N-{2-[4-(4,5-Dihydro-1H-imidazol-2-yl)phenyl]ethyl}-3-[(4-methoxy-2,3,6-trimethylbenzenesulphonyl)methylamino]-N-methylpropionamide,
(83) N-{2-[4-(4,5-Dihydro-1H-imidazol-2-yl)phenyl]ethyl}-N-methyl-3-[methyl-(4-nitro-3-trifluoromethylbenzenesulphonyl)amino]propionamide,
(84) 4-[(5-Chlorothiophene-2-sulphonyl)methylamino]-N-{2-[4-(4,5-dihydro-1H-imidazol-2-yl)phenyl]ethyl}-N-methylbutyramide,
(85) 4-[(2-Chlorobenzenesulphonyl)methylamino]-N-{2-[4-(4,5-dihydro-1H-imidazol-2-yl)phenyl]ethyl}-N-methylbutyramide,
(86) N-{2-[4-(4,5-Dihydro-1H-imidazol-2-yl)phenyl]ethyl}-4-[(2,5-dimethyl-benzenesulphonyl)methylamino]-N-methylbutyramide,
(87) N-{2-[4-(4,5-Dihydro-1H-imidazol-2-yl)phenyl]ethyl}-4-[(1,2-dimethyl-1H-imidazole-4-sulphonyl)methylamino]-N-methylbutyramide,
(88) N-{2-[4-(4,5-Dihydro-1H-imidazol-2-yl)phenyl]ethyl}-4-[(4-methane-sulphonylbenzenesulphonyl)methylamino]-N-methylbutyramide,
(89) 4-[(3-Bromobenzenesulphonyl)methylamino]-N-{2-[4-(4,5-dihydro-1H-imidazol-2-yl)phenyl]ethyl}-N-methylbutyramide,
(90) 4-[(4-Bromo-5-chlorothiophene-2-sulphonyl)methylamino]-N-{2-[4-(4,5-dihydro-1H-imidazol-2-yl)phenyl]ethyl}-N-methylbutyramide,
(91) 4-[(3-Bromo-5-chlorothiophene-2-sulphonyl)methylamino]-N-{2-[4-(4,5-dihydro-1H-imidazol-2-yl)phenyl]ethyl}-N-methylbutyramide,
(92) 4-[(4,5-Dichlorothiophene-2-sulphonyl)methylamino]-N-{2-[4-(4,5-dihydro-1H-imidazol-2-yl)phenyl]ethyl}-N-methylbutyramide,
(93) N-{2-[4-(4,5-Dihydro-1H-imidazol-2-yl)phenyl]ethyl}-4-[(2,4-dimethylthiazole-5-sulphonyl)methylamino]-N-methylbutyramide,
(94) 4-[(5-Chloro-1,3-dimethyl-1H-pyrazole-4-sulphonyl)methylamino]-N-{2-[4-(4,5-dihydro-1H-imidazol-2-yl)phenyl]ethyl}-N-methylbutyramide,
(95) 4-[(4-Amino-3,5-dichlorobenzenesulphonyl)methylamino]-N-{2-[4-(4,5-dihydro-1H-imidazol-2-yl)phenyl]ethyl}-N-methylbutyramide,
(96) N-{2-[4-(4,5-Dihydro-1H-imidazol-2-yl)phenyl]ethyl}-N-methyl-4-[methyl-(2,4,5-trichlorobenzenesulphonyl)amino]butyramide,
(97) 4-[(2,5-Dichlorobenzenesulphonyl)methylamino]-N-{2-[4-(4,5-dihydro-1H-imidazol-2-yl)phenyl]ethyl}-N-methylbutyramide,
(98) 4-[(3,4-Dichlorobenzenesulphonyl)methylamino]-N-{2-[4-(4,5-dihydro-1H-imidazol-2-yl)phenyl]ethyl}-N-methylbutyramide,
(99) 4-[(4-Bromobenzenesulphonyl)methylamino]-N-{2-[4-(4,5-dihydro-1H-imidazol-2-yl)phenyl]ethyl}-N-methylbutyramide,
(100) 4-[(4-Fluorobenzenesulphonyl)methylamino]-N-{2-[4-(4,5-dihydro-1H-imidazol-2-yl)phenyl]ethyl}-N-methylbutyramide,
(101) 4-[(3-Fluorobenzenesulphonyl)methylamino]-N-{2-[4-(4,5-dihydro-1H-imidazol-2-yl)phenyl]ethyl}-N-methylbutyramide,
(102) 4-[(4-Chlorobenzenesulphonyl)methylamino]-N-{2-[4-(4,5-dihydro-1H-imidazol-2-yl)phenyl]ethyl}-N-methylbutyramide,
(103) N-{2-[4-(4,5-Dihydro-1H-imidazol-2-yl)phenyl]ethyl}-N-methyl-4-[methyl-(2-trifluoromethylbenzenesulphonyl)amino]butyramide,
(104) 4-[(5-Chloro-2-methoxybenzenesulphonyl)methylamino]-N-{2-[4-(4,5-dihydro-1H-imidazol-2-yl)phenyl]ethyl}-N-methylbutyramide,
(105) N-{2-[4-(4,5-Dihydro-1H-imidazol-2-yl)phenyl]ethyl}-N-methyl-4-[methyl(toluene-3-sulphonyl)amino]butyramide,
(106) N-{2-[4-(4,5-Dihydro-1H-imidazol-2-yl)phenyl]ethyl}-4-[(4-methoxy-benzenesulphonyl)methylamino]-N-methylbutyramide,
(107) 4-[(4-Acetylamino-3-chlorobenzenesulphonyl)methylamino]-N-{2-[4-(4,5-dihydro-1H-imidazol-2-yl)phenyl]ethyl}-N-methylbutyramide,
(108) N-{2-[4-(4,5-Dihydro-1H-imidazol-2-yl)phenyl]ethyl}-4-[(2,5-dimethoxybenzenesulphonyl)methylamino]-N-methylbutyramide,
(109) N-{2-[4-(4,5-Dihydro-1H-imidazol-2-yl)phenyl]ethyl}-4-[(3,4-dimethoxybenzenesulphonyl)methylamino]-N-methylbutyramide,
(110) N-{2-[4-(4,5-Dihydro-1H-imidazol-2-yl)phenyl]ethyl}-N-methyl-4-[methyl-(2,4,6-trimethylbenzenesulphonyl)amino]butyramide,
(111) N-{2-[4-(4,5-Dihydro-1H-imidazol-2-yl)phenyl]ethyl}-N-methyl-4-[methyl(naphthalene-2-sulphonyl)amino]butyramide,
(112) N-{2-[4-(4,5-Dihydro-1H-imidazol-2-yl)phenyl]ethyl}-N-methyl-4-[methyl-(2,3,5,6-tetramethylbenzenesulphonyl)amino]butyramide,
(113) N-{2-[4-(4,5-Dihydro-1H-imidazol-2-yl)phenyl]ethyl}-N-methyl-4-[methyl-(2-nitromethylbenzenesulphonyl)amino]butyramide,
(114) 4-[(4-Cyanobenzenesulphonyl)methylamino]-N-{2-[4-(4,5-dihydro-1H-imidazol-2-yl)phenyl]ethyl}-N-methylbutyramide, (115) 4-[(4-Amino-2,5-dichlorobenzenesulphonyl)methylamino]-N-{2-[4-(4,5-dihydro-1H-imidazol-2-yl)phenyl]ethyl}-N-methylbutyramide,
(116) 4-[(4-tert.-Butylbenzenesulphonyl)methylamino]-N-{2-[4-(4,5-dihydro-1H-imidazol-2-yl)phenyl]ethyl}-N-methylbutyramide,
(117) 4-[(4-Butoxybenzenesulphonyl)methylamino]-N-{2-[4-(4,5-dihydro-1H-imidazol-2-yl)phenyl]ethyl}-N-methylbutyramide,
(118) 4-[(2,4-Dichlorobenzenesulphonyl)methylamino]-N-{2-[4-(4,5-dihydro-1H-imidazol-2-yl)phenyl]ethyl}-N-methylbutyramide,
(119) 4-[(2-Chloro-4-fluorobenzenesulphonyl)methylamino]-N-{2-[4-(4,5-dihydro-1H-imidazol-2-yl)phenyl]ethyl}-N-methylbutyramide,
(120) N-{2-[4-(4,5-Dihydro-1H-imidazol-2-yl)phenyl]ethyl}-4-[(5-fluoro-2-methylbenzenesulphonyl)methylamino]-N-methylbutyramide,
(121) N-{2-[4-(4,5-Dihydro-1H-imidazol-2-yl)phenyl]ethyl}-4-[(4-methoxy-2-nitrobenzenesulphonyl)methylamino]-N-methylbutyramide,
(122) N-{2-[4-(4,5-Dihydro-1H-imidazol-2-yl)phenyl]ethyl}-N-methyl-4-[methyl(toluene-2-sulphonyl)amino]butyramide,
(123) N-{2-[4-(4,5-Dihydro-1H-imidazol-2-yl)phenyl]ethyl}-4-[(4-methoxy-2,3,6-trimethylbenzenesulphonyl)methylamino]-N-methylbutyramide,
(124) N-{2-[4-(4,5-Dihydro-1H-imidazol-2-yl)phenyl]ethyl}-N-methyl-4-[methyl-(4-propylbenzenesulphonyl)amino]butyramide,
(125) 4-[(2,4-Dichloro-5-methylbenzenesulphonyl)methylamino]-N-{2-[4-(4,5-dihydro-1H-imidazol-2-yl)phenyl]ethyl}-N-methylbutyramide,
(126) 4-[(3,4-Difluorobenzenesulphonyl)methylamino]-N-{2-[4-(4,5-dihydro-1H-imidazol-2-yl)phenyl]ethyl}-N-methylbutyramide,
(127) N-{2-[4-(4,5-Dihydro-1H-imidazol-2-yl)phenyl]ethyl}-N-methyl-4-[methyl-(4-pentylbenzenesulphonyl)amino]butyramide,
(128) 4-[(2-Chloro-4-cyanobenzenesulphonyl)methylamino]-N-{2-[4-(4,5-dihydro-1H-imidazol-2-yl)phenyl]ethyl}-N-methylbutyramide,
(129) N-{2-[4-(4,5-Dihydro-1H-imidazol-2-yl)phenyl]ethyl}-N-methyl-4-[methyl-(4-nitromethylbenzenesulphonyl)amino]butyramide,
(130) N-{2-[4-(4,5-Dihydro-1H-imidazol-2-yl)phenyl]ethyl}-4-[(furan-2-sulphonyl)methylamino]-N-methylbutyramide,
(131) N-{2-[4-(4,5-Dihydro-1H-imidazol-2-yl)phenyl]ethyl}-4-[(furan-3-sulphonyl)methylamino]-N-methylbutyramide,
(132) N-{2-[4-(4,5-Dihydro-1H-imidazol-2-yl)phenyl]ethyl}-4-[(thiophene-3-sulphonyl)methylamino]-N-methylbutyramide,
(133) N-{2-[4-(4,5-Dihydro-1H-imidazol-2-yl)phenyl]ethyl}-N-methyl-4-[methyl-(4-phenoxybenzenesulphonyl)amino]butyramide,
(134) 4-[(5-Chloronaphthalene-1-sulphonyl)methylamino]-N-{2-[4-(4,5-dihydro-1H-imidazol-2-yl)phenyl]ethyl}-N-methylbutyramide,
(135) N-{2-[4-(4,5-Dihydro-1H-imidazol-2-yl)phenyl]ethyl}-N-methyl-4-{methyl-[4-(morpholine-4-sulphonyl)benzenesulphonyl]amino}butyramide,
(136) 4-[(2-Chloro-4-trifluoromethylbenzenesulphonyl)methylamino]-N-{2-[4-(4,5-dihydro-1H-imidazol-2-yl)phenyl]ethyl}-N-methylbutyramide,
(137) 4-[(3,5-Dichloro-4-hydroxybenzenesulphonyl)methylamino]-N-{2-[4-(4,5-dihydro-1H-imidazol-2-yl)phenyl]ethyl}-N-methylbutyramide,
(138) N-{2-[4-(4,5-Dihydro-1H-imidazol-2-yl)phenyl]ethyl}-N-methyl-4-[methyl-(3,5-dimethylbenzenesulphonyl)amino]butyramide,
(139) N-{2-[4-(4,5-Dihydro-1H-imidazol-2-yl)phenyl]ethyl}-4-[(3-methane-sulphonylbenzenesulphonyl)methylamino]-N-methylbutyramide,
(140) N-{2-[4-(4,5-Dihydro-1H-imidazol-2-yl)phenyl]ethyl}-4-{[4-(3,3-dimethylurea)benzenesulphonyl]methylamino}-N-methylbutyramide,
(141) 4-[(Benzo[b]thiophene-3-sulphonyl)methylamino]-N-{2-[4-(4,5-dihydro-1H-imidazol-2-yl)phenyl]ethyl}-N-methylbutyramide,
(142) N-{2-[4-(4,5-Dihydro-1H-imidazol-2-yl)phenyl]ethyl}-N-methyl-4-[methyl-(4-nitro-3-trifluoromethylbenzenesulphonyl)amino]butyramide,
(143) 4-[(4-Chloro-3-nitrobenzenesulphonyl)methylamino]-N-{2-[4-(4,5-dihydro-1H-imidazol-2-yl)phenyl]ethyl}-N-methylbutyramide,
(144) N-{2-[4-(4,5-Dihydro-1H-imidazol-2-yl)phenyl]ethyl}-N-methyl-4-[methyl(toluene-4-sulphonyl)amino]butyramide,
(145) 4-[(4-Acetylaminobenzenesulphonyl)methylamino]-N-{2-[4-(4,5-dihydro-1H-imidazol-2-yl)phenyl]ethyl}-N-methylbutyramide,
(146) N-{2-[4-(4,5-Dihydro-1H-imidazol-2-yl)phenyl]ethyl}-N-methyl-4-[methyl-(3-nitromethylbenzenesulphonyl)amino]butyramide,
(147) 4-(Benzenesulphonylmethylamino)-N-{2-[4-(4,5-dihydro-1H-imidazol-2-yl)phenyl]ethyl}-N-methylbutyramide,
(148) N-{2-[4-(4,5-Dihydro-1H-imidazol-2-yl)phenyl]ethyl}-N-methyl-4-[methyl(naphthalene-1-sulphonyl)amino]butyramide,
(149) 4-(Biphenyl-4-sulphonylmethylamino)-N-{2-[4-(4,5-dihydro-1H-imidazol-2-yl)phenyl]ethyl}-N-methylbutyramide,
(150) N-{2-[4-(4,5-Dihydro-1H-imidazol-2-yl)phenyl]ethyl}-N-methyl-4-[methyl-(4-trifluoromethylbenzenesulphonyl)amino]butyramide,
(151) 4-[(2,6-Dichlorobenzenesulphonyl)methylamino]-N-{2-[4-(4,5-dihydro-1H-imidazol-2-yl)phenyl]ethyl}-N-methylbutyramide,
(152) N-{2-[4-(4,5-Dihydro-1H-imidazol-2-yl)phenyl]ethyl}-4-[(5-dimethyl-aminonaphthalene-1-sulphonyl)methylamino]-N-methylbutyramide,
(153) N-{2-[4-(4,5-Dihydro-1H-imidazol-2-yl)phenyl]ethyl}-4-[(thiophene-2-sulphonyl)methylamino]-N-methylbutyramide,
(154) Methyl 3-(4-{[3-({2-[4-(4,5-dihydro-1H-imidazol-2-yl)phenyl]ethyl}methylcarbamoyl)propyl]methylsulphamoyl}phenyl)-propionate,
(155) N-{2-[4-(4,5-Dihydro-1H-imidazol-2-yl)phenyl]ethyl}-N-methyl-4-[methyl(pyridine-2-sulphonyl)amino]butyramide,
(156) 4-[(3-Chloro-2-methylbenzenesulphonyl)methylamino]-N-{2-[4-(4,5-dihydro-1H-imidazol-2-yl)phenyl]ethyl}-N-methylbutyramide,
(157) 4-[(3-Chlorobenzenesulphonyl)methylamino]-N-{2-[4-(4,5-dihydro-1H-imidazol-2-yl)phenyl]ethyl}-N-methylbutyramide,
(158) N-{2-[4-(4,5-Dihydro-1H-imidazol-2-yl)phenyl]ethyl}-N-methyl-4-[methyl-(3-trifluoromethylbenzenesulphonyl)amino]butyramide, (159) N-{2-[4-(4,5-Dihydro-1H-imidazol-2-yl)phenyl]ethyl}-4-[(3,5-dimethylisoxazole-4-sulphonyl)methylamino]-N-methylbutyramide,
(160) N-{2-[4-(4,5-Dihydro-1H-imidazol-2-yl)phenyl]ethyl}-N-methyl-4-[methyl-(1-methyl-1H-imidazole-4-sulphonyl)amino]butyramide,
(161) 4-[(2,3-Dichlorobenzenesuphonyl)methylamino]-N-{2-[4-(4,5-dihydro-1H-imidazol-2-yl)phenyl]ethyl}-N-propylbutyramide,
(162) 4-[(2,3-Dichlorobenzenesulphonyl)methylamino]-N-{2-[4-(4,5-dihydro-1H-imidazol-2-yl)phenyl]ethyl}-N-isopropylbutyramide,
(163) 4-[(2,3-Dichlorobenzenesulphonyl)methylamino]-N-{2-[4-(4,5-dihydro-1H-imidazol-2-yl)phenyl]ethyl}-N-(2,2,2-trifluoroethyl)butyramide,
(164) 4-[(2,3-Dichlorobenzenesulphonyl)methylamino]-N-{2-[4-(4,5-dihydro-1H-imidazol-2-yl)phenyl]ethyl}-N-(2-fluoroethyl)butyramide,
(165) 4-[(2,3-Dichlorobenzenesulphonyl)methylamino]-N-(2,2-difluoroethyl)-N-{2-[4-(4,5-dihydro-1H-imidazol-2-yl)phenyl]ethyl}butyramide,
(166) 4-[(2,3-Dichlorobenzenesulphonyl)methylamino]-N-{2-[4-(4,5-dihydro-1H-imidazol-2-yl)phenyl]ethyl}-N-phenylbutyramide, their tautomers, their enantiomers, their mixtures and their salts.

A further embodiment of the present invention which is to be specifically mentioned consists in the compounds of the formula (I')

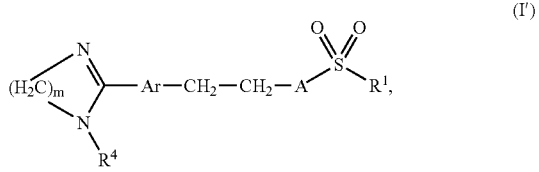
(I')

in which
R$^1$ is a phenyl or heteroaryl group,
R$^4$ is a hydrogen atom or a C$_{1-6}$-alkyl group,
m is the number 2 or 3,
Ar is a phenylene or heteroarylene group,
A is a group of the formula

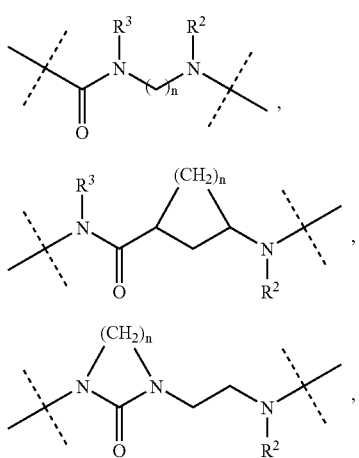
(IIa')

(IIb')

(IIc')

-continued

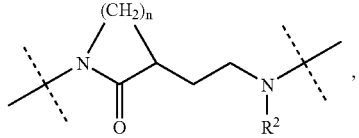
(IId')

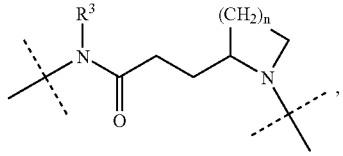
(IIe')

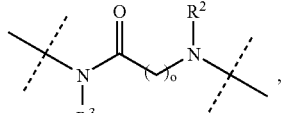
(IIf')

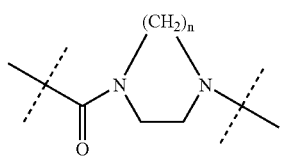
(IIg')

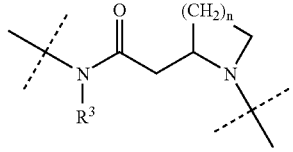
(IIh')

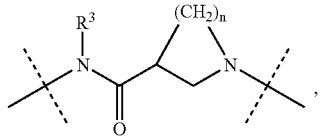
(IIi')

in which
n is the number 2 or 3,
o is the number 1, 2 or 3,
R$^2$ is a hydrogen atom, a C$_{1-6}$-alkyl, C$_{2-3}$-alkenyl, C$_{2-3}$-alkynyl, C$_{3-7}$-cycloalkyl or a phenyl group and
R$^3$ is a hydrogen atom, a C$_{1-6}$-alkyl, C$_{2-3}$-alkenyl, C$_{2-3}$-alkynyl or C$_{3-7}$-cycloalkyl group, where, unless mentioned otherwise, the term "heteroaryl group" mentioned above in the definitions is to be understood as meaning a monocyclic 5- or 6-membered heteroaryl group where
the 6-membered heteroaryl group contains one, two or three nitrogen atoms and
the 5-membered heteroaryl group contains an imino group which is optionally substituted by a C$_{1-3}$-alkyl, phenyl or phenyl-C$_{1-3}$-alkyl group, an oxygen atom or a sulphur atom or
an imino group which is optionally substituted by a C$_{1-3}$-alkyl, phenyl, amino-C$_{2-3}$-alkyl, C$_{1-3}$-alkylamino-C$_{2-3}$-alkyl, di-(C$_{1-3}$-alkyl)-amino-C$_{2-3}$-alkyl, a 4- to 7-membered cycloalkyleneimino-C$_{1-3}$-alkyl or phenyl-C$_{1-3}$-alkyl group or an oxygen or sulphur atom and additionally one nitrogen atom or
an imino group which is optionally substituted by a C$_{1-3}$-alkyl or phenyl-C$_{1-3}$-alkyl group and two or three nitrogen atoms, where the alkyl and alkoxy groups present in the definitions mentioned above which have more than two carbon atoms may, unless indicated otherwise, be straight-chain or branched, where some or all of the hydrogen atoms of the methyl or ethyl groups present in the definitions mentioned above may be replaced by fluorine atoms, and where the phenyl groups present in the definitions mentioned above may be mono-, di- or trisubstituted by fluorine, chlorine, bromine or iodine atoms, $C_{1-3}$-alkyl, trifluoromethyl, $C_{1-3}$-alkyloxy or trifluoromethyloxy groups, their tautomers, their enantiomers, their diastereomers, their mixtures and their salts.

A second embodiment of the present invention which may be particularly mentioned consists in the compounds of the formula (I') in which $R^1$ is a phenyl group which is optionally mono-, di- or trisubstituted by chlorine atoms or methyl groups, where the substituents may be identical or different, $R^4$ is a hydrogen atom, m is the number 2, Ar is a phenylene group, A is a group of the formula

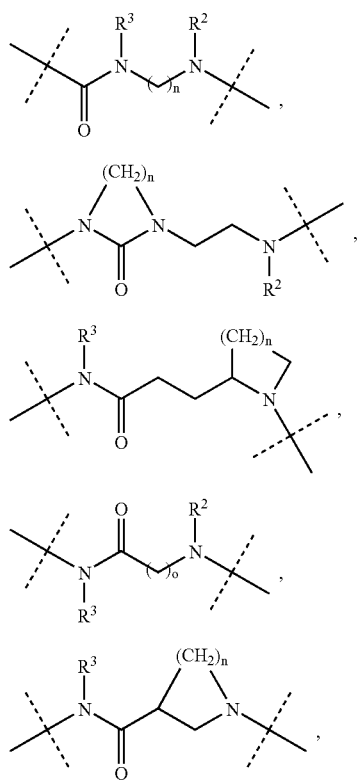

in which n is the number 2 or 3, o is the number 1, 2 or 3, $R^2$ is a hydrogen atom, a $C_{1-3}$-alkyl, cyclopropyl or a phenyl group and $R^3$ is a hydrogen atom or a methyl group, their tautomers, their enantiomers, their diastereomers, their mixtures and their salts.

The compounds of the formula (I) are prepared by methods known in principle. The following processes have been found to be particularly useful for preparing the compounds of the formula (I) according to the invention:

(a) To prepare compounds of the formula (I) in which $R^1$, $R^4$, G, A, Q and Ar are as defined at the outset:

reaction of a nitrile of the formula

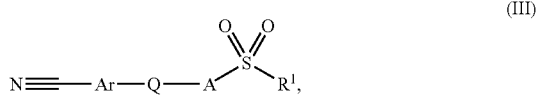

in which $R^1$, A, Q and Ar are as defined at the outset with a diamine of the formula

in which G and $R^4$ are as defined at the outset.

The reaction is preferably carried out at a temperature of from 40° C. to 150° C. in a solvent, such as, for example, tetrahydrofuran, dioxane, n-hexane, cyclohexane, benzene, toluene or xylene. The reaction is carried out with addition of $P_2S_5$ or sulphur.

(b) To prepare compounds of the formula (I) in which $R^1$, $R^4$, G, A, Q and Ar are as defined at the outset:

removal of the protective group PG from a compound of the formula

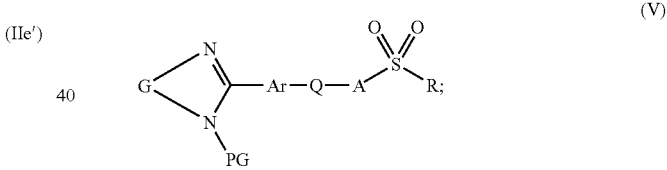

in which $R^1$, G, A, Q and Ar are as defined at the outset and PG is an amino protective group, for example the tert.-butyloxycarbonyl protective group, the benzyloxycarbonyl, methoxycarbonyl or ethoxycarbonyl group, by processes known from the literature (see, for example: Protective Groups in Organic Chemistry, 2nd Edition; Ed.: T. W. Greene, P. M. G Wuts; John Wiley & Sons, Inc.: 1991).

Depending on the type of the moiety A, the intermediates (III) and (V) can be prepared via formation of a carboxamide bond from carboxylic acid and amino building blocks selected from the group consisting of (where in the formulae (VIa) to (VId) below the ethylene group attached to Ar has the meanings of group Q in formula (I) only in an exemplary manner)

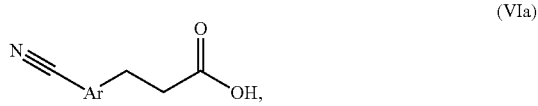

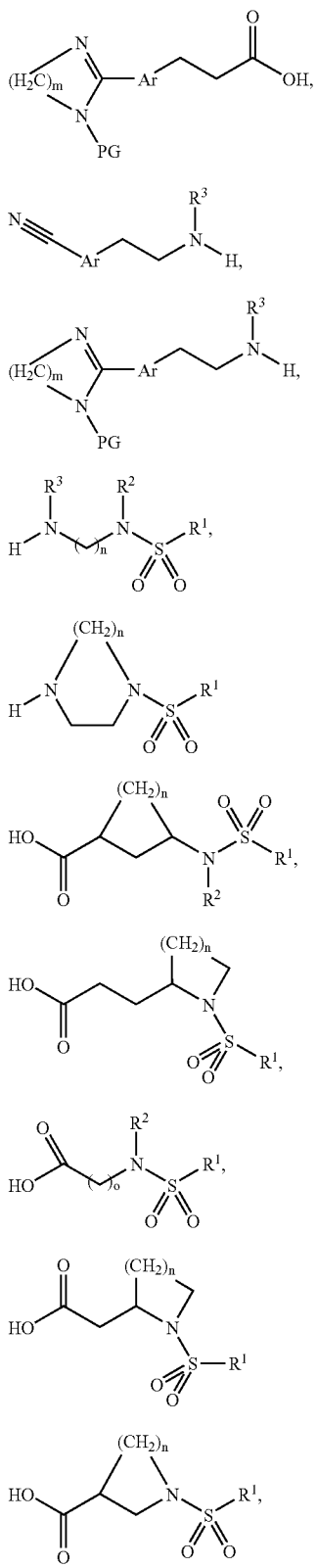

where Ar, $R^1$, $R^2$, $R^3$, m, n and o are as defined at the outset and PG is an amino protective group, for example the tert.-butyloxycarbonyl protective group, the benzyloxycarbonyl, methoxycarbonyl or ethoxycarbonyl group.

Possible routes for preparing the carboxylic acid and amino building blocks (VIa) to (VIk) are known to the person skilled in the art. These building blocks are prepared by processes known per se from the literature.

Attachment of a carboxylic acid building block of the formula (VIa) to an amino building block of formula (VIe) gives intermediates of the formula (III) in which A corresponds to a group of the formula (IIa).

Attachment of a carboxylic acid building block of the formula (VIa) to an amino building block of formula (VIf) gives intermediates of the formula (III) in which A corresponds to group of the formula (IIg).

Attachment of an amino building block of the formula (VIc) to a carboxylic acid building block of formula (VIg) gives intermediates of the formula (III) in which A corresponds to a group of the formula (IIb).

Attachment of an amino building block of the formula (VIc) to a carboxylic acid building block of formula (VIh) gives intermediates of the formula (III) in which A corresponds to a group of the formula (IIe).

Attachment of an amino building block of the formula (VIc) to a carboxylic acid building block of formula (VIh) gives intermediates of the formula (III) in which A corresponds to a group of the formula (IIf).

Attachment of an amino building block of the formula (VI) to a carboxylic acid building block of formula (VIj) gives intermediates of the formula (III) in which A corresponds to a group of the formula (IIh).

Attachment of an amino building block of the formula (VIc) to a carboxylic acid building block of formula (VIk) gives intermediates of the formula (III) in which A corresponds to a group of the formula (IIi).

Attachment of a carboxylic acid building block of the formula (VIb) to an amino building block of formula (VIe) gives intermediates of the formula (V) in which A corresponds to a group of the formula (IIa).

Attachment of a carboxylic acid building block of the formula (VIb) to an amino building block of formula (VIf) gives intermediates of the formula (V) in which A corresponds to a group of the formula (IIg).

Attachment of an amino building block of the formula (VId) to a carboxylic acid building block of formula (VIg) gives intermediates of the formula (V) in which A corresponds to a group of the formula (IIb).

Attachment of an amino building block of the formula (VId) to a carboxylic acid building block of formula (VIh) gives intermediates of the formula (V) in which A corresponds to a group of the formula (IIe).

Attachment of an amino building block of the formula (VId) to a carboxylic acid building block of formula (VIi) gives intermediates of the formula (V) in which A corresponds to a group of the formula (IIf).

Attachment of an amino building block of the formula (VId) to a carboxylic acid building block of formula (VIj) gives intermediates of the formula (V) in which A corresponds to a group of the formula (IIh).

Attachment of an amino building block of the formula (VId) to a carboxylic acid building block of formula (VIk) gives intermediates of the formula (V) in which A corresponds to a group of the formula (IIi).

The abovementioned attachments of carboxylic acids to amines with formation of carboxamides can be carried out using customary methods for amide formation.

The coupling is preferably carried out using processes known from peptide chemistry (see, for example, Houben- Weyl, Methoden der Organischen Chemie [Methods of Organic Chemistry], Vol. 15/2) where, for example, carbodiimides, such as, for example, dicyclohexylcarbodiimide (DCC), diisopropylcarbodiimide (DIC) or ethyl-(3-dimethylaminopropyl)carbodiimide, O-(1H-benzotriazol-1-yl)-N,N,N',N'-tetramethyluronium-hexafluorophosphate (HBTU) or -tetrafluoroborate (TBTU) or 1H-benzotriazol-1-yloxytris(dimethylamino)phosphonium hexafluorophosphate (BOP) are employed. The reaction rate can be increased by addition of 1-hydroxybenzotriazole (HOBt) or 3-hydroxy-4-oxo-3,4-dihydro-1,2,3-benzotriazine (HOObt). The couplings are usually carried out using equimolar proportions of the coupling components and the coupling reagent in solvents such as dichloromethane, tetrahydrofuran, acetonitrile, dimethylformamide (DMF), dimethylacetamide (DMA), N-methylpyrrolidone (NMP) or mixtures of these and at temperatures between −30° C. and +30° C., preferably between −20° C. and +25° C. If required, the preferred additional auxiliary base is N-ethyl-diisopropylamine (DIEA) (Hünig base).

(c) To prepare intermediates of the formula

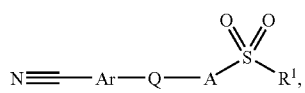
(III)

in which $R^1$, Q and Ar are defined as mentioned at the outset and A corresponds to a group of the formula (IIc) mentioned at the outset:
reaction of a cyclic urea of the formula

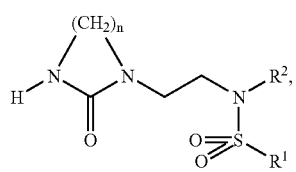
(VII)

in which $R^1$, $R^2$ and n are defined as mentioned at the outset with an electrophilic synthesis building block of the formula

(VIII)

in which Ar and Q are defined as mentioned at the outset and X is a nucleofugic group, for example the chlorine, bromine or iodine atom, the methanesulphonyl or toluenesulphonyl group.

The reaction is carried out in the presence of a base, such as, for example, potassium tert.-butoxide or sodium hydride, preferably in a solvent such as dimethylformamide or dimethyl sulphoxide.

Possible routes for preparing the synthesis building blocks (VII) and (VIII) are familiar to the person skilled in the art. These building blocks are prepared by processes known per se from the literature.

(d) To prepare intermediates of the formula

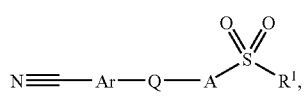
(III)

in which $R^1$, Q and Ar are defined as mentioned at the outset and A corresponds to a group of the formula (IId) mentioned at the outset:
reaction of a lactam of the formula

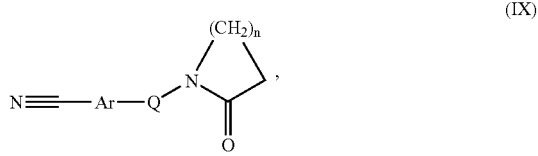
(IX)

in which Ar, Q and n are defined as mentioned at the outset with an electrophilic synthesis building block of the formula

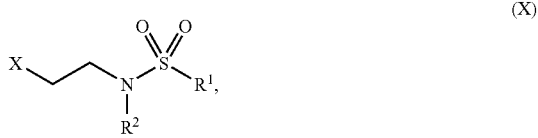
(X)

in which $R^1$ and $R^2$ are defined as mentioned at the outset and X has the meaning of a nucleofugic group, such as, for example, the chlorine, bromine or iodine atom, the methanesulphonyl or toluenesulphonyl groups.

The reaction is carried out in the presence of a base, such as, for example, butyllithium or lithium diisopropylamide, preferably in a solvent such as tetrahydrofuran or in a solvent mixture of tetrahydrofuran with hexane or toluene.

Possible routes for preparing the synthesis building blocks (IX) and (X) are familiar to the person skilled in the art. These building blocks are prepared by processes known per se from the literature.

The compounds of the formula (I) obtained can, if they contain suitable basic functions, be converted, in particular for pharmaceutical applications, into their physiologically acceptable salts with inorganic or organic acids. Acids suitable for this purpose are, for example, hydrochloric acid, hydrobromic acid, phosphoric acid, nitric acid, sulphuric acid, methanesulphonic acid, ethanesulphonic acid, benzenesulphonic acid, p-toluenesulphonic acid, acetic acid, fumaric acid, succinic acid, lactic acid, mandelic acid, malic acid, citric acid, tartaric acid or maleic acid.

Moreover, the novel compounds of the formula (I) can, if they contain carboxylic acid functions, be converted, if desired, into their addition salts with inorganic or organic bases, in particular for pharmaceutical applications into their physiologically acceptable addition salts. Bases suitable for this purpose are, for example, sodium hydroxide, potassium hydroxide, ammonia, cyclohexylamine, dicyclohexylamine, ethanolamine, diethanolamine and triethanolamine.

The present invention relates to racemates if the compounds of the formula (I) have only one element of chirality. However, the application also embraces the individual diastereomeric pairs of enantiomers or mixtures thereof which are present when more than one element of chirality is present in the compounds of the formula (I), and the individual optically active enantiomers which constitute the racemates mentioned.

The subject matter of the present invention also embraces the compounds according to the invention and their salts in which one or more hydrogen atoms are replaced by deuterium.

The novel compounds of the formula (I) and their physiologically acceptable salts have useful pharmacological properties. They are bradykinin-B1 antagonists.

For example, the compounds

A=4-[(2,3-dichlorobenzenesulphonyl)isopropylamino]-N-{2-[4-(4,5-dihydro-1H-imidazol-2-yl)phenyl]ethyl}-N-methylbutyramide (Example 4), B=3-[1-(4-chloro-2,5-dimethylbenzenesulphonyl)piperidin-2-yl]-N-{2-[4-(4,5-dihydro-1H-imidazol-2-yl)phenyl]ethyl}-N-methylpropionamide hydrochloride (Example 9), C=1-[(2,3-dichlorobenzenesulphonyl)piperidin-3-yl]-N-({2-[4-(4,5-dihydro-1H-imidazol-2-yl)phenyl]ethyl}methyl)carboxamide (Example 12), D=N-{2-[(4-chloro-2,5-dimethylbenzenesulphonyl)methylamino]ethyl}-3-[4-(4,5-dihydro-1H-imidazol-2-yl)phenyl]propionamide (Example 16) and E=2,3-dichloro-N-[2-(3-{2-[4-(4,5-dihydro-1H-imidazol-2-yl)phenyl]ethyl}-2-oxoimidazolidin-1-yl)ethyl]-N-methylbenzenesulphonamide hydrochloride (Example 17)

were examined for their biological activity as follows:

Description of the Methods for hBK1 Receptor Binding

CHO cells expressing the hBK1 receptor are cultivated in Dulbecco's modified medium. The medium from confluent cultures is removed and the cells are washed with PBS buffer, scraped off and isolated by centrifugation. The cells are then homogenized in suspension and the homogenate is centrifuged and resuspended. The protein content is determined and the membrane preparation obtained in this manner is then frozen at −80° C.

After thawing, 200 μl of the homogenate (50 to 100 μg of proteins/assay) are incubated at room temperature with 0.5 to 1.0 nM of kallidin (DesArg10, Leu9), [3,4-prolyl-3,43H(N)] and increasing concentrations of the test substance in a total volume of 250 μl for 60 minutes. The incubation is terminated by rapid filtration through GF/B glass fibre filters which had been pretreated with polyethyleneimine (0.3%). The protein-bound radioactivity is measured in a TopCount NXT. Non-specific binding is defined as radioactivity bound in the presence of 1.0 μM of kallidin (DesArg10, Leu9), [3,4-prolyl-3,43H(N)]. The concentration/binding curve is analysed using a computer-assisted nonlinear curve fitting. The $K_i$ which corresponds to the test substance is determined using the data obtained in this manner.

In the test described, substances A to E have the following $K_i$ values:

| Substance | $K_i$ |
|---|---|
| A | 62 nM |
| B | 26 nM |
| C | 957 nM |
| D | 170 nM |
| E | 1520 nM |

By virtue of their pharmacological properties, the novel compounds and their physiologically acceptable salts are suitable for treating diseases and symptoms of diseases caused at least to some extent by stimulation of bradykinin-B1 receptors. The compounds according to the invention can be used in methods which serve to alleviate or treat pain, where a therapeutically effective amount of the compound according to the invention is administered to a patient. Thus, they are suitable, for example, for treating patients having chronic pain, neuropathic pain, postoperative pain, inflammatory pain, perioperative pain, migraine, arthralgia, neuropathies, nerve injuries, diabetic neuropathy, neurodegeneration, neurotic skin diseases, stroke, irritable bladder, irritable colon, respiratory disorders, such as asthma or chronic obstructive lung disease, irritations of the skin, the eyes or the mucosa, duodenum ulcers and stomach ulcers, stomach inflammation or other inflammatory disorders, pain caused by osteoarthritis or back pain, and also pain associated with another aetiology.

For treating pain, it may be advantageous to combine the compounds according to the invention with stimulating substances such as caffeine or other pain-alleviating active compounds. If active compounds suitable for treating the cause of the pain are available, these can be combined with the compounds according to the invention. If, independently of the pain treatment, other medical treatments are also indicated, for example for high blood pressure or diabetes, the active compounds required can be combined with the compounds according to the invention.

The dosage necessary for obtaining a pain-alleviating effect is, in the case of intravenous administration, expediently from 0.01 to 3 mg/kg of body weight, preferably from 0.1 to 1 mg/kg, and, in the case of oral administration, from 0.1 to 8 mg/kg of body weight, preferably from 0.5 to 3 mg/kg, in each case 1 to 3 times per day. The compounds prepared according to the invention can be administered intravenously, subcutaneously, intramuscularly, intrarectally, intranasally, by inhalation, transdermally or orally, aerosol formulations being particularly suitable for inhalation. They can be incorporated into customary pharmaceutical preparations, such as tablets, coated tablets, capsules, powders, suspensions, solutions, metered aerosols or suppositories, if appropriate together with one or more customary inert carriers and/or diluents, for example with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances, such as hardened fat, or suitable mixtures thereof.

Experimental Part

Generally, there are IR, $^1$H NMR and/or mass spectra for the compounds that were prepared. The ratios given for the mobile phases are in volume units of the solvents in question. For $NH_3$, the given volume units are based on a concentrated solution of $NH_3$ in water.

Unless indicated otherwise, the acid, base and salt solutions used for working up the reaction solutions are aqueous systems having the stated concentrations.

For chromatographic purification, silica gel from Millipore (MATREX™, 35-70 μm) or Alox (E. Merck, Darmstadt, Alumina 90 standardized, 63-200 μm, article No. 1.01097.9050) are used.

In the descriptions of the experiments, the following abbreviations are used:

DMSO dimethyl sulphoxide

NMR nuclear magnetic resonance tert. tertiary

TBTU  2-(1H-benzotriazol-1-yl)-1,1,3,3-tetramethyluronium tetrafluoroborate

Preparation of the End Products

EXAMPLE 1

3-[(2,3-Dichlorobenzenesulphonyl)methylamino]-N-{2-[4-(4,5-dihydro-1H-imidazol-2-yl)phenyl]ethyl}-N-methylpropionamide hydrochloride

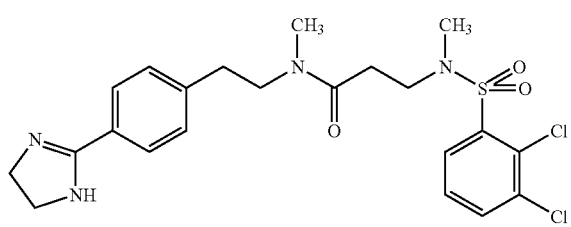

1a) tert.-Butyl 3-[(2,3-dichlorobenzenesulphonyl)methylamino]propionate

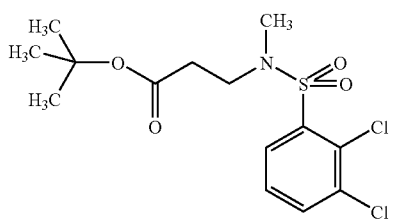

A solution of 1.0 g (6.28 mmol) of tert.-butyl N-methyl-β-alaninate, 1.54 g (6.28 mmol) of 2,3-dichlorobenzenesulphonyl chloride and 0.70 g (6.92 mmol) of triethylamine in 30 ml of tetrahydrofuran was stirred at room temperature overnight and then evaporated to dryness. About 50 ml of water were added to the residue, and the mixture was extracted three times with in each case 20 ml of ethyl acetate. The organic extracts were washed with about 20 ml of saturated sodium chloride solution and then evaporated to dryness. The crude product obtained in this manner was purified by column chromatography on silica gel (mobile phase: dichloromethane).

$C_{14}H_{19}Cl_2NO_4S$ (368.28) Yield: 19.5% of theory $^1$H-NMR ($d_6$-DMSO): δ=1.39 (s, 9H); 2.50 (t, 2H); 2.87 (s, 3H); 3.46 (t, 2H); 7.59 (t, 1H); 7.96 (2d, 2H) ppm 1b) 3-[(2,3-Dichlorobenzenesulphonyl)methylamino]propionic acid

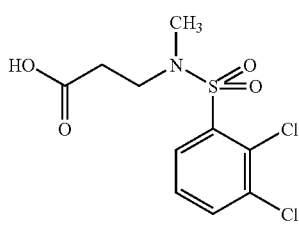

For two hours, a solution of 430 mg (1.17 mmol) of tert.-butyl 3-[(2,3-dichlorobenzenesulphonyl)methylamino] propionate and 2.0 ml of trifluoroacetic acid in 30 ml of tetrahydrofuran was stirred at room temperature and then evaporated to dryness. About 30 ml of water were added to the residue and the mixture was extracted three times with in each case 20 ml of ethyl acetate. The organic extracts were washed with saturated sodium chloride solution, dried over sodium sulphate and evaporated to dryness. The product obtained in this manner was reacted further without additional purification.

$C_{10}H_{11}Cl_2NO_4S$ (312.17) Yield: 98% of theory $^1$H-NMR ($d_6$-DMSO): δ=2.54 (t, 2H); 2.89 (s, 3H); 3.47 (t, 2H); 7.58 (t, 1H); 7.96 (2d, 2H) ppm 1c) Benzyl [2-(4-cyanophenyl)ethyl]carbamate

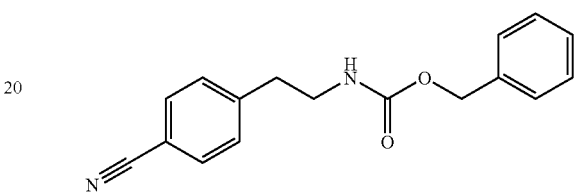

With ice bath cooling, 5.82 ml (15.57 mmol) of benzyl chloroformate (45% in toluene) were added to a solution of 2.37 g (12.98 mmol) of 4-(2-aminoethyl)benzonitrile hydrochloride and 4.34 ml (31.14 mmol) of triethylamine in 95 ml of dichloromethane. The reaction mixture was stirred at room temperature overnight and then evaporated to dryness. The crude product obtained in this manner was purified by column chromatography on silica gel (mobile phase: petroleum ether/ethyl acetate 2:1 to 1:1).

$C_9H_{10}N_2$ (146.19) Yield: 67% of theory $^1$H-NMR ($d_6$-DMSO): δ=2.81 (t, 2H), 3.27 (t, 2H), 4.99 (s, 2H), 7.26-7.43 (m, 8H), 7.73 (d, 2H) ppm 1 d) 4-(2-Methylaminoethyl)benzonitrile

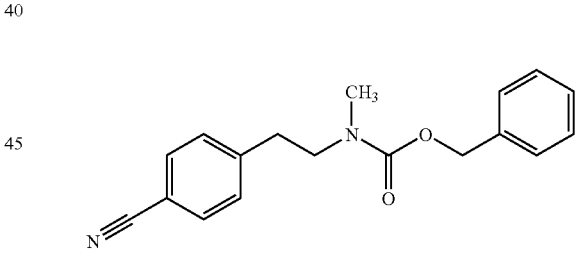

With ice bath cooling, 0.43 g (17.03 mmol) of sodium hydride (95%) was added to a solution of 3.183 g (11.36 mmol) of benzyl [2-(4-cyanophenyl)ethyl]carbamate in 70 ml of tetrahydrofuran. The mixture was stirred for a further 5 minutes with cooling and at room temperature for 10 minutes. 1.06 ml (17.03 mmol) of methyl iodide were then added to the reaction mixture, which was subsequently stirred at room temperature overnight. With ice bath cooling, the mixture was then quenched with water and extracted with ethyl acetate. The organic extracts were washed with saturated sodium chloride solution, dried over sodium sulphate and evaporated to dryness. The product obtained in this manner was reacted further without additional purification.

$C_{10}H_{12}N_2$ (160.22) Yield: 97% of theory $^1$H-NMR ($d_6$-DMSO): δ=2.77-2.93 (m, 5H); 3.50 (t, 2H), 4.92/5.02 (2s br, 2H, rotamers), 7.19-7.47 (m, 7H), 7.71 (s br, 2H) ppm

1 e) Benzyl {2-[4-(4,5-dihydro-1H-imidazol-2-yl)phenyl]ethyl}methylcarbamate

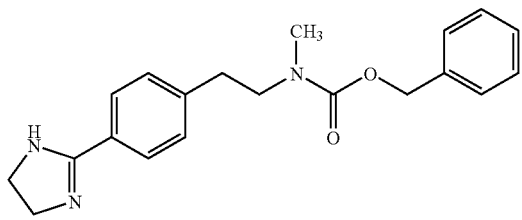

A solution of 3.33 g (11.32 mmol) of 4-(2-methylaminoethyl)benzonitrile, 14 ml of ethylenediamine and 0.182 g (5.66 mmol) of sulphur was stirred at 100° C. for one hour and then evaporated to dryness. Water was added to the residue, and the mixture was extracted with ethyl acetate. The organic extracts were washed with water and saturated sodium chloride solution, dried over sodium sulphate and concentrated. The crude product obtained in this manner was triturated with diethyl ether.

$C_{20}H_{23}N_3O_2$ (337.43) Yield: 86% of theory $^1$H-NMR ($d_6$-DMSO): δ=2.81 (m, 5H), 3.47 (t, 2H), 3.59 (s, 4H), 4.97/5.05 (2s br, 2H, rotamers), 6.84 (s br, NH), 7.15-7.40 (m, 7H), 7.73 (d br, 2H) ppm

1f) tert.-Butyl 2-{4-[2-(benzyloxycarbonylmethylamino)ethyl]phenyl}-4,5-dihydroimidazole-1-carboxylate

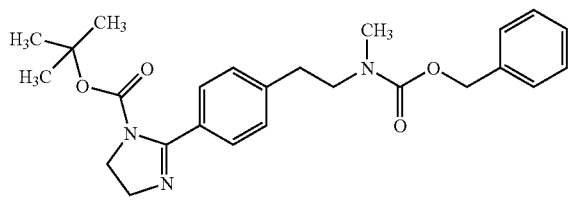

1.29 g (10.57 mmol) of dimethylaminopyridine and 2.31 g (10.57 mmol) of di-tert-butyl dicarbonate in 50 ml of dichloromethane were added successively to a solution of 3.27 g (9.69 mmol) of benzyl {2-[4-(4,5-dihydro-1H-imidazol-2-yl)phenyl]ethyl}methylcarbamate in 50 ml of dichloromethane. The reaction mixture was stirred at room temperature for 3.5 hours. The mixture was then washed with 0.5 N hydrochloric acid, with water and saturated sodium chloride solution, dried over sodium sulphate and concentrated. The crude product obtained in this manner was purified by column chromatography on silica gel (mobile phase: dichloromethane/ethanol 15:1).

$C_{25}H_{31}N_3O_4$ (437.54) Yield: 97% of theory $^1$H-NMR ($d_6$-DMSO): δ=1.18 (s, 9H), 2.78-2.88 (m, 5H), 3.46 (t, 2H), 3.84 (m, 4H), 5.00/5.06 (2s br, 2H, rotamers), 7.20 (d br, 2H), 7.28-7.41 (m, 7H) ppm

1 g) tert.-Butyl 2-[4-(2-methylaminoethyl)phenyl]-4,5-dihydroimidazole-1-carboxylate

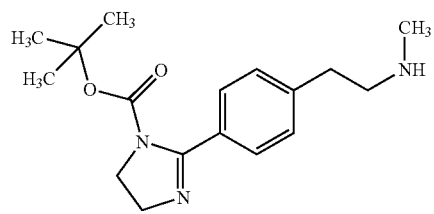

A suspension of 4.0 g (9.14 mmol) of tert.-butyl 2-{4-[2-(benzyl-oxycarbonylmethylamino)ethyl]phenyl}4,5-dihydroimidazole-1-carboxylate and 0.4 g of palladium/10% carbon in 80 ml of methanol was hydrogenated in an autoclave for two hours. The catalyst was then filtered off and the filtrate was evaporated to dryness. The crude product obtained in this manner was immediately reacted further without additional purification.

$C_{17}H_{25}N_3O_2$ (303.41) Yield: 98% of theory [M+H]$^+$=304, [M-butene-CO$_2$+H]$^+$=204

1 h) tert.-Butyl 2-{4-[2-({3-[(2,3-dichlorobenzenesulphonyl)methylamino]-propionyl}methylamino)ethyl]phenyl}-4,5-dihydroimidazole-1-caroxylate

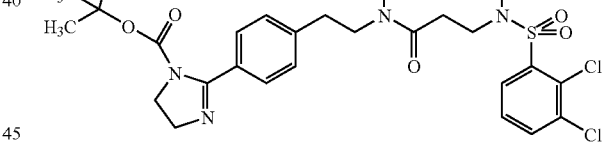

A solution of 210 mg (0.67 mmol) of 3-[(2,3-dichlorobenzenesulphonyl)-methylamino]propionic acid, 257 mg (0.80 mmol) of TBTU and 1.0 ml of triethylamine in 40 ml of tetrahydrofuran was stirred at room temperature for one hour, 204 mg (0.67 mmol) of tert.-butyl 2-[4-(2-methylaminoethyl)phenyl]-4,5-dihydroimidazole-1-carboxylate were then added and the mixture was stirred overnight. The mixture was evaporated to dryness, about 40 ml of potassium carbonate solution (10%) were added to the residue and the mixture was extracted three times with in each case 20 ml of ethyl acetate. The organic phase was washed with saturated sodium chloride solution, dried over sodium sulphate and concentrated. The crude product obtained in this manner was purified by column chromatography (mobile phase: dichloromethane/methanol 150:1).

$C_{27}H_{34}Cl_2N_4O_5S$ (597.55) Yield: 59.7% of theory $^1$H-NMR ($d_6$-DMSO): δ=1.19 (2s, 9H, rotamers); 2.40-2.95 (m, 10H); 3.35-3.53 (m, 4H); 3.77-3.92 (m, 4H); 7.25 (t, 2H); 7.38 (t, 2H); 7.54-7.62 (m, 1H); 7.89-7.98 (m, 2H) ppm 1i) 3-[(2,3-Dichlorobenzenesulphonyl)methy-
lamino]-N-{2-[4-(4,5-dihydro-1H-imidazol-2-yl)
phenyl]ethyl}-N-methylpropionamide hydrochloride

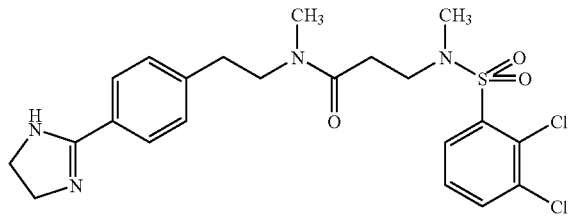

A solution of 230 mg (0.385 mmol) of tert.-butyl 2-{4-[2-({3-[(2,3-dichloro-benzenesulphonyl)methylamino] propionyl}methylamino)ethyl]phenyl}-4,5-dihydroimidazole-1-carboxylate and 3.0 ml of trifluoroacetic acid in 30 ml of dichloromethane was stirred at room temperature overnight and then evaporated to dryness. About 40 ml of potassium carbonate solution (10%) were added to the residue, and the mixture was extracted three times with in each case 20 ml of ethyl acetate. The organic extracts were washed with saturated sodium chloride solution, dried over sodium sulphate and concentrated to about 10 ml. About 15 ml of etheral hydrochloric acid were added and the mixture was evaporated to dryness. The residue was triturated with about 10 ml of ether, this suspension was re-evaporated and the product obtained in this manner was dried under reduced pressure.

$C_{22}H_{26}Cl_2N_4O_3S \times HCl$ (533.90) Yield: 68.1% of theory
$^1$H-NMR (d$_6$-DMSO): δ=2.38/2.60 (2t, 2H, rotamers); 2.78-2.98 (m, 8H); 3.27-3.44 (m, 2H); 3.49-3.60 (m, 2H); 3.99 (s, 4H); 7.47-7.62 (m, 3H); 7.88-8.04 (m, 4H); 10.70/10.72 (2s, 2H, rotamers) ppm

EXAMPLE 2

4-[(2,3-Dichlorobenzenesulphonyl)methylamino]-N-{2-[4-(4,5-dihydro-1H-imidazol-2-yl)phenyl]ethyl}-N-methylbutyramide hydrochloride

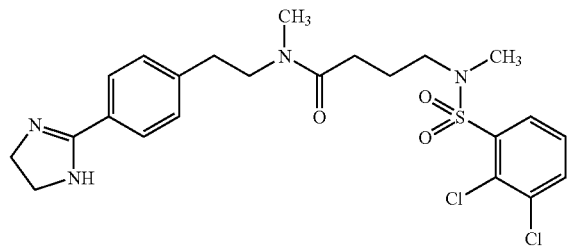

Analogously to 1i), 4-[(2,3-dichlorobenzenesulphonyl)methylamino]-N-{2-[4-(4,5-dihydro-1H-imidazol-2-yl)phenyl]ethyl}-N-methylbutyramide hydrochloride was prepared from 48 mg (0.09 mmol) of tert.-butyl 2-{4-[2-({4-[(2,3-dichlorobenzenesulphonyl)methylamino] butyryl}methylamino)ethyl]phenyl}-4,5-dihydroimidazole-1-carboxylate and 1 ml of trifluoroacetic acid in 5 ml of dichloromethane.

$C_{23}H_{28}Cl_2N_4O_3S \times HCl$ (511.47) Yield: 91% of theory
$^1$H-NMR (d$_6$-DMSO): δ=1.62/1.70 (2m, 2H, rotamers), 2.09 (s, 2H), 2.10/2.22 (2t, 2H, rotamers), 2.80/2.81 (2s, 3H, rotamers), 2.85/2.88 (2s, 3H, rotamers), 2.85/2.94 (2t, 2H, rotamers), 3.14/3.21 (2t, 2H, rotamers), 3.99 (s, 4H), 7.45-7.61 (m, 3H), 7.91-8.01 (m, 4H), 10.66/10.69 (2s br, NH, rotamers) ppm

EXAMPLE 3

4-[(2,3-Dichlorobenzenesulphonyl)phenylamino]-N-{2-[4-(4,5-dihydro-1H-imidazol-2-yl)phenyl]ethyl}-N-methylbutyramide

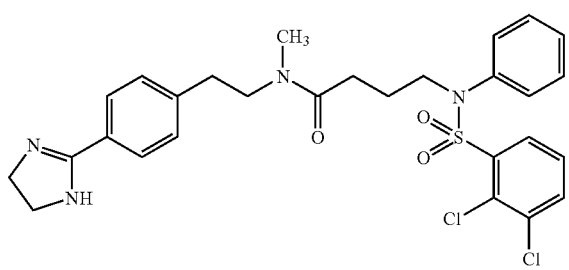

Analogously to 1i), 4-[(2,3-dichlorobenzenesulphonyl)phenylamino]-N-{2-[4-(4,5-dihydro-1H-imidazol-2-yl)phenyl]ethyl}-N-methylbutyramide was prepared from 0.252 g (0.35 mmol) of tert.-butyl 2-{4-[2-({4-[(2,3-dichloro-benzenesulphonyl)phenylamino]butyryl}methylamino)ethyl]phenyl}-4,5-di-hydroimidazole-1-carboxylate and 0.5 ml of trifluoroacetic acid in 2 ml of dichloromethane.

$C_{28}H_{30}Cl_2N_4O_3S$ (573.55) Yield: 94% of theory
$^1$H-NMR (d$_6$-DMSO): δ=1.51/1.59 (2m, 2H, rotamers), 2.18/2.29 (2t, 2H, rotamers), 2.73/2.83 (2t, 2H, rotamers), 2.77/2.84 (2s, 3H, rotamers), 3.46 (q, 2H), 3.59 (m, 4H), 3.74/3.82 (2t, 2H, rotamers), 7.18-7.40 (m, 7H), 7.46 (t, 1H), 7.70-7.82 (m, 3H), 7.92 (d, 1H) ppm

EXAMPLE 4

4-[(2,3-Dichlorobenzenesulphonyl)isopropylamino]-N-{2-[4-(4,5-dihydro-1H-imidazol-2-yl)phenyl]ethyl}-N-methylbutyramide

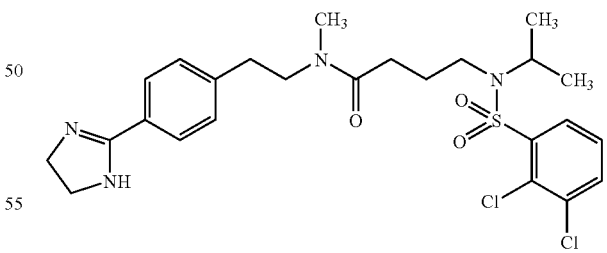

Analogously to 1i), 4-[(2,3-dichlorobenzenesulphonyl)isopropylamino]-N-{2-[4-(4,5-dihydro-1H-imidazol-2-yl)phenyl]ethyl}-N-methylbutyramide was prepared from 0.269 g (0.42 mmol) of tert.-butyl 2-{4-[2-({4-[(2,3-dichlorobenzenesulphonyl)isopropylamino]butyryl}methylamino)ethyl]phenyl}-4,5-dihydroimidazole-1-carboxylate and 0.6 ml of trifluoroacetic acid in 2 ml of dichloromethane.

$C_{25}H_{32}Cl_2N_4O_3S$ (539.53) Yield: 82% of theory
$^1$H-NMR (d$_6$-DMSO): δ=1.08 (d, 3H), 1.11 (d, 3H), 1.61/

1.70 (2m, 2H, rotamers), 2.08/2.23 (2t, 2H, rotamers), 2.75/2.83 (2t, 2H, rotamers), 2.81/2.86 (2s, 3H, rotamers), 3.15/3.26 (2t, 2H, rotamers), 3.48 (m, 2H), 3.58 (s, 4H), 3.91 (m, 1H), 7.25/7.29 (2d, 2H, rotamers), 7.57 (m, 1H), 7.73/7.76 (2d, 2H, rotamers), 7.94 (m, 1H), 8.01 (m, 1H) ppm

EXAMPLE 5

4-[(2,3-Dichlorobenzenesulphonyl)cyclopropylamino]-N-{2-[4-(4,5-dihydro-1H-imidazol-2-yl)phenyl]ethyl}-N-methylbutyramide

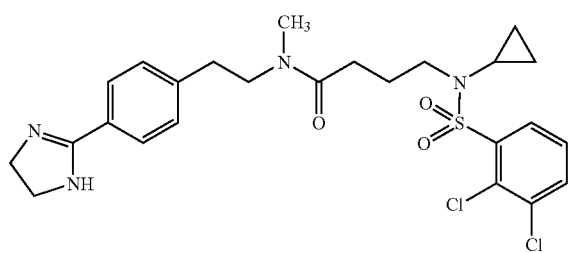

Analogously to 1i), 4-[(2,3-dichlorobenzenesulphonyl)cyclopropylamino]-N-{2-[4-(4,5-dihydro-1H-imidazol-2-yl)phenyl]ethyl}-N-methylbutyramide was prepared from 0.31 g (0.48 mmol) of tert.-butyl 2-{4-[2-({4-[(2,3-dichlorobenzenesulphonyl)cyclopropylamino]butyryl}methylamino)ethyl]phenyl}-4,5-dihydroimidazole-1-carboxylate and 0.7 ml of trifluoroacetic acid in 2 ml of dichloromethane.

$C_{25}H_{30}Cl_2N_4O_3S$ (537.51) Yield: 78% of theory
$^1$H-NMR (d$_6$-DMSO): δ=0.41 (m, 2H), 0.59 (m, 2H), 1.73/1.82 (2m, 2H, rotamers), 2.15/2.30 (2t, 2H, rotamers), 2.45/2.50 (2m, 2H, rotamers), 2.77/2.86 (2t, 2H, rotamers), 2.82/2.89 (2s, 3H rotamers), 3.28/3.39 (2t, 2H, rotamers), 3.50 (m, 2H), 3.58 (s, 4H), 7.26/7.30 (2d, 2H, rotamers), 7.59 (m, 1H), 7.73/7.75 (2d, 2H, rotamers), 7.94-8.03 (m, 2H) ppm

EXAMPLE 6

2-(Benzenesulphonylmethylamino)-N-{2-[4-(4,5-dihydro-1H-imidazol-2-yl)-phenyl]ethyl}-N-methylacetamide hydrochloride

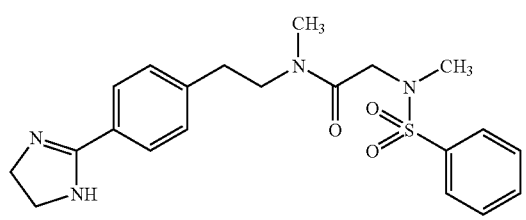

Analogously to 1i), 2-(benzenesulphonylmethylamino)-N-{2-[4-(4,5-dihydro-1H-imidazol-2-yl)phenyl]ethyl}-N-methylacetamide hydrochloride was prepared from 0.5 g (0.97 mmol) of tert.-butyl 2-[4-(2-{[2-(benzenesulphonylmethylamino)acetyl]methylamino}ethyl)phenyl]-4,5-dihydroimidazole-1-carboxylate and 5 ml of trifluoroacetic acid in 15 ml of dichloromethane.

$C_{21}H_{26}N_4O_3S \times HCl$ (450.98) Yield: 57% of theory
$^1$H-NMR (d$_6$-DMSO): δ=2.55/2.64 (2s, 3H, rotamers), 2.77-3.03 (m, 5H), 3.55 (m, 2H), 3.68/3.99 (2s, 2H, rotamers), 4.00 (s br, 4H), 7.52 (dd, 2H), 7.57-7.76 (m, 4H), 7.80 (d, 1H), 8.02 (m, 2H), 10.80/10.85 (2s, 2H, rotamers) ppm

EXAMPLE 7

3-(Benzenesulphonylmethylamino)-N-{2-[4-(4,5-dihydro-1H-imidazol-2-yl)-phenyl]ethyl}-N-methylpropionamide hydrochloride

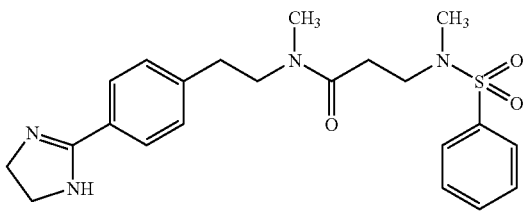

Analogously to 1i), 3-(benzenesulphonylmethylamino)-N-{2-[4-(4,5-dihydro-1H-imidazol-2-yl)phenyl]ethyl}-N-methylpropionamide hydrochloride was prepared from 0.52 g (0.98 mmol) of tert.-butyl 2-[4-(2-{[3-(benzene-sulphonymethylamino)propionyl]methylamino}ethyl)phenyl]4,5-dihydroimidazole-1-carboxylate and 5 ml of trifluoroacetic acid in 25 ml of dichloromethane.

$C_{22}H_{28}N_4O_3S \times HCl$ (465.01) Yield: 35% of theory
$^1$H-NMR (d$_6$-DMSO): δ=2.35/2.54 (2t, 2H, rotamers), 2.62/2.70 (2s, 3H, rotamers), 2.78-2.98 (m, 5H), 3.07/3.15 (2t, 2H, rotamers), 3.54 (m, 2H), 3.99 (s, 4H), 7.51 (t, 2H), 7.60-7.80 (m, 5H), 8.02 (dd, 2H), 10.75/10.79 (2s, 2H, rotamers) ppm

EXAMPLE 8

3-[1-(2,3-Dichlorobenzenesulphonyl)piperidin-2-yl]-N-{2-[4-(4,5-dihydro-1H-imidazol-2-yl)phenyl]ethyl}-N-methylpropionamide hydrochloride

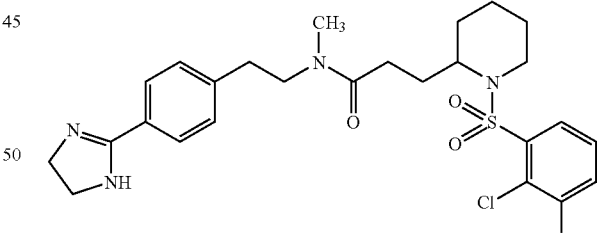

Analogously to 1i), 3-[1-(2,3-dichlorobenzenesulphonyl)piperidin-2-yl]-N-{2-[4-(4,5-dihydro-1H-imidazol-2-yl)phenyl]ethyl}-N-methylpropionamide hydrochloride was prepared from 0.44 g (0.68 mmol) of tert.-butyl 2-{4-[2-({3-[1-(2,3-dichlorobenzenesulphonyl)piperidin-2-yl]propionyl}methylamino)ethyl]phenyl}4,5-dihydroimidazole-1-carboxylate and 5 ml of trifluoroacetic acid in 15 ml of dichloromethane.

$C_{26}H_{32}Cl_2N_4O_3S \times HCl$ (587.99) Yield: 64% of theory
$^1$H-NMR (d$_6$-DMSO): δ=1.08-1.30 (m, 1H), 1.45-1.72 (m, 6H), 1.73-2.13 (m, 3H), 2.70/2.75 (2s, 3H, rotamers), 2.83/2.90 (2t, 2H, rotamers), 2.98-3.13 (m, 1H), 3.33-3.57 (m, 2H), 3.58-3.73 (m, 1H), 3.80-3.93 (m, 1H), 3.99 (s, 4H), 7.49 (t, 2H), 7.57 (m, 1H), 7.88-8.07 (m, 4H), 10.73/10.79 (2s, 2H, rotamers) ppm

EXAMPLE 9

3-[1-(4-Chloro-2,5-dimethylbenzenesulphonyl)piperidin-2-yl]-N-{2-[4-(4,5-dihydro-1H-imidazol-2-yl)phenyl]ethyl}-N-methylpropionamide hydrochloride

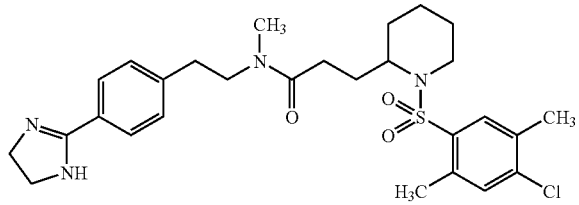

Analogously to 1i), 3-[1-(4-chloro-2,5-dimethylbenzenesulphonyl)piperidin-2-yl]-N-{2-[4-(4,5-dihydro-1H-imidazol-2-yl)phenyl]ethyl}-N-methylpropionamide hydrochloride was prepared from 0.39 g (0.60 mmol) of tert.-butyl 2-{4-[2-({3-[1-(4-chloro-2,5-dimethylbenzenesulphonyl)piperidin-2-yl]propionyl}methylamino)ethyl]phenyl}-4,5-dihydroimidazole-1-carboxylate and 4 ml of trifluoroacetic acid in 40 ml of dichloromethane.

$C_{28}H_{37}ClN_4O_3S \times HCl$ (581.60) Yield: 46% of theory
$^1$H-NMR ($d_6$-DMSO): δ=1.08-1.25 (m, 1H), 1.43-1.71 (m, 6H), 1.73-2.10 (m, 3H), 2.35 (s, 3H), 2.46 (s, 3H), 2.68-3.10 (m, 6H), 3.33-3.62 (m, 3H), 3.78 (m, 1H), 3.99 (s, 4H), 7.50 (m, 3H), 7.81 (s, 1H), 7.94-8.03 (m, 2H), 10.70/10.74 (2s, 2H, rotamers) ppm

EXAMPLE 10

3-(1-Benzenesulphonylpiperidin-2-yl)-N-{2-[4-(4,5-dihydro-1H-imidazol-2-yl)phenyl]ethyl}-N-methylpropionamide hydrochloride

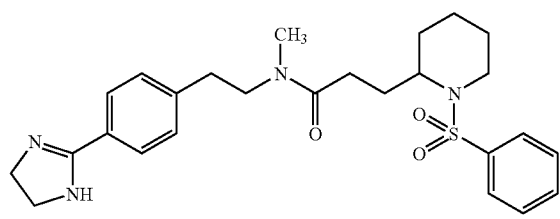

Analogously to 1i), 3-(1-benzenesulphonylpiperidin-2-yl)-N-{2-[4-(4,5-dihydro-1H-imidazol-2-yl)phenyl]ethyl}-N-methylpropionamide hydrochloride was prepared from 0.28 g (0.48 mmol) of tert.-butyl 2-{4-[2-({3-[1-benzenesulphonylpiperidin-2-yl]propionyl}methylamino)ethyl]phenyl}-4,5-dihydroimidazole-1-carboxylate and 3 ml of trifluoroacetic acid in 40 ml of dichloromethane.

$C_{26}H_{34}N_4O_3S \times HCl$ (519.10) Yield: 24% of theory
$^1$H-NMR ($d_6$-DMSO): δ=1.06-1.25 (m, 1H), 1.27-1.63 (m, 6H), 1.74-1.93 (m, 1H), 2.04-2.24 (m, 2H), 2.28-3.08 (m, 6H), 3.52 (m, 2H), 3.58-3.72 (m, 1H), 3.83-4.02 (m, 1H), 3.99 (s, 4H), 7.48-7.70 (m, 5H), 7.82 (d, 2H), 8.00 (dd, 2H), 10.68/10.71 (2s, 2H, rotamers) ppm

EXAMPLE 11

3-[1-(2,3-Dichlorobenzenesulphonyl)pyrrolidin-2(S)-yl]-N-{2-[4-(4,5-dihydro-1H-imidazol-2-yl)phenyl]ethyl}-N-methylpropionamide hydrochloride

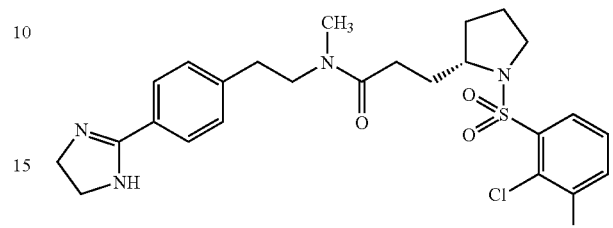

Analogously to 1i), 3-[1-(2,3-dichlorobenzenesulphonyl)pyrrolidin-2(S)-yl]-N-{2-[4-(4,5dihydro-1H-imidazol-2-yl)phenyl]ethyl}-N-methylpropionamide hydrochloride was prepared from 0.24 g (0.38 mmol) of tert.-butyl 2-{4-[2-({3-[1-(2,3-dichlorobenzenesulphonyl)pyrrolidin-2(S)-yl]propionyl}methylamino)ethyl]phenyl}-4,5-dihydroimidazole-1-carboxylate and 2 ml of trifluoroacetic acid in 30 ml of dichloromethane.

$C_{25}H_{30}Cl_2N_4O_3S \times HCl$ (573.96) Yield: 37% of theory
$^1$H-NMR ($d_6$-DMSO): δ=1.45-1.93 (m, 6H), 2.06/2.21 (2t, 2H, rotamers), 2.80/2.88 (2s, 3H, rotamers), 2.82-2.97 (m, 2H), 3.36 (m, 2H), 3.51 (t, 2H), 3.79-3.99 (m, 1H), 4.00 (s, 4H), 7.47-7.62 (m, 3H), 7.90-8.00 (m, 4H), 10.62/10.66 (2s, 2H, rotamers) ppm

EXAMPLE 12

1-(2,3-Dichlorobenzenesulphonyl)piperidin-3-yl-N-{2-[4-(4,5-dihydro-1H-imidazol-2-yl)phenyl]ethyl}-N-methylcarboxamide

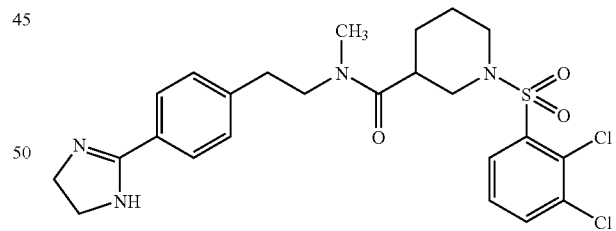

Analogously to 1i), 1-(2,3-dichlorobenzenesulphonyl)piperidin-3-yl-N-{2-[4-(4,5-dihydro-1H-imidazol-2-yl)phenyl]ethyl}-N-methylcarboxamide was prepared from 0.27 g (0.43 mmol) of tert.-butyl 2-[4-(2-{[1-(2,3-dichlorobenzenesulphonyl)piperidine-3-carbonyl]methylamino}ethyl)phenyl]-4,5-dihydroimidazole-1-carboxylate and 1 ml of trifluoroacetic acid in 5 ml of dichloromethane.

$C_{24}H_{28}Cl_2N_4O_3S$ (523.48) Yield: 29% of theory
$^1$H-NMR ($d_6$-DMSO): δ=1.08-1.84 (m, 4H), 2.65-2.95 (m, 8H), 3.43-3.75 (m, 4H), 3.60 (s, 4H), 7.25 (dd, 2H), 7.57 (m, 1H), 7.72 (dd, 2H), 7.96 (m, 2H), (imidazoline-NH not visible) ppm

EXAMPLE 13

N-{3-[(2,3-Dichlorobenzenesulphonyl)methylamino]propyl}-3-[4-(4,5-dihydro-1H-imidazol-2-yl)phenyl]propionamide

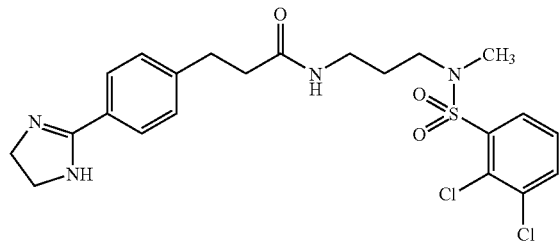

13a) 3-(4-Cyanophenyl)-N-{3-[(2,3-dichlorobenzenesulphonyl)methyl-amino]propyl}propionamide

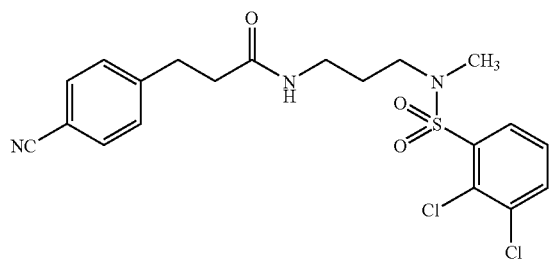

A solution of 1.47 g (8.41 mmol) of 4-cyanophenylpropionic acid, 3.1 g (9.65 mmol) of TBTU and 5.0 ml of triethylamine in 150 ml of tetrahydrofuran was stirred at room temperature for 30 minutes, 2.5 g (8.41 mmol) of N-(3-aminopropyl)-2,3-dichloro-N-methylbenzenesulphonamide were than added and the mixture was stirred overnight. The mixture was evaporated to dryness, potassium carbonate solution (10%) was added to the residue and the mixture was extracted with ethyl acetate. The organic phase was washed with water and saturated sodium chloride solution, drive over sodium sulphate and concentrated. The crude product obtained in this manner was purified by column chromatography (mobile phase: dichloromethane/methanol 150:1 to 100:1).

$C_{20}H_{21}Cl_2N_3O_3S$ (454.37) Yield: 42% of theory
$^1$H-NMR (d$_6$-DMSO): δ=1.61 (m, 2H), 2.36 (t, 2H), 2.82 (s, 3H), 2.89 (t, 2H), 3.01 (m, 2H), 3.18 (t, 2H), 7.04 (d, 2H), 7.57 (t, 1H), 7.72 (d, 2H), 7.80 (t br, NH), 7.94 (m, 2H) ppm 13b) N-{3-[(2,3-Dichlorobenzenesulphonyl)methylamino]-propyl}-3-[4-(4,5-dihydro-1H-imidazol-2-yl)phenyl]propionamide

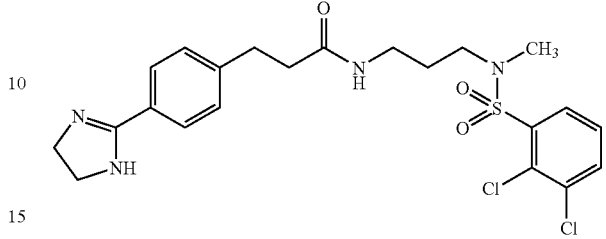

A solution of 0.7 g (1.54 mmol) of 3-(4-cyanophenyl)-N-{3-[(2,3-dichloro-benzenesulphonyl)methylamino]propyl}propionamide, 3 ml of ethylenediamine and 0.10 g (3.12 mmol) of sulphur was stirred at 100° C. for 15 minutes. Water was then added, and the mixture was extracted with ethyl acetate. The organic extracts were washed with water and saturated sodium chloride solution, dried over sodium sulphate and concentrated. The crude product obtained in this manner was purified by column chromatography on alumina (mobile phase: dichloromethane/methanol 100:1) and then crystallized from ethyl acetate/diethyl ether.

$C_{22}H_{26}Cl_2N_4O_3S$ (497.44) Yield: 47% of theory
$^1$H-NMR (d$_6$-DMSO): δ=1.62 (p, 2H), 2.37 (t, 2H), 2.82 (t, 2H), 2.83 (s, 3H), 3.02 (dt, 2H), 3.20 (t, 2H), 3.59 (s br, 4H), 6.80 (s br, 1H), 7.23 (d, 2H), 7.57 (t, 1H), 7.70 (d, 2H), 7.80 (t, 1H), 7.95 (m, 2H) ppm

EXAMPLE 14

N-{3-[(2,3-Dichlorobenzenesulphonyl)methylamino]propyl}-3-[4-(4,5-dihydro-1H-imidazol-2-yl)phenyl]-N-methylpropionamide hydrochloride

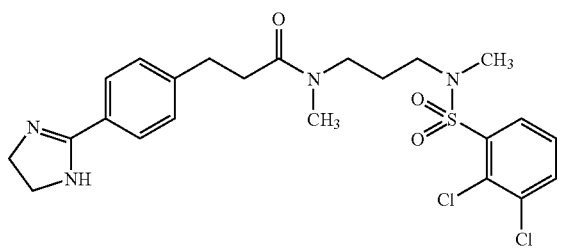

Analogously to 13b), N-{3-[(2,3-dichlorobenzenesulphonyl)methylamino]propyl}-3-[4-(4,5-dihydro-1H-imidazol-2-yl)phenyl]-N-methylpropionamide was prepared from 0.7 g (1.49 mmol) of 3-(4-cyanophenyl)-N-{3-[(2,3-dichlorobenzenesulphonyl)methylamino]propyl}-N-methylpropionamide, 0.1 g (3.12 mmol) of sulphur and 3 ml of ethylenediamine.

$C_{23}H_{28}Cl_2N_4O_3S \times HCl$ (547.93) Yield: 51% of theory
$^1$H-NMR (d$_6$-DMSO): δ=1.71 (m, 2H), 2.60 (t, 2H), 2.75-2.93 (m, 8H), 3.15-3.85 (m, 8H), 6.80 (s br, 1H), 7.28 (d, 2H), 7.57 (m, 1H), 7.72 (d, 2H), 7.95 (dd, 2H) ppm

EXAMPLE 15

3-[4-(4,5-Dihydro-1H-imidazol-2-yl)phenyl]-N-methyl-N-{3-[phenyl(toluene-4-sulphonyl)amino]propyl}propionamide

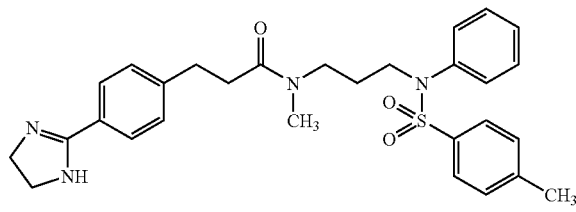

Analogously to 13b), 3-[4-(4,5-dihydro-1H-imidazol-2-yl)phenyl]-N-methyl-N-{3-[phenyl(toluene-4-sulphonyl)amino]propyl}propionamide was prepared from 1.82 g (3.83 mmol) of 3-(4-cyanophenyl)-N-methyl-N-{3-[phenyl(toluene-4-sulphonyl)amino]propyl}propionamide, 122 mg (3.83 mmol) of sulphur and 7 ml of ethylenediamine.

$C_{29}H_{34}N_4O_3S$ (518.67) Yield: 68% of theory $^1$H-NMR (d$_6$-DMSO): δ=1.48 (p, 2H), 2.39 (s, 3H), 2.46-2.59 (m, 2H), 2.69/2.83 (2s, 3H, rotamers), 2.74-2.84 (m, 2H), 3.20-3.35 (m, 2H), 3.50/3.55 (2t, 2H, rotamers), 3.59 (s br, 4H), 6.82 (s br, 1H), 7.00-7.09 (m, 2H), 7.18-7.47 (m, 9H), 7.72 (t, 2H) ppm

EXAMPLE 16

N-{2-[(4-Chloro-2,5-dimethylbenzenesulphonyl)methylamino]ethyl}-3-[4-(4,5-dihydro-1H-imidazol-2-yl)phenyl]propionamide

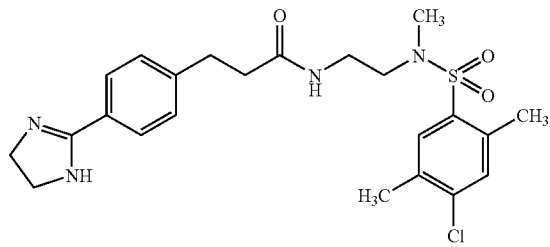

Analogously to 13b), N-{2-[(4-chloro-2,5-dimethylbenzenesulphonyl)methylamino]ethyl}-3-[4-(4,5-dihydro-1H-imidazol-2-yl)phenyl]propionamide was prepared from 1.15 g (2.65 mmol) of N-{2-[(4-chloro-2,5-dimethylbenzenesulphonyl)methylamino]ethyl}-3-(4-cyanophenyl)propionamide, 85 mg (2.65 mmol) of sulphur and 4 ml of ethylenediamine.

$C_{23}H_{29}ClN_4O_3S$ (477.02) Yield: 67% of theory $^1$H-NMR (d$_6$-DMSO): δ=2.35 (t, 2H), 2.37 (s, 3H), 2.47 (s, 3H), 2.76 (s, 3H), 2.82 (t, 2H), 3.10-3.26 (m, 4H), 3.58 (s, 4H), 7.22 (d, 2H), 7.52 (s, 1H), 7.70 (s, 1H), 7.72 (d, 2H), 7.89 (t, 1H), (imidazoline-NH not visible) ppm

EXAMPLE 17

2,3-Dichloro-N-[2-(3-{2-[4-(4,5-dihydro-1H-imidazol-2-yl)phenyl]ethyl}-2-oxoimidazolidin-1-yl)ethyl]-N-methylbenzenesulphonamide hydrochloride

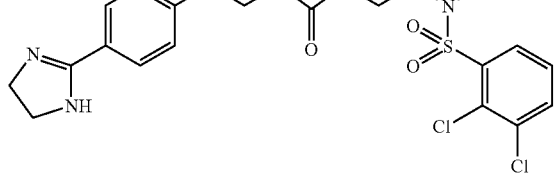

17a) 2,3-Dichloro-N-[2-(2-oxoimidazolidin-1-yl)ethyl]benzenesulphonamide

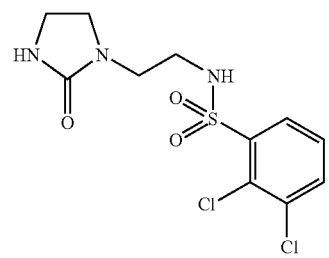

A solution of 0.5 g (2.04 mmol) of 2,3-dichlorobenzenesulphonyl chloride, 0.26 g (2.04 mmol) of 1-(2-aminoethyl)-2-imidazolidone and 1 ml (7.18 mmol) of triethylamine in 10 ml of tetrahydrofuran was stirred at room temperature overnight. The reaction mixture was then washed with 1 N HCl and saturated sodium bicarbonate solution, dried over sodium sulphate and concentrated. The product obtained in this manner was reacted further without additional purification.

$C_{11}H_{13}Cl_2N_3O_3S$ (338.21) Yield: 87% of theory $^1$H-NMR (d$_6$-DMSO): δ=2.99 (m, 2H), 3.07 (m, 2H), 3.15 (m, 2H), 3.27 (m, 2H), 6.27 (s br, NH), 7.56 (t, 1H), 7.92 (d, 1H), 7.96 (d, 1H), 8.13 (t br, NH) ppm

17b) 2,3-Dichloro-N-methyl-N-[2-(2-oxoimidazolidin-1-yl)ethyl]benzenesulponamide

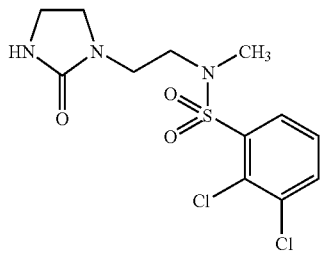

A solution of 0.57 g (1.69 mmol) of 2,3-dichloro-N-[2-(2-oxoimidazolidin-1-yl)ethyl]benzenesulphonamide and 0.23 g (1.7 mmol) of potassium carbonate in 10 ml dimethylformamide was stirred at room temperature for 10 minutes, 0.16 ml (1.69 mmol) of dimethyl sulphate were then added and the mixture was stirred at room temperature overnight. The mixture was then diluted with water and extracted with ethyl acetate. The combined organic extracts were dried over sodium sulphate and concentrated. The product obtained in this manner was crystallized using diethyl ether.

$C_{12}H_{15}Cl_2N_3O_3S$ (352.24) Yield: 72% of theory
$^1$H-NMR (d$_6$-DMSO): δ=2.88 (s, 3H), 3.17 (t, 2H), 3.24 (t, 2H), 3.26-3.38 (m, 4H), 6.28 (s br, NH), 7.56 (t, 1H), 7.95 (m, 2H) ppm

17c) 2,3-Dichloro-N-(2-{3-[2-(4-cyanophenyl)ethyl]-2-oxoimidazolidin-1-yl}ethyl)-N-methylbenzenesulphonamide

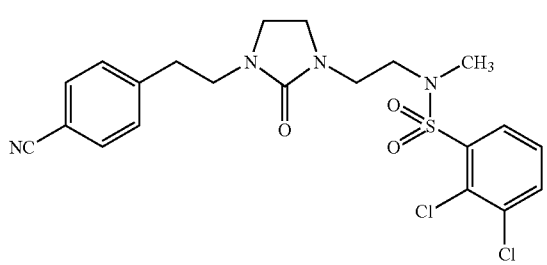

34 mg (0.84 mmol) of NaH (60%) were added to a solution of 290 mg (0.82 mmol) of 2,3-dichloro-N-methyl-N-[2-(2-oxoimidazolidin-1-yl)ethyl]benzenesulphonamide in 10 ml of dimethylformamide, and the mixture was stirred at room temperature for 10 minutes. 177 mg (0.84 mmol) of 4-(2-bromoethyl)benzonitrile were then added. The reaction mixture was stirred at 50° C. overnight. The mixture was then poured into water, 1 N HCl was added and the mixture was extracted with ethyl acetate. The combined organic extracts were washed with saturated sodium bicarbonate solution and saturated sodium chloride solution, dried over sodium sulphate and concentrated. The crude product obtained in this manner was purified by column chromatography on silica gel (mobile phase: dichloromethane/methanol 0-3%).

$C_{21}H_{22}Cl_2N_4O_3S$ (481.40) Yield: 38% of theory
$^1$H-NMR (d$_6$-DMSO): δ=2.84 (m, 2H), 2.85 (s, 3H), 3.15-3.26 (m, 6H), 3.26-3.37 (m, 4H), 7.45 (d, 2H), 7.56 (t, 1H), 7.74 (d, 2H), 7.94 (d, 2H) ppm

17d) 2,3-Dichloro-N-[2-(3-{2-[4-(4,5-dihydro-1H-imidazol-2-yl)phenyl]ethyl}-2-oxoimidazolidin-1-yl)ethyl]-N-methylbenzenesulphonamide hydrochloride

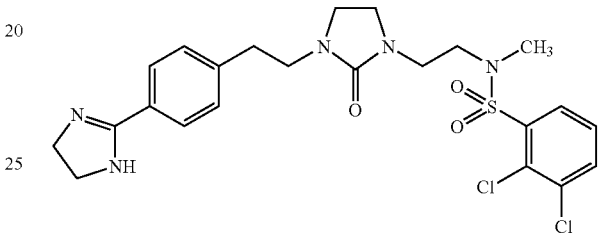

A solution of 137 mg (0.29 mmol) of 2,3-dichloro-N-(2-{3-[2-(4-cyanophenyl)ethyl]-2-oxoimidazolidin-1-yl}ethyl)-N-methylbenzenesulphonamide, 2 ml of ethylenediamine and 4.6 mg (0.14 mmol) of sulphur was stirred at 100° C. for two hours. Water was then added, and the mixture was extracted with ethyl acetate. The organic extracts were washed with saturated sodium chloride solution, dried over sodium sulphate and concentrated. The crude product obtained in this manner was purified by column chromatography on silica gel (mobile phase: dichloromethane/methanol/NH$_3$ 13:1:0.1 to 8:1:0.1). Using ethereal hydrochloric acid, the product was then converted into the hydrochloride and freeze-dried.

$C_{23}H_{27}Cl_2N_5O_3S$ (560.92) Yield: 31% of theory
$^1$H-NMR (d$_6$-DMSO): δ=2.86 (s, 2H), 2.87 (m, 2H), 3.17-3.27 (m, 6H), 3.29-3.39 (m, 4H), 3.99 (s, 4H), 3.99 (s, 4H), 7.53 (d, 2H), 7.59 (t, 1H), 7.95 (d, 2H), 7.96 (d, 2H), 10.66 (s, NH) ppm

EXAMPLE 18

2,3-Dichloro-N-[2-(3-{2-[4-(4,5-dihydro-1H-imidazol-2-yl)phenyl]ethyl}-2-oxotetrahydropyrimidin-1-yl)ethyl]-N-methylbenzenesulphonamide

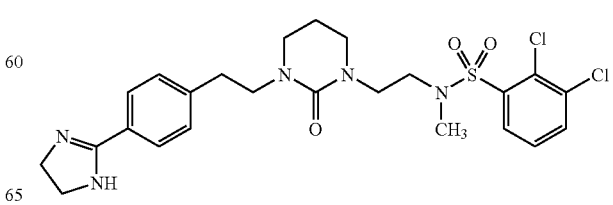

18a) tert.-Butyl (3-chloropropyl)-[2-(4-cyanophenyl)ethyl]carbamate

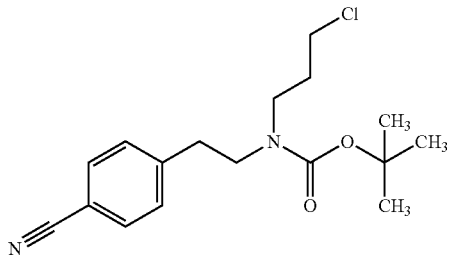

At room temperature, 0.23 g (9.03 mmol) of sodium hydride (95%) was added to a solution of 1.482 g (6.02 mmol) of tert.-butyl [2-(4-cyanophenyl)ethyl]carbamate in 25 ml of tetrahydrofuran/25 ml of dimethylformamide. The mixture was stirred for a further 15 minutes. 1.49 ml (15.04 mmol) of 1-bromo-3-chloropropane were then added, and the reaction mixture was stirred at room temperature overnight. With ice bath cooling, the mixture was then quenched with water, and extracted with ethyl acetate. The organic extracts were washed with saturated sodium chloride solution, dried over sodium sulphate and evaporated to dryness. The crude product obtained in this manner was purified by column chromatography on silica gel (mobile phase: petroleum ether/ethyl acetate 4:1).

$C_{17}H_{23}ClN_2O_4$ (322.83) Yield: 26% of theory $^1$H-NMR ($d_6$-DMSO): δ=1.33 (s br, 9H), 1.88 (m, 2H), 2.86 (t, 2H), 3.22 (t, 2H), 3.39 (t, 2H), 3.58 (t, 2H), 7.41 (d, 2H), 7.76 (d, 2H) ppm

18b) 4-[2-(3-Chloropropylamino)ethyl]benzonitrile trifluoroacetate

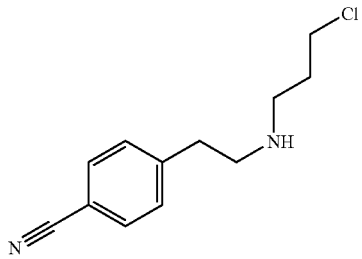

A solution of 626 mg (1.94 mmol) of tert.-butyl (3-chloropropyl)-[2-(4-cyanophenyl)ethyl]carbamate and 5.0 ml of trifluoroacetic acid in 20 ml of dichloromethane was stirred at room temperature for 1.5 hours and then evaporated to dryness. The residue was triturated with diethyl ether. The precipitate formed was then filtered off and dried under reduced pressure over calcium chloride. The product obtained in this manner was reacted further without additional purification.

$C_{12}H_{15}ClN_2 \times C_2HF_3O_2$ (336.74) Yield: 85% of theory $^1$H-NMR ($d_6$-DMSO): δ=2.08 (m, 2H), 3.02 (t, 2H), 3.08 (t, 2H), 3.25 (t, 2H), 3.73 (t, 2H), 7.50 (d, 2H), 7.82 (d, 2H), 8.84 (s br, 1H) ppm

18c) 4-Nitrophenyl {2-[(2,3-dichlorobenzenesulphonyl)methylamino]ethyl}carbamate

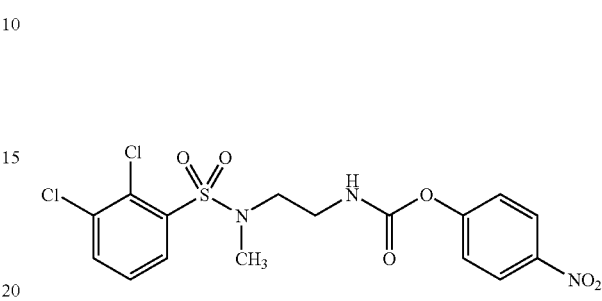

With ice bath cooling, a solution of 0.13 g (0.62 mmol) of 4-nitrophenyl chloroformate in 5 ml tetrahydrofuran was added to a solution of 0.25 g (0.62 mmol) of N-(2-aminoethyl)-2,3-dichloro-N-methylbenzenesulphonamide trifluoroacetate and 0.26 ml (1.87 mmol) of triethylamine in 5 ml of tetrahydrofuran. The reaction mixture was stirred at room temperature for one hour. The precipitate formed was then filtered off and the filtrate was evaporated to dryness. The crude product obtained in this manner was reacted further without additional purification.

$C_{16}H_{15}Cl_2N_3O_6S$ (448.28) Yield: 100% of theory $R_f$=0.96 (silica gel, dichloromethane/methanol 9:1)

18d) 2,3-Dichloro-N-(2-{1-(3-chloropropyl)-3-[2-(4-cyanophenyl)ethyl]ureido}ethyl)-N-methylbenzenesulphonamide

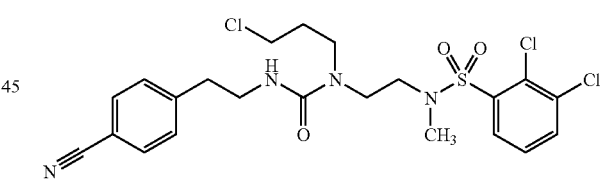

0.19 ml (1.37 mmol) of triethylamine was added to a solution of 0.31 g (0.62 mmol) of 4-nitrophenyl {2-[(2,3-dichlorobenzenesulphonyl)methylamino]ethyl}carbamate and 0.23 g (0.69 mmol) of 4-[2-(3-chloropropylamino)ethyl]benzonitrile trifluoroacetate in 12 ml of tetrahydrofuran, and the mixture was stirred at 60° C. for 1.5 hours. The mixture was then washed with 1N hydrochloric acid, with saturated sodium hydrogen sulphate solution and saturated sodium chloride solution, dried over sodium sulphate and concentrated. The crude product obtained in this manner was purified by column chromatography on silica gel (mobile phase: dichloromethane/ethanol 40:1).

$C_{22}H_{25}Cl_3N_4O_3S$ (531.88) Yield: 48% of theory $^1$H-NMR ($d_6$-DMSO): δ=1.86 (m, 2H), 2.85 (t, 2H), 2.89 (s, 3H), 3.17 (t, 2H), 3.20-3.32 (m, 4H), 3.38 (t, 2H), 3.57 (t, 2H), 6.39 (t br, 1H), 7.46 (d, 2H), 7.56 (t, 1H), 7.75 (d, 2H), 7.93 (d, 2H) ppm 18e) 2,3-Dichloro-N-(2-{3-[2-(4-cyanophenyl)ethyl]-2-oxotetrahydropyrimidin-1-yl}ethyl)-N-methylbenzenesulphonamide

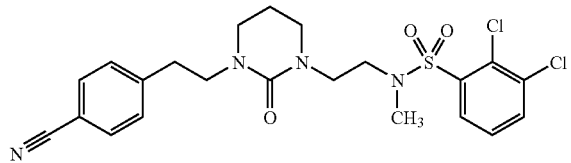

31 mg (0.28 mmol) of potassium tert.-butoxide were added to a solution of 0.147 g (0.28 mmol) of 2,3-dichloro-N-(2-{1-(3-chloropropyl)-3-[2-(4-cyanophenyl)-ethyl]ureido}ethyl)-N-methylbenzenesulphonamide in 8 ml of dimethylformamide, and the mixture was stirred at room temperature for 24 hours. The mixture was then evaporated to dryness. Water was added to the residue, and the mixture was extracted with ethyl acetate. The organic extracts were washed with water, saturated sodium hydrogen sulphate solution and saturated sodium chloride solution, dried over sodium sulphate and concentrated. The crude product obtained in this manner was purified by column chromatography on silica gel (mobile phase: dichloromethane/ethanol 40:1).

$C_{22}H_{24}Cl_2N_4O_3S$ (495.42) Yield: 88% of theory $^1$H-NMR ($d_6$-DMSO): δ=1.77 (m, 2H), 2.84 (t, 2H), 2.87 (s, 3H), 3.10 (t, 2H), 3.20 (t, 2H), 3.31-3.46 (m, 6H), 7.43 (d, 2H), 7.56 (t, 1H), 7.73 (d, 2H), 7.94 (d, 2H) ppm 18f) 2,3-Dichloro-N-[2-(3-{2-[4-(4,5-dihydro-1H-imidazol-2-yl)phenyl]ethyl}-2-oxotetrahydropyrimidin-1-yl)ethyl]-N-methylbenzenesulphonamide

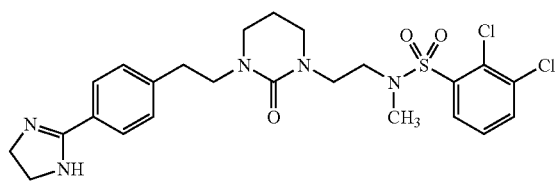

A solution of 0.135 g (0.27 mmol) of 2,3-dichloro-N-(2-{3-[2-(4-cyanophenyl)ethyl]-2-oxotetrahydropyrimidin-1-yl}ethyl)-N-methylbenzenesulphonamide, 2 ml of ethylenediamine and 17 mg (0.545 mmol) of sulphur was stirred at 100° C. for one hour. Water was then added, and the reaction mixture was extracted with ethyl acetate. The organic extracts were washed with water and saturated sodium chloride solution, drive over sodium sulphate and concentrated. The crude product obtained in this manner was purified by column chromatography on silica gel (mobile phase: dichloromethane/ethanol/aqueous ammonia solution 12:1:0.1 to 8:1:0.1).

$C_{24}H_{29}Cl_2N_5O_3S$ (538.49) Yield: 26% of theory $^1$H-NMR ($d_6$-DMSO): δ=1.76 (m, 2H), 2.78 (t, 2H), 2.88 (s, 3H), 3.09 (t, 2H), 3.20 (t, 2H), 3.23-3.45 (m, 6H), 3.59 (s, 4H), 7.27 (d, 2H), 7.56 (t, 1H), 7.73 (d, 2H), 7.94 (d, 2H), (imidazoline-NH not visible) ppm

EXAMPLE 19

4-[(2,3-Dichlorobenzenesulphonyl)methylamino]-N-methyl-N-{2-[4-(1-methyl-4,5-dihydro-1H-imidazol-2-yl)phenyl]ethyl}butyramide

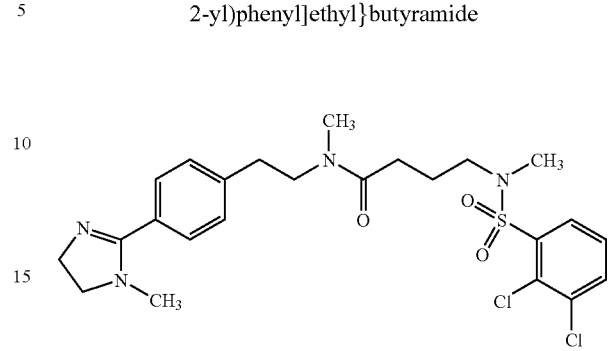

Analogously to 13b), 4-[(2,3-dichlorobenzenesulphonyl)methylamino]-N-methyl-N-{2-[4-(1-methyl-4,5-dihydro-1H-imidazol-2-yl)phenyl]ethyl}butyramide was prepared from 0.62 g (1.32 mmol) of N-[2-(4-cyanophenyl)ethyl]-4-[(2,3-dichlorobenzenesulphonyl)methylamino]-N-methylbutyramide, 48 mg (1.49 mmol) of sulphur and 3 ml of N-methylethylenediamine.

$C_{24}H_{30}Cl_2N_4O_3S$ (525.49) Yield: 62% of theory $^1$H-NMR ($d_6$-DMSO): δ=1.61/1.72 (2m, 2H, rotamers), 2.07/2.22 (2t, 2H, rotamers), 2.69 (s, 3H), 2.75/2.81 (2t, 2H, rotamers), 2.81 (s, 3H), 2.86 (s, 3H), 3.13/3.22 (2t, 2H, rotamers), 3.29/3.34 (2t, 2H, rotamers), 3.47 (t, 2H), 3.67 (t, 2H), 7.28 (m, 2H), 7.43 (m, 2H), 7.57 (t, 1H), 7.93 (m, 2H) (imidazoline-NH not visible) ppm

EXAMPLE 20

3-[(2,3-Dichlorobenzenesulphonyl)methylamino]cyclohexane-N-(2-[4-(4,5-dihydro-1H-imidazol-2-yl)phenyl]ethyl})-N-methylcarboxamide trifluoroacetate

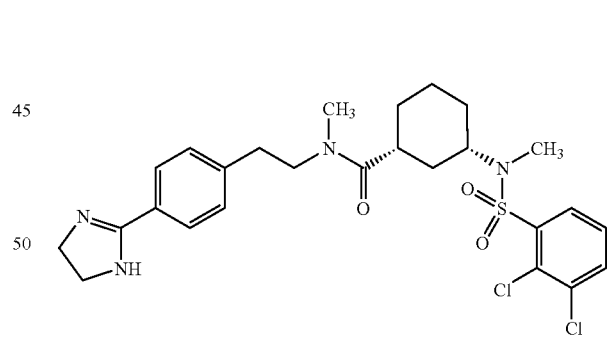

Analogously to 13b), 3-[(2,3-dichlorobenzenesulphonyl)methylamino]cyclohexane-N-(2-[4-(4,5-dihydro-1H-imidazol-2-yl)phenyl]ethyl})-N-methylcarboxamide was prepared from 0.215 g (0.423 mmol) of N-[2-(4-cyanophenyl)ethyl]-3-[(2,3-dichlorobenzenesulphonyl)methylamino]cyclohexane-N-methylcarboxamide, 6.8 mg (0.211 mmol) of sulphur and 1.2 ml of ethylenediamine.

$C_{26}H_{32}Cl_2N_4O_3S \times C_2HF_3O_2$ (665.55) Yield: 30% of theory $^1$H-NMR ($d_6$-DMSO): δ=1.01-1.59 (m, 7H), 1.64/1.73 (2m, 1H, rotamers), 2.33/2.65 (2m, 1H, rotamers), 2.70-2.94 (m, 3H), 2.73/2.77 (2s, 3H, rotamers), 2.80/2.86 (2s, 3H, rotamers), 3.36-3.75 (m, 2H), 4.00 (s, 4H), 7.47/

7.53 (2d, 2H, rotamers), 7.58 (t, 1H), 7.85/7.90 (2d, 2H, rotamers), 7.87-8.07 (m, 2H), 10.47 (s br, 1H) ppm

EXAMPLE 21

3-[(2,3-Dichlorobenzenesulphonyl)methylamino]cyclopentane-N-{2-[4-(4,5-dihydro-1H-imidazol-2-yl)phenyl]ethyl}-N-methylcarboxamide trifluoroacetate

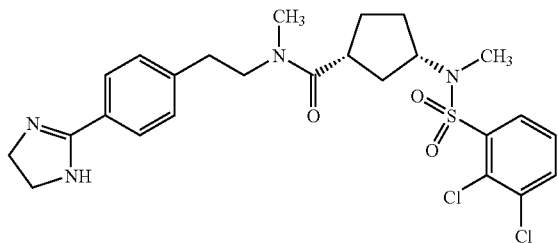

Analogously to 13b), 3-[(2,3-dichlorobenzenesulphonyl)methylamino]cyclopentane-N-{2-[4-(4,5-dihydro-1H-imidazol-2-yl)phenyl]ethyl}-N-methylcarboxamide was prepared from 0.185 g (0.374 mmol) of N-[2-(4-cyanophenyl)ethyl]-3-[(2,3-dichlorobenzenesulphonyl)methylamino]cyclopentane-N-methylcarboxamide, 6.0 mg (0.187 mmol) of sulphur and 1 ml of ethylenediamine.

$C_{25}H_{30}Cl_2N_4O_3S \times C_2HF_3O_2$ (651.53) Yield: 59% of theory $^1$H-NMR ($d_6$-DMSO): δ=1.45-1.78 (m, 6H), 2.73-3.02 (m, 3H), 2.79 (s, 3H), 2.91 (s, 3H), 2.48-3.62 (m, 2H), 4.01 (s, 4H), 4.17 (m, 1H), 7.52 (m, 2H), 7.58 (t, 1H), 7.87 (m, 2H), 7.98 (m, 2H), 10.47/10.49 (2s br, 1H) ppm

EXAMPLE 22

4-[(2,3-Dichlorobenzenesulphonyl)methylamino]-N-{2-[4-(4,5-dihydro-1H-imidazol-2-yl)phenyl]ethyl}-N-ethylbutyramide

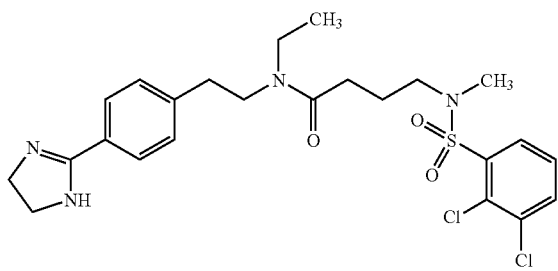

Analogously to 13b), 4-[(2,3-dichlorobenzenesulphonyl)methylamino]-N-{2-[4-(4,5-dihydro-1H-imidazol-2-yl)phenyl]ethyl}-N-ethylbutyramide was prepared from 0.74 g (1.53 mmol) of N-[2-(4-cyanophenyl)ethyl]-4-[(2,3-dichlorobenzenesulphonyl)methylamino]-N-ethylbutyramide, a spatula tip of sulphur and 5 ml of ethylenediamine.

$C_{24}H_{30}Cl_2N_4O_3S$ (525.49) Yield: 37% of theory $^1$H-NMR ($d_6$-DMSO): δ=1.00/1.04 (2t, 3H, rotamers), 1.66/1.75 (2m, 2H, rotamers), 2.16/2.26 (2t, 2H, rotamers), 2.76/2.83 (2t, 2H, rotamers), 2.82/2.86 (2s, 3H, rotamers), 3.17 (m, 2H), 3.25 (m, 2H), 3.32 (m, 2H), 3.41 (m, 2H), 3.58 (s br, 2H), 7.25/7.30 (2d, 2H, rotamers), 7.57 (t, 1H), 7.73/7.75 (2d, 2H, rotamers), 7.94 (m, 2H), (imidazoline-NH not visible) ppm

EXAMPLE 23

N-Cyclopropyl-4-[(2,3-dichlorobenzenesulphonyl)methylamino]-N-{2-[4-(4,5-dihydro-1H-imidazol-2-yl)phenyl]ethyl}butyramide

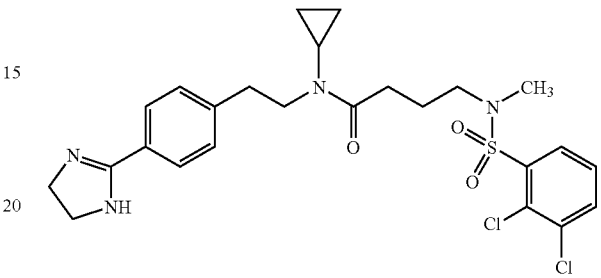

Analogously to 13b), N-cyclopropyl-4-[(2,3-dichlorobenzenesulphonyl)methylamino]-N-{2-[4-(4,5-dihydro-1H-imidazol-2-yl)phenyl]ethyl}butyramide was prepared from 0.84 g (1.70 mmol) of N-[2-(4-cyanophenyl)ethyl]-N-cyclopropyl-4-[(2,3-dichlorobenzenesulphonyl)methylamino]butyramide, 0.143 g (4.46 mmol) of sulphur and 3 ml of ethylenediamine.

$C_{25}H_{30}Cl_2N_4O_3S$ (537.50) Yield: 54% of theory $^1$H-NMR ($d_6$-DMSO): δ=0.63 (m, 2H), 0.76 (m, 2H), 1.75 (m, 2H), 2.44 (t, 2H), 2.52 (m, 1H), 2.79 (t, 2H), 2.85 (s, 3H), 3.25 (t, 2H), 3.48 (t, 2H), 3.59 (s, 4H), 7.25 (d, 2H), 7.57 (t, 1H), 7.74 (d, 2H), 7.94 (d, 2H), (imidazoline-NH not visible) ppm

EXAMPLE 24

4-[(2,3-Dichlorobenzenesulphonyl)methylamino]-N-{2-[4-(4,5-dihydro-1H-imidazol-2-yl)phenyl]ethyl}butyramide trifluoroacetate

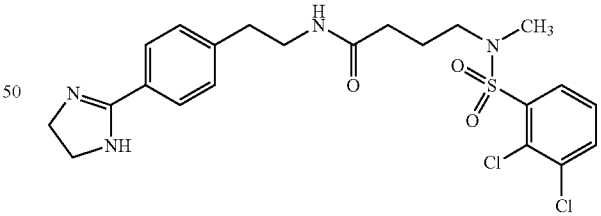

Analogously to 13b), 4-[(2,3-dichlorobenzenesulphonyl)methylamino]-N-{2-[4-(4,5-dihydro-1H-imidazol-2-yl)phenyl]ethyl}butyramide was prepared from 0.297 g (0.654 mmol) of N-[2-(4-cyanophenyl)ethyl]4-[(2,3-dichloro-benzenesulphonyl)methylamino]butyramide, 42 mg (1.31 mmol) of sulphur and 1.8 ml of ethylenediamine.

$C_{22}H_{26}Cl_2N_4O_3S \times C_2HF_3O_2$ (611.46) Yield: 46% of theory $^1$H-NMR ($d_6$-DMSO): δ=1.71 (m, 2H), 2.05 (m, 2H), 2.82 (s, 3H), 2.83 (t, 2H), 3.19 (t, 2H), 3.33 (m, 2H), 4.00 (s, 4H), 7.50 (d, 2H), 7.57 (t, 1H), 7.86 (d, 2H), 7.89-7.97 (m, 2H), 10.45 (s br, 1H) ppm

EXAMPLE 25

3-[(2,5-Dichlorobenzenesulphonyl)methylamino]-N-{2-[4-(4,5-dihydro-1H-imidazol-2-yl)phenyl]ethyl}-N-methylpropionamide

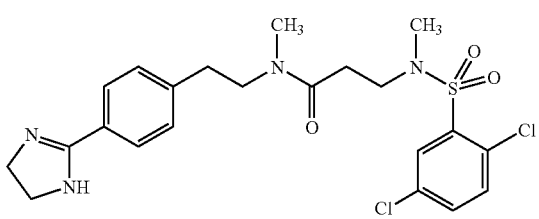

Prepared analogously to Example 13b from N-[2-(4-cyanophenyl)ethyl]-3-[(2,5-dichlorobenzenesulphonyl)methylamino]-N-methylpropionamide.

$C_{22}H_{26}Cl_2N_4O_3S$ (497.44) Yield: 39% of theory.
$^1$H-NMR (d$_6$-DMSO): δ=2.40/2.60 (2t, 2H, rotamers), 2.74-2.93 (m, 8H), 3.28-3.55 (m, 4H), 3.61 (s, 4H), 7.20 (s br, 1H), 7.28 (dd, 2H), 7.75 (m, 4H), 7.91 (dd, 1H) ppm

EXAMPLE 26

3-[(Benzo[b]thiophene-2-sulphonyl)methylamino]-N-{2-[4-(4,5-dihydro-1H-imidazol-2-yl)phenyl]ethyl}-N-methylpropionamide hydrochloride

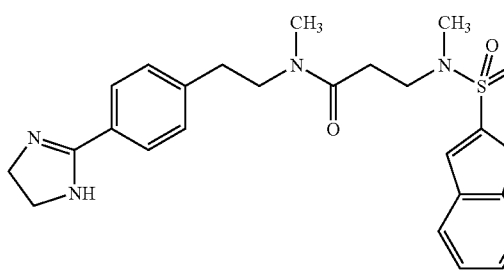

Prepared analogously to Example 13b from 3-[(benzo[b]thiophene-2-sulphonyl)methylamino]-N-[2-(4-cyanophenyl)ethyl]-N-methylpropionamide.

$C_{24}H_{28}N_4O_3S_2$×HCl (484.64) Yield: 49% of theory.
$^1$H-NMR (d$_6$-DMSO): δ=2.42/2.62 (2t, 2H, rotamers), 2.75-2.97 (m, 8H), 3.16-3.33 (m, 2H), 3.54 (m, 2H), 3.99 (s, 4H), 7.47-7.62 (m, 4H), 7.96 (dd, 2H), 8.03-8.17 (m 3H), 10.76 (d, 2H) ppm

EXAMPLE 27

3-[(2-Chlorobenzenesulphonyl)methylamino]-N-{2-[4-(4,5-dihydro-1H-imidazol-2-yl)phenyl]ethyl}-N-methylpropionamide hydrochloide

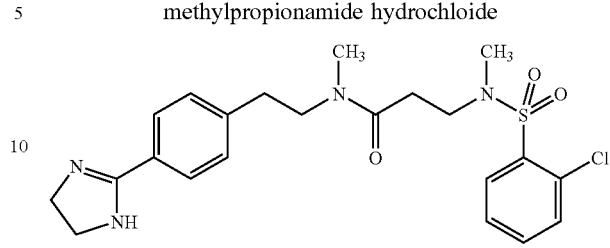

Prepared analogously to Example 13b from 3-[(2-chlorobenzenesulphonyl)-methylamino]-N-[2-(4-cyanophenyl)ethyl]-N-methylpropionamide.

$C_{22}H_{27}ClN_4O_3S$×HCl (462.99) Yield: 23% of theory.
$^1$H-NMR (d$_6$-DMSO): δ=2.37/2.60 (2t, 2H, rotamers), 2.76-2.98 (m, 8H), 3.25-3.43 (m, 2H), 3.53 (m, 2H), 4.00 (s, 4H), 7.47-7.60 (m, 3H), 7.68 (m, 2H), 7.95 (m, 3H), 10.63 (d, 2H) ppm

EXAMPLE 28

2-[1-(2,3-Dichlorobenzenesulphonyl)pyrrolidin-2-yl]-N-{2-[4-(4,5-dihydro-1H-imidazol-2-yl)phenyl]ethyl}-N-methylacetamide hydrochloride

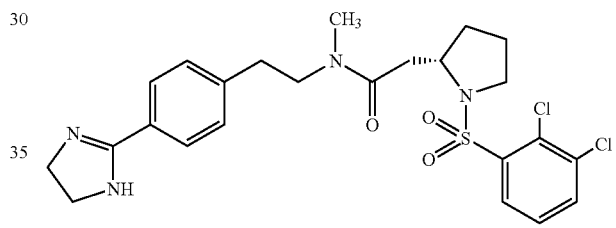

Prepared analogously to Example 13b from N-[2-(4-cyanophenyl)ethyl]-2-[1-(2,3-dichlorobenzenesulphonyl)pyrrolidin-2-yl]-N-methylacetamide.

$C_{24}H_{28}Cl_2N_4O_3S$×HCl (523.48) Yield: 44% of theory.
$^1$H-NMR (d$_6$-DMSO): δ=1.40-1.97 (m, 4H), 2.22-2.68 (m, 2H), 2.76-3.00 (m, 5H), 3.23-3.43 (m, 2H), 3.52 (m, 2H), 3.99 (s, 4H), 4.15 (m, 1H), 7.49 (m, 2H), 7.60 (m, 1H), 7.87-8.04 (m, 4H), 10.72 (d, 2H) ppm

EXAMPLE 29

N-{2-[4-(4,5-Dihydro-1H-imidazol-2-yl)phenyl]ethyl}-N-methyl-3-[methyl-(2,4,6-trimethylbenzenesulphonyl)amino]propionamide hydrochloride

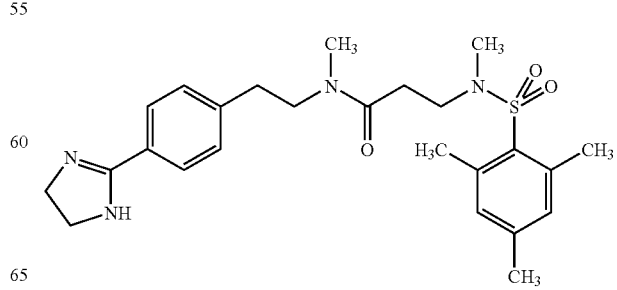

Prepared analogously to Example 13b from N-[2-(4-cyanophenyl)ethyl]-N-methyl-3-[methyl-(2,4,6-trimethylbenzenesulphonyl)amino]propionamide.

$C_{25}H_{34}N_4O_3S \times HCl$ (470.63) Yield: 42% of theory.
$^1$H-NMR (d$_6$-DMSO): δ=2.22-2.35 (m, 4H), 2.44-2.57 (m, 7H), 2.61/2.68 (2s, 3H, rotamers), 2.76-2.95 (m, 5H), 3.18/3.25 (2t, 2H, rotamers), 3.51 (t, 2H), 4.00 (s, 4H), 7.07 (d, 2H), 5.50 (m, 2H), 7.97 (m, 2H), 10.65 (d, 2H) ppm

EXAMPLE 30

3-[(2-Chloro-6-methylbenzenesulphonyl)methylamino]-N-{2-[4-(4,5-dihydro-1H-imidazol-2-yl)phenyl]ethyl}-N-methylpropionamide hydrochloride

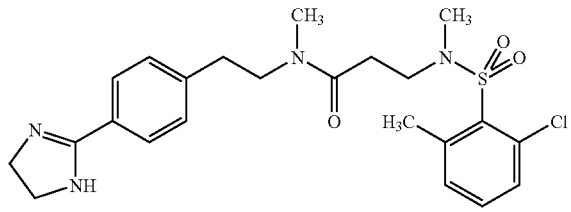

Prepared analogously to Example 13b from 3-[(2-chloro-6-methylbenzenesulphonyl)methylamino]-N-[2-(4-cyanophenyl)ethyl]-N-methylpropionamide.

$C_{23}H_{29}ClN_4O_3S \times HCl$ (477.02) Yield: 33% of theory.
$^1$H-NMR (d$_6$-DMSO): δ=2.33/2.56 (2t, 2H, rotamers), 2.61/2.63 (2s, 3H, rotamers), 2.72-2.98 (m, 8H), 3.23-3.40 (m, 2H), 3.54 (m, 2H), 4.00 (s, 4H), 7.40 (m, 1H), 7.50 (m, 4H), 7.95 (m, 2H), 10.62 (d, 2H) ppm

EXAMPLE 31

N-{2-[4-(4,5-Dihydro-1H-imidazol-2-yl)phenyl]ethyl}-N-methyl-3-[methyl(quinoline-8-sulphonyl)amino]propionamide hydrochloride

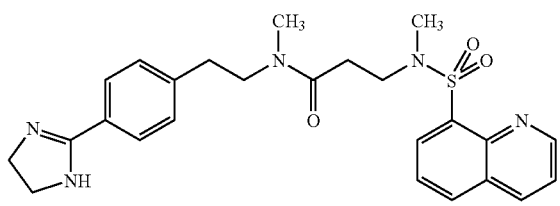

Prepared analogously to Example 13b from N-[2-(4-cyanophenyl)ethyl]-N-methyl-3-[methyl(quinoline-8-sulphonyl)amino]propionamide.

$C_{25}H_{29}N_5O_3S \times HCl$ (479.60) Yield: 43% of theory.
$^1$H-NMR (d$_6$-DMSO): δ=2.32/2.53 (2t, 2H, rotamers), 2.76- 2.95 (m, 8H), 3.35-3.55 (m, 4H), 3.99 (s, 4H), 7.49 (d, 2H), 7.67-7.80 (m, 2H), 7.96 (m, 2H), 8.28-8.40 (m, 2H), 8.53 (m, 1H), 9.06 (d, 1H), 10.66 (d, 2H) ppm

EXAMPLE 32

3-[4-(4,5-Dihydro-1H-imidazol-2-yl)phenyl]-N-methyl-N-{2-[methyl-(2,4,6-trimethylbenzenesulphonyl)amino]ethyl}propionamide hydrochloride

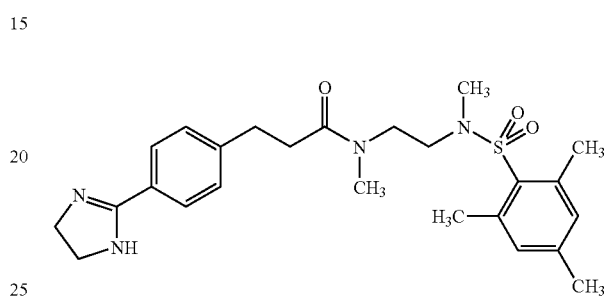

Prepared analogously to Example 13b from 3-(4-cyanophenyl)-N-methyl-N-{2-[methyl-(2,4,6-trimethylbenzenesulphonyl)amino]ethyl}propionamide.

$C_{25}H_{34}N_4O_3S \times HCl$ (470.63) Yield: 70% of theory.
$^1$H-NMR (d$_6$-DMSO): δ=2.24/2.25 (2s, 3H, rotamers), 2.46-2.78 (m, 14H), 2.89 (m, 2H), 3.13-3.26 (m, 2H), 3.45 (t, 2H), 3.99 (s, 4H), 7.05 (s, 2H), 7.50 (m, 2H), 8.02 (d, 2H), 10.83 (s, 2H) ppm

EXAMPLE 33

N-{2-[4-(4,5-Dihydro-1H-imidazol-2-yl)phenyl]ethyl}-3-[(4-trifluoromethoxy-benzenesulphonyl)methylamino]-N-methylpropionamide hydrochloride

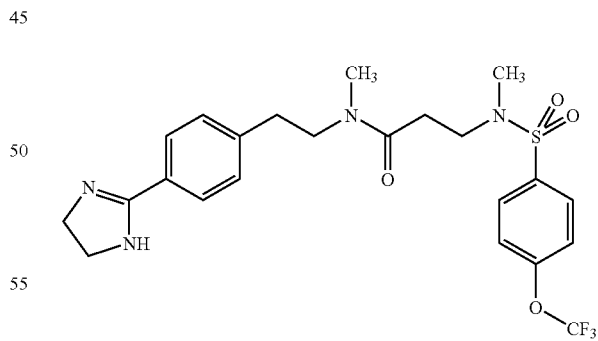

Prepared analogously to Example 13b from N-[2-(4-cyanophenyl)ethyl]-3-[(4-trifluoromethoxybenzenesulphonyl)methylamino]-N-methylpropionamide.

$C_{23}H_{27}F_3N_4O_4S \times HCl$ (512.55) Yield: 41% of theory.
$^1$H-NMR (d$_6$-DMSO): δ=2.38/2.56 (2t, 2H, rotamers), 2.65-2.98 (m, 8H), 3.10/3.20 (2t, 2H, rotamers), 3.53 (m, 2H), 3.99 (s, 4H), 7.51 (m, 2H), 7.62 (m, 2H), 7.93 (m, 4H), 10.61 (d, 2H) ppm

EXAMPLE 34

N-{2-[(4-Chloro-2,5-dimethylbenzenesulphonyl)methylamino]ethyl}-3-[4-(4,5-dihydro-1H-imidazol-2-yl)phenyl]-N-methylpropionamide hydrochlorid

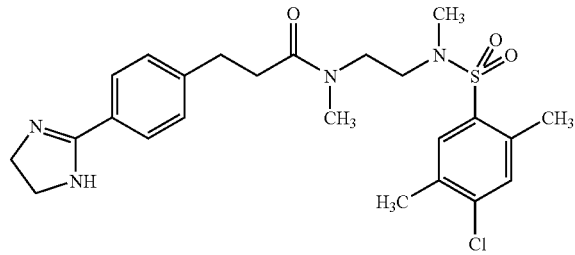

Prepared analogously to Example 13b from N-{2-[(4-chloro-2,5-dimethylbenzenesulphonyl)methylamino]ethyl}-3-(4-cyanophenyl)-N-methylpropionamide.

$C_{24}H_{31}ClN_4O_3S \times HCl$ (491.05) Yield: 63% of theory.
$^1$H-NMR (d$_6$-DMSO): δ=2.36/2.37 (2s, 3H, rotamers), 2.46/2.47 (2s, 3H, rotamers), 2.56-2.74 (m, 2H), 2.77-2.99 (m, 8H), 3.23-3.35 (m, 2H), 3.42-3.54 (m, 2H), 3.98 (s, 4H), 7.52 (m, 3H), 7.70/7.72 (2s, 1H, rotamers), 7.98 (d, 2H), 10.75 (s, 2H) ppm

EXAMPLE 35

3-[(5-Chloro-2-methoxybenzenesulphonyl)methylamino]-N-{2-[4-(4,5-dihydro-1H-imidazol-2-yl)phenyl]ethyl}-N-methylpropionamide hydrochloride

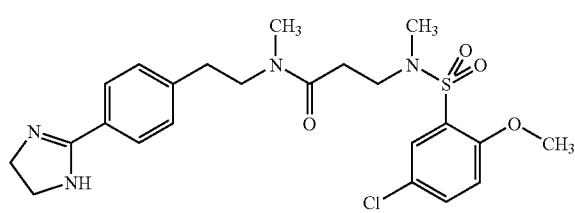

Prepared analogously to Example 13b from 3-[(5-chloro-2-methoxybenzenesulphonyl)methylamino]-N-[2-(4-cyanophenyl)ethyl]-N-methylpropionamide.

$C_{23}H_{29}ClN_4O_4S \times HCl$ (493.02) Yield: 47% of theory.
$^1$H-NMR (d$_6$-DMSO): δ=2.32/2.54 (2t, 2H, rotamers), 2.70-2.98 (m, 8H), 3.21/3.31 (2t, 2H, rotamers), 3.53 (m, 2H), 3.89/3.90 (2s, 3H, rotamers), 4.00 (s, 4H), 7.30 (m, 1H), 7.52 (m, 2H), 7.69 (m, 2H), 7.96 (m, 2H), 10.64 (d, 2H) ppm

EXAMPLE 36

N-{2-[(2,3-Dichlorobenzenesulphonyl)methylamino]ethyl}-3-[4-(4,5-dihydro-1H-imidazol-2-yl)phenyl]-N-methylpropionamide hydrochloride

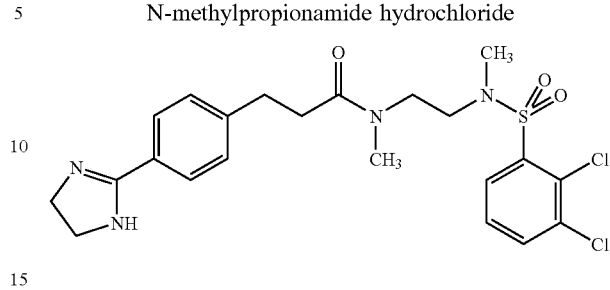

Prepared analogously to Example 13b from 3-(4-cyanophenyl)-N-{2-[(2,3-dichlorobenzenesulphonyl)methylamino]ethyl}-N-methylpropionamide.

$C_{22}H_{26}Cl_2N_4O_3S \times HCl$ (497.44) Yield: 48% of theory.
$^1$H-NMR (d$_6$-DMSO): δ=2.62/2.72 (2t, 2H, rotamers), 2.80-2.99 (m, 8H), 3.40 (m, 2H), 3.51 (m, 2H), 3.99 (s, 4H), 7.49-7.62 (m, 3H), 7.95 (m, 2H), 8.00 (d, 2H), 10.80 (s, 2H) ppm

EXAMPLE 37

3-(Cyclopropanesulphonylmethylamino)-N-{2-[4-(4,5-dihydro-1H-imidazol-2-yl)phenyl]ethyl}-N-methylpropionamide hydrochloride

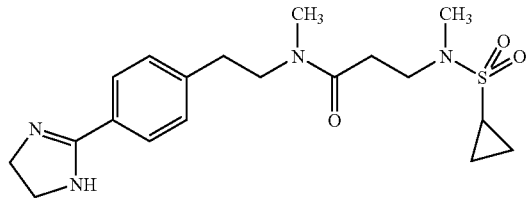

Prepared analogously to Example 13b from N-[2-(4-cyanophenyl)ethyl]-3-(cyclopropanesulphonylmethylamino)-N-methylpropionamide.

$C_{19}H_{28}Cl_2N_4O_3S \times HCl$ (392.52) Yield: 23% of theory.
$^1$H-NMR (d$_6$-DMSO): δ=0.81-1.02 (m, 4H), 2.38/2.59 (2t, 2H, rotamers), 2.55-3.00 (m, 9H), 3.22-3.36 (m, 1H), 3.41-3.63 (m, 3H), 4.00 (s, 4H), 7.53 (dd, 2H), 7.94 (dd, 2H), 9.60 (s br, 2H) ppm

EXAMPLE 38

1-[4-(2,3-Dichlorobenzenesulphonyl)-[1,4]diazepan-1-yl]-3-[4-(4,5-dihydro-1H-imidazol-2-yl)phenyl]propan-1-one hydrochloride

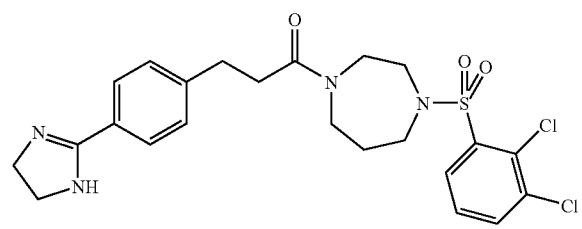

Prepared analogously to Example 13b from 4-{3-[4-(2,3-dichlorobenzenesulphonyl)-[1,4]diazepan-1-yl]-3-oxopropyl}benzonitrile.

$C_{23}H_{26}Cl_2N_4O_3S \times HCl$ (509.45) Yield: 37% of theory. $^1$H-NMR ($d_6$-DMSO): δ=1.77 (m, 2H), 2.71 (q, 2H), 2.95 (t, 2H), 3.30-3.66 (m, 8H), 3.92 (s, 4H), 7.49 (d, 2H), 7.57 (t, 1H), 7.86-7.98 (m, 4H), 10.25 (s br, 2H) ppm

EXAMPLE 39

1-[4-(2,3-Dichlorobenzenesulphonyl)piperazin-1-yl]-3-[4-(4,5-dihydro-1H-imidazol-2-yl)phenyl]propan-1-one hydrochloride

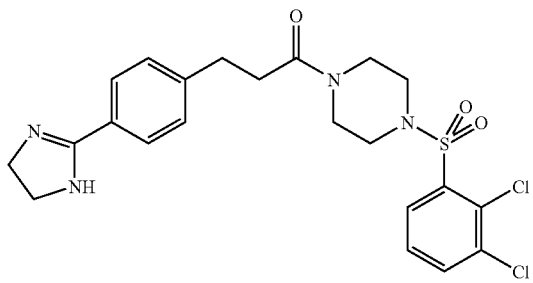

Prepared analogously to Example 13b from 4-{3-[4-(2,3-dichloro-benzenesulphonyl)piperazin-1-yl]-3-oxopropyl}benzonitrile.

$C_{22}H_{24}Cl_2N_4O_3S \times HCl$ (495.42) Yield: 40% of theory. $^1$H-NMR ($d_6$-DMSO): δ=2.66 (t, 2H), 2.85 (t, 2H), 3.20 (s br, 4H), 3.51 (s br, 4H), 3.74 (s, 4H), 7.36 (d, 2H), 7.59 (t, 1H), 7.78 (d, 2H), 7.97 (dt, 2H), (imidazoline-NH not visible) ppm

EXAMPLE 40

2-[(2,3-Dichlorobenzenesulphonyl)methylamino]-N-{2-[4-(4,5-dihydro-1H-imidazol-2-yl)phenyl]ethyl}-N-methylacetamide hydrochloride

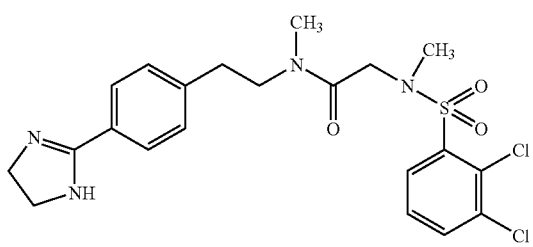

Prepared analogously to Example 13b from N-[2-(4-cyanophenyl)ethyl]-2-[(2,3-dichlorobenzenesulphonyl)methylamino]-N-methylacetamide.

$C_{21}H_{24}Cl_2N_4O_3S \times HCl$ (483.41) Yield: 22% of theory. $^1$H-NMR ($d_6$-DMSO): δ=2.70-3.00 (m, 8H), 3.54 (m, 2H), 4.00 (s, 4H), 4.01/4.24 (2s, 2H, rotamers), 7.52 (m, 3H), 7.98 (m, 4H), 10.65/10.67 (2 s br, 1H, rotamers) ppm

EXAMPLE 41

3-[(3,5-Dichlorobenzenesulphonyl)methylamino]-N-{2-[4-(4,5-dihydro-1H-imidazol-2-yl)phenyl]ethyl}-N-methylpropionamide trifluoroacetate

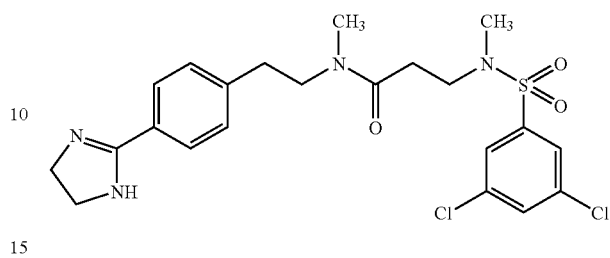

41a) tert.-Butyl 2-[4-(2-{[3-(benzylmethylamino)propionyl]methylamino}ethyl)phenyl]-4,5-dihydroimidazole-1-carboxylate

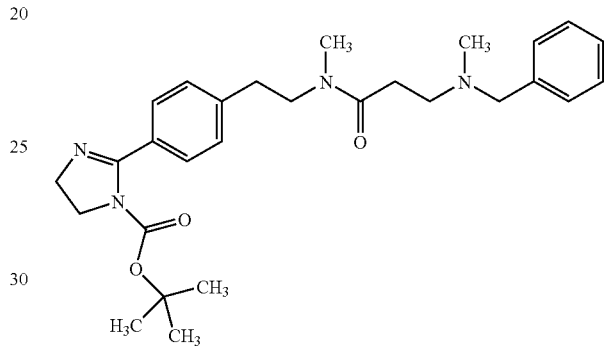

A solution of 2.08 g (9.06 mmol) of 3-(benzylmethylamino)propionic acid, 2.72 g (8.96 mmol) of tert.-butyl 2-[4-(2-methylaminoethyl)phenyl]-4,5-dihydroimidazole-1-carboxylate (see procedure 1 g), 5.05 ml (36.24 mmol) of triethylamine and 2.91 g (9.06 mmol) of TBTU in 350 ml of tetrahydrofuran was stirred at room temperature overnight. The mixture was then evaporated to dryness, and the residue was purified by column chromatography (mobile phase: dichloromethane/methanol/aqueous ammonia solution 9:1:0.1).

$C_{28}H_{38}N_4O_3$ (478.63) Yield: 84% of theory $^1$H-NMR ($d_6$-DMSO): δ=1.19/1.20 (2s, 9H), 2.05-2.95 (m, 8H), 2.07/2.13 (2s, 3H), 2.81/2.92 (2s, 3H), 3.47 (m, 2H), 3.83 (m, 4H), 7.18-7.32 (m, 7H), 7.38 (t, 2H) ppm 41 b) tert.-Butyl 2-(4-{2-[methyl-(3-methylaminopropionyl)amino]ethyl}phenyl)-4,5-dihydroimidazole-1-carboxylate

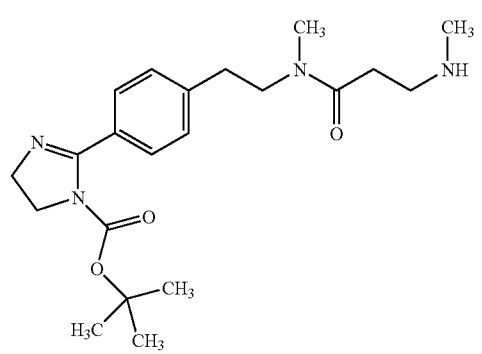

A suspension of 3.59 g (7.50 mmol) of tert.-butyl 2-[4-(2-{[3-(benzylmethylamino)propionyl]methylamino}ethyl)phenyl]4,5-dihydroimidazole-1-carboxylate and 0.36 g of palladium hydroxide in 40 ml of methanol was hydrogenated in an autoclave for ten hours. The catalyst was then filtered off and the filtrate was evaporated to dryness. The crude product obtained in this manner was purified by column chromatography on silica gel (mobile phase: dichloromethane/methanol/aqueous ammonia solution 9:1:0.1 to 4:1:0.1).

$C_{21}H_{32}N_4O_3$ (388.50) Yield: 32% of theory $^1$H-NMR ($d_6$-DMSO): δ=1.19/1.22 (2s, 9H), 2.18-2.94 (m, 6H), 2.23/2.27 (2s, 3H), 2.82/2.93 (2s, 3H), 3.49 (m, 2H), 3.84 (m, 4H), 7.23/7.27 (2d, 2H), 7.38/7.40 (2d, 2H) ppm 41c) 3-[(3,5-Dichlorobenzenesulphonyl)methylamino]-N-{2-[4-(4,5-dihydro-1H-imidazol-2-yl)phenyl]ethyl}-N-methylpropionamide trifluoroacetate

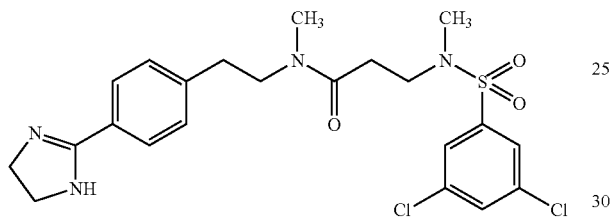

6.88 µl (65.77 µmol) of diisopropylethylamine and a solution of 3.26 mg (13.15 µmol) of 3,5-dichlorobenzenesulphonyl chloride in 150 µl of acetonitrile were added to a solution of 7.3 mg (13.15 µmol) of tert.-butyl 2-(4-{2-[methyl-(3-methylaminopropionyl)amino]ethyl}phenyl)-4,5-dihydroimidazole-1-carboxylate in 100 µl of acetonitrile. The reaction mixture was stirred at room temperature for 1.5 hours. 500 µl of a solution of trifluoroacetic acid and water (95/5) were then added, and the mixture was stirred at room temperature for a further 30 min. The reaction mixture was then evaporated to dryness in a Christ-Speedvac. The crude product obtained in this manner was purified by HPLC.

$C_{22}H_{26}Cl_2N_4O_3S\times C_2HF_3O_2$ (611.46) Yield: 66% of theory Retention time (HPLC): 3.87 min The following compounds were prepared analogously to Example 41:

EXAMPLE 42

3-(Benzenesulphonylmethylamino)-N-{2-[4-(4,5-dihydro-1H-imidazol-2-yl)-phenyl]ethyl}-N-methylpropionamide trifluoroacetate

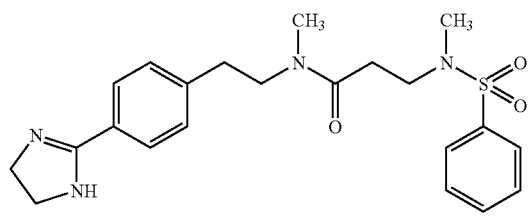

$C_{22}H_{28}N_4O_3S\times C_2HF_3O_2$ (542.57) Yield: 51% of theory Retention time (HPLC): 3.11 min

EXAMPLE 43

N-{2-[4-(4,5-Dihydro-1H-imidazol-2-yl)phenyl]ethyl}-N-methyl-3-[methyl-(4-propylbenzenesulphonyl)amino]propionamide trifluoroacetate

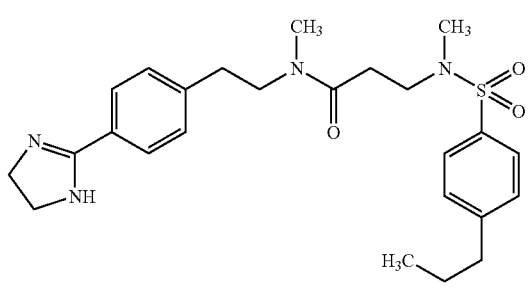

$C_{25}H_{34}N_4O_3S\times C_2HF_3O_2$ (584.66) Yield: 50% of theory Retention time (HPLC): 3.55 min

EXAMPLE 44

3-[(4-Chloro-3-nitrobenzenesulphonyl)methylamino]-N-{2-[4-(4,5-dihydro-1H-imidazol-2-yl)phenyl]ethyl}-N-methylpropionamide trifluoroacetate

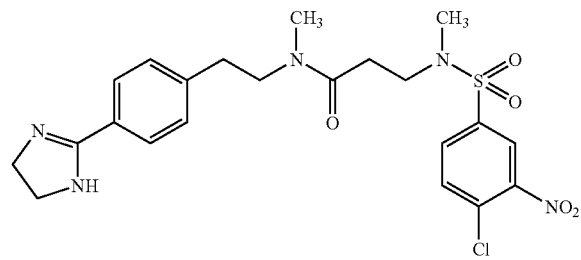

$C_{22}H_{26}ClN_5O_5S\times C_2HF_3O_2$ (622.02) Yield: 43% of theory Retention time (HPLC): 3.41 min

EXAMPLE 45

3-[(2-Chloro-6-methylbenzenesulphonyl)methylamino]-N-{2-[4-(4,5-dihydro-1H-imidazol-2-yl)phenyl]ethyl}-N-methylpropionamide trifluoroacetate

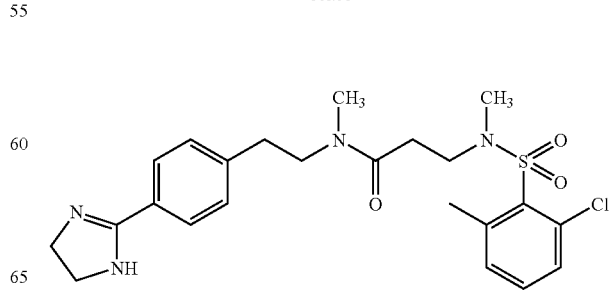

$C_{23}H_{29}ClN_4O_3S \times C_2HF_3O_2$ (591.05) Yield: 51% of theory Retention time (HPLC): 3.31 min

EXAMPLE 46

N-{2-[4-(4,5-Dihydro-1H-imidazol-2-yl)phenyl]ethyl}-3-[(4-isopropyl-benzenesulphonyl)methylamino]-N-methylpropionamide trifluoroacetate

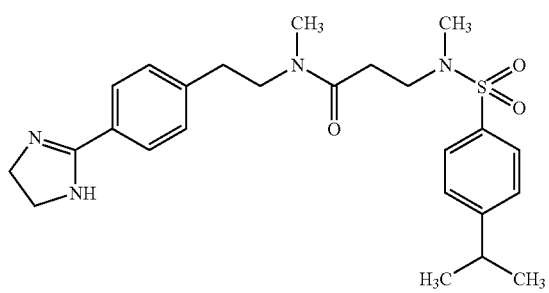

$C_{25}H_{34}N_4O_3S \times C_2HF_3O_2$ (584.66) Yield: 65% of theory Retention time (HPLC): 3.51 min

EXAMPLE 47

3-[(5-Chloronaphthalene-1-sulphonyl)methylamino]-N-{2-[4-(4,5-dihydro-1H-imidazol-2-yl)phenyl]ethyl}-N-methylpropionamide trifluoroacetate

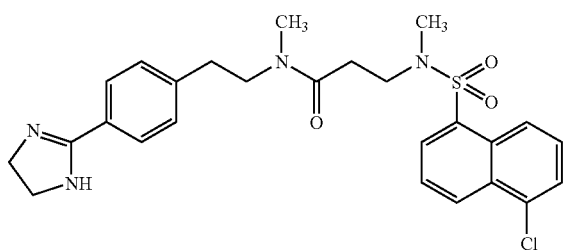

$C_{26}H_{29}ClN_4O_3S \times C_2HF_3O_2$ (627.08) Yield: 56% of theory Retention time (HPLC): 3.96 min

EXAMPLE 48

N-{2-[4-(4,5-Dihydro-1H-imidazol-2-yl)phenyl]ethyl}-N-methyl-3-[methyl(toluene-4-sulphonyl)amino]propionamide trifluoroacetate

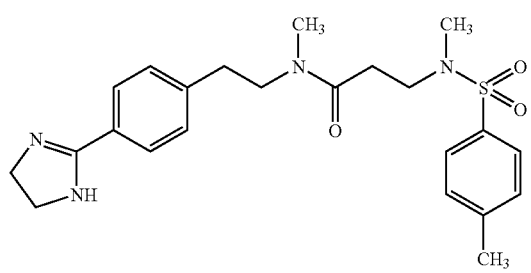

$C_{23}H_{30}N_4O_3S \times C_2HF_3O_2$ (556.60) Yield: 58% of theory Retention time (HPLC): 3.25 min

EXAMPLE 49

3-[(2-Bromobenzenesulphonyl)methylamino]-N-{2-[4-(4,5-dihydro-1H-imidazol-2-yl)phenyl]ethyl}-N-methylpropionamide trifluoroacetate

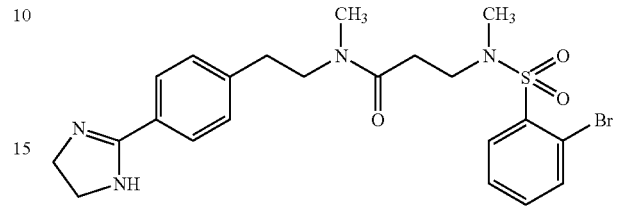

$C_{22}H_{27}BrN_4O_3S \times C_2HF_3O_2$ (621.47) Yield: 52% of theory Retention time (HPLC): 3.24 min

EXAMPLE 50

3-[(2,4-Dichloro-5-methylbenzenesulphonyl)methylamino]-N-{2-[4-(4,5-dihydro-1H-imidazol-2-yl)phenyl]ethyl}-N-methylpropionamide trifluoroacetate

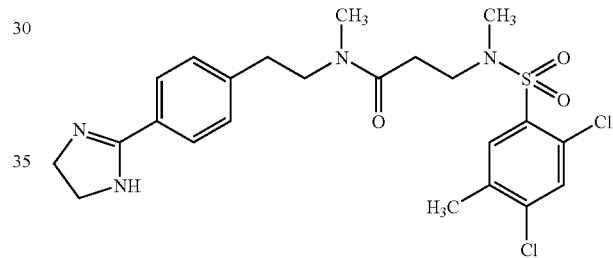

$C_{23}H_{28}Cl_2N_4O_3S \times C_2HF_3O_2$ (625.49) Yield: 70% of theory Retention time (HPLC): 3.56 min

EXAMPLE 51

N-{2-[4-(4,5-Dihydro-1H-imidazol-2-yl)phenyl]ethyl}-N-methyl-3-{methyl-[4-(morpholine-4-sulphonyl)benzenesulphonyl]amino}propionamide trifluoroacetate

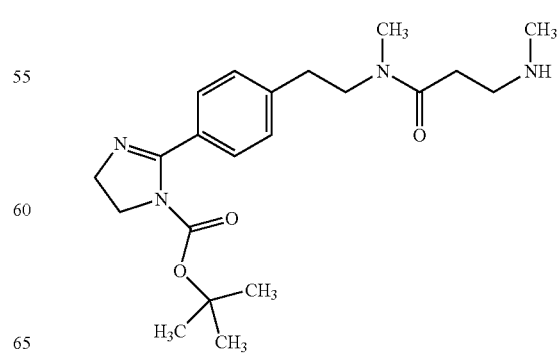

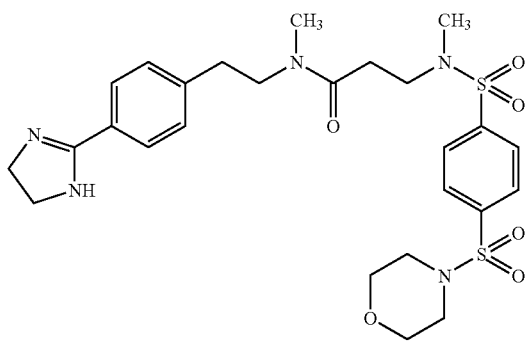

$C_{26}H_{35}N_5O_6S_2 \times C_2HF_3O_2$ (691.74) Yield: 51% of theory
Retention time (HPLC): 3.20 min

EXAMPLE 52

N-{2-[4-(4,5-Dihydro-1H-imidazol-2-yl)phenyl]ethyl}-N-methyl-3-[methyl-(3-nitrobenzenesulphonyl)amino]propionamide trifluoroacetate

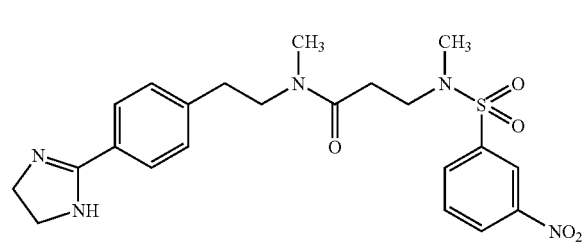

$C_{22}H_{27}N_5O_5S \times C_2HF_3O_2$ (587.57) Yield: 45% of theory
Retention time (HPLC): 3.23 min

EXAMPLE 53

N-{2-[4-(4,5-Dihydro-1H-imidazol-2-yl)phenyl]ethyl}-N-methyl-3-[methyl-(2-trifluoromethoxybenzenesulphonyl)amino]propionamide trifluoroacetate

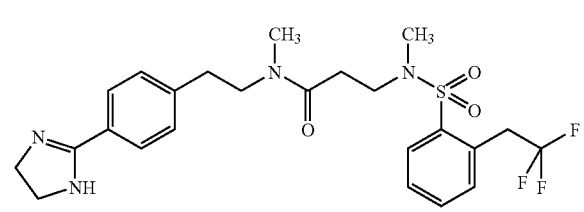

$C_{23}H_{27}F_3N_4O_4S \times C_2HF_3O_2$ (626.57) Yield: 74% of theory Retention time (HPLC): 3.39 min

EXAMPLE 54

3-[(Benz[1,2,5]oxadiazole-4-sulphonyl)methylamino]-N-{2-[4-(4,5-dihydro-1H-imidazol-2-yl)phenyl]ethyl}-N-methylpropionamide trifluoroacetate

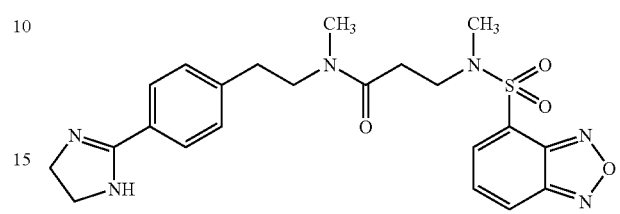

$C_{22}H_{26}N_6O_4S \times C_2HF_3O_2$ (584.57) Yield: 24% of theory
Retention time (HPLC): 3.15 min

EXAMPLE 55

3-[(2-Chloro-4-trifluoromethylbenzenesulphonyl)methylamino]-N-{2-[4-(4,5-dihydro-1H-imidazol-2-yl)phenyl]ethyl}-N-methylpropionamide trifluoroacetate

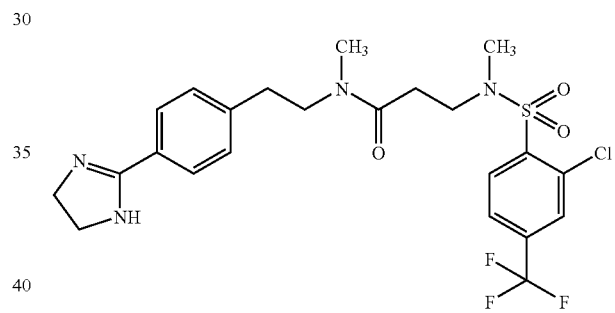

$C_{23}H_{26}ClF_3N_4O_3S \times C_2HF_3O_2$ (645.02) Yield: 50% of theory Retention time (HPLC): 3.55 min

EXAMPLE 56

3-[(4-Butoxybenzenesulphonyl)methylamino]-N-{2-[4-(4,5-dihydro-1H-imidazol-2-yl)phenyl]ethyl}-N-methylpropionamide trifluoroacetate

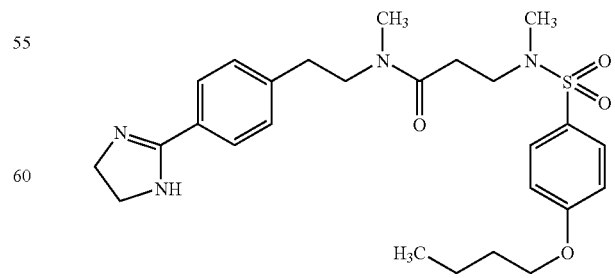

$C_{26}H_{36}N_4O_4S \times C_2HF_3O_2$ (614.68) Yield: 61% of theory
Retention time (HPLC): 3.64 min

EXAMPLE 57

3-[(3,4-Difluorobenzenesulphonyl)methylamino]-N-{2-[4-(4,5-dihydro-1H-imidazol-2-yl)phenyl]ethyl}-N-methylpropionamide trifluoroacetate

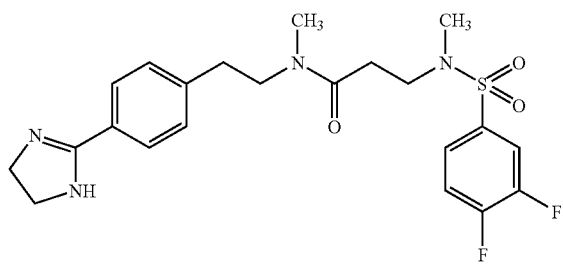

$C_{22}H_{26}F_2N_4O_3S \times C_2HF_3O_2$ (578.55) Yield: 62% of theory Retention time (HPLC): 3.28 min

EXAMPLE 58

3-[(3,5-Dichloro-4-hydroxybenzenesulphonyl)methylamino]-N-{2-[4-(4,5-dihydro-1H-imidazol-2-yl)phenyl]ethyl}-N-methylpropionamide trifluoroacetate

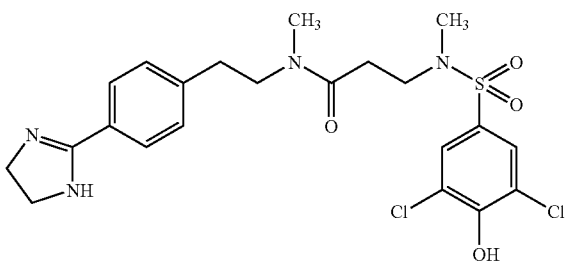

$C_{22}H_{26}Cl_2N_4O_4S \times C_2HF_3O_2$ (627.46) Yield: 53% of theory Retention time (HPLC): 3.22 min

EXAMPLE 59

N-{2-[4-(4,5-Dihydro-1H-imidazol-2-yl)phenyl]ethyl}-N-methyl-3-[methyl(naphthalene-1-sulphonyl)amino]propionamide trifluoroacetate

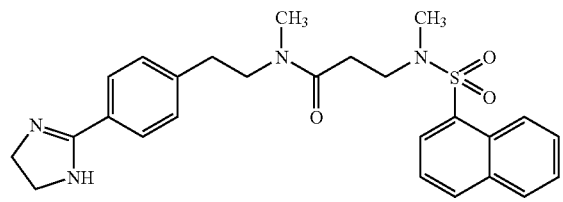

$C_{26}H_{30}N_4O_3S \times C_2HF_3O_2$ (592.63) Yield: 56% of theory Retention time (HPLC): 3.37 min

EXAMPLE 60

3-[(2,4-Dichlorobenzenesulphonyl)methylamino]-N-{2-[4-(4,5-dihydro-1H-imidazol-2-yl)phenyl]ethyl}-N-methylpropionamide trifluoroacetate

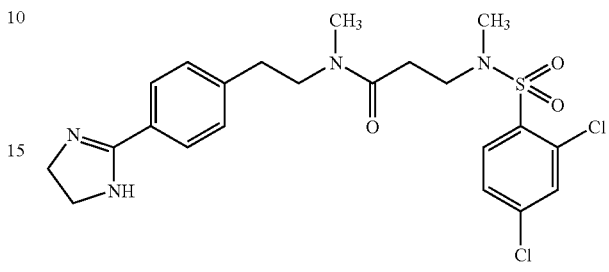

$C_{22}H_{26}Cl_2N_4O_3S \times C_2HF_3O_2$ (611.46) Yield: 72% of theory Retention time (HPLC): 3.42 min

EXAMPLE 61

N-{2-[4-(4,5-Dihydro-1H-imidazol-2-yl)phenyl]ethyl}-N-methyl-3-[methyl-(4-pentylbenzenesulphonyl)amino]propionamide trifluoroacetate

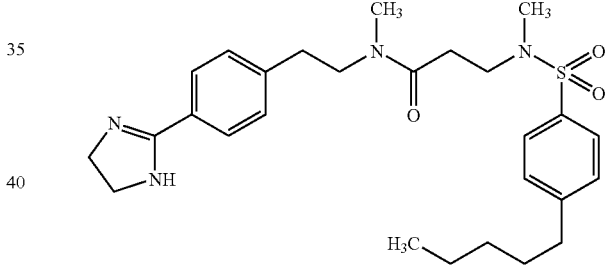

$C_{27}H_{38}N_4O_3S \times C_2HF_3O_2$ (612.71) Yield: 62% of theory Retention time (HPLC): 3.84 min

EXAMPLE 62

N-{2-[4-(4,5-Dihydro-1H-imidazol-2-yl)phenyl]ethyl}-3-[(3,5-dimethylbenzenesulphonyl)methylamino]-N-methylpropionamide trifluoroacetate

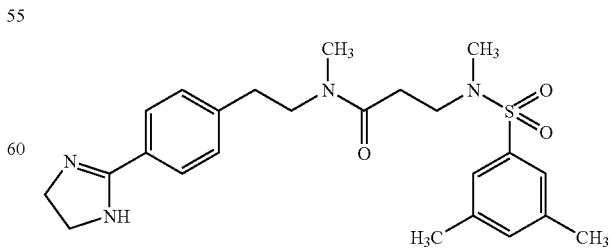

$C_{24}H_{32}N_4O_3S \times C_2HF_3O_2$ (570.63) Yield: 52% of theory Retention time (HPLC): 3.39 min

EXAMPLE 63

N-{2-[4-(4,5-Dihydro-1H-imidazol-2-yl)phenyl]ethyl}-N-methyl-3-(methylphenylmethanesulphonylamino)propionamide trifluoroacetate

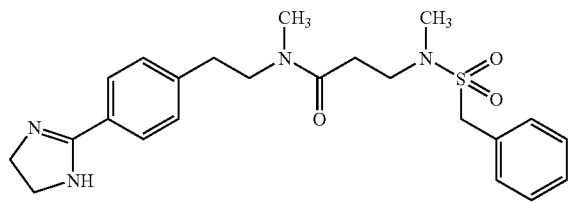

$C_{23}H_{30}N_4O_3S \times C_2HF_3O_2$ (556.60) Yield: 40% of theory Retention time (HPLC): 3.14 min

EXAMPLE 64

3-[(2-Chloro-4-fluorobenzenesulphonyl)methylamino]-N-{2-[4-(4,5-dihydro-1H-imidazol-2-yl)phenyl]ethyl}-N-methylpropionamide trifluoroacetate

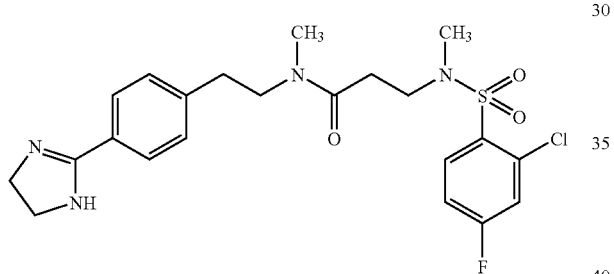

$C_{22}H_{26}ClFN_4O_3S \times C_2HF_3O_2$ (595.01) Yield: 63% of theory Retention time (HPLC): 3.29 min

EXAMPLE 65

3-[(2-Chloro-4-cyanobenzenesulphonyl)methylamino]-N-{2-[4-(4,5-dihydro-1H-imidazol-2-yl)phenyl]ethyl}-N-methylpropionamide trifluoroacetate

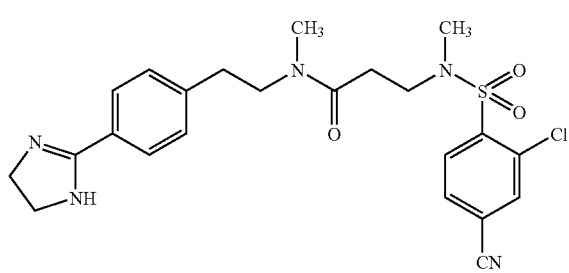

$C_{23}H_{26}ClN_5O_3S \times C_2HF_3O_2$ (602.03) Yield: 59% of theory Retention time (HPLC): 3.25 min

EXAMPLE 66

N-{2-[4-(4,5-Dihydro-1H-imidazol-2-yl)phenyl]ethyl}-3-[(3-methanesulphonylbenzenesulphonyl)methylamino]-N-methylpropionamide trifluoroacetate

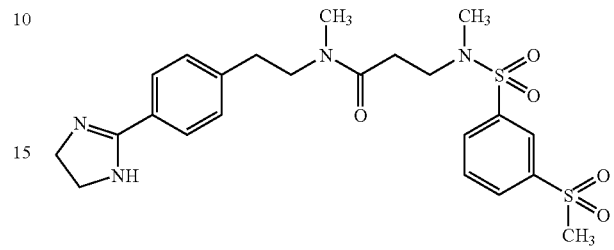

$C_{23}H_{30}N_4O_5S_2 \times C_2HF_3O_2$ (620.67) Yield: 72% of theory Retention time (HPLC): 3.01 min

EXAMPLE 67

3-[(Biphenyl-4-sulphonyl)methylamino]-N-{2-[4-(4,5-dihdro-1H-imidazol-2-yl)phenyl]ethyl}-N-methylpropionamide trifluoroacetate

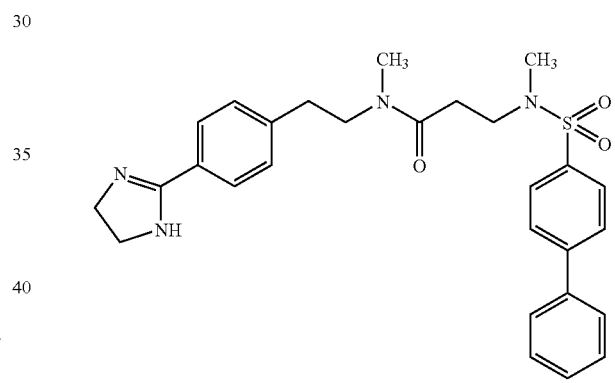

$C_{28}H_{32}N_4O_3S \times C_2HF_3O_2$ (618.67) Yield: 39% of theory Retention time (HPLC): 3.58 min

EXAMPLE 68

N-{2-[4-(4,5-Dihydro-1H-imidazol-2-yl)phenyl]ethyl}-3-[(5-fluoro-2-methylbenzenesulphonyl)methylamino]-N-methylpropionamide trifluoroacetate

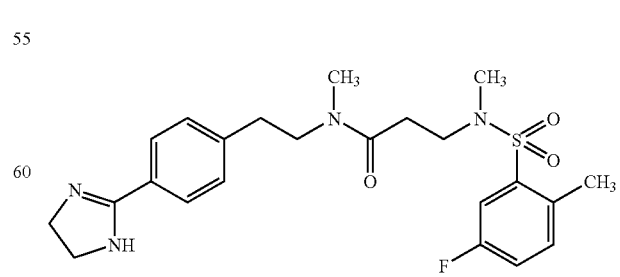

$C_{23}H_{29}FN_4O_3S \times C_2HF_3O_2$ (574.59) Yield: 61% of theory Retention time (HPLC): 3.28 min

EXAMPLE 69

N-{2-[4-(4,5-Dihydro-1H-imidazol-2-yl)phenyl]ethyl}-N-methyl-3-[methyl-(4-nitrobenzenesulphonyl)amino]propionamide trifluoroacetate

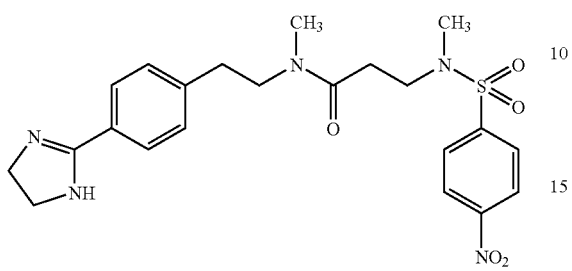

$C_{22}H_{27}N_5O_5S \times C_2HF_3O_2$ (587.57) Yield: 53% of theory Retention time (HPLC): 3.22 min

EXAMPLE 70

N-{2-[4-(4,5-Dihydro-1H-imidazol-2-yl)phenyl]ethyl}-3-{[4-(3,3-dimethyl-ureido)benzenesulphonyl]methylamino}-N-methylpropionamide trifluoroacetate

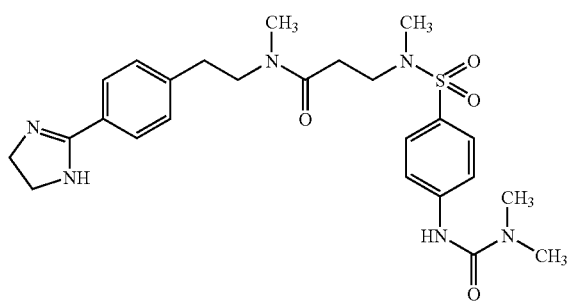

$C_{25}H_{34}N_6O_4S \times C_2HF_3O_2$ (628.67) Yield: 59% of theory Retention time (HPLC): 2.98 min

EXAMPLE 71

N-{2-[4-(4,5-Dihydro-1H-imidazol-2-yl)phenyl]ethyl}-N-methyl-3-[methyl-(4-trifluoromethylbenzenesulphonyl)amino]propionamide trifluoroacetate

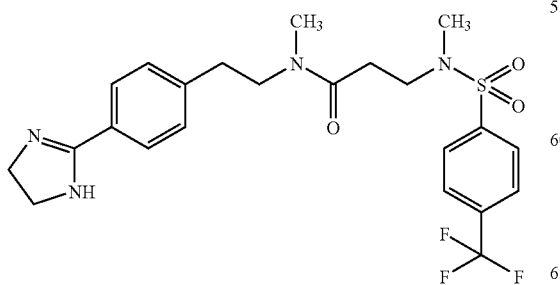

$C_{23}H_{27}F_3N_4O_3S \times C_2HF_3O_2$ (610.57) Yield: 61% of theory Retention time (HPLC): 3.46 min

EXAMPLE 72

N-{2-[4-(4,5-Dihydro-1H-imidazol-2-yl)phenyl]ethyl}-3-[(furan-2-sulphonyl)-methylamino]-N-methylpropionamide trifluoroacetate

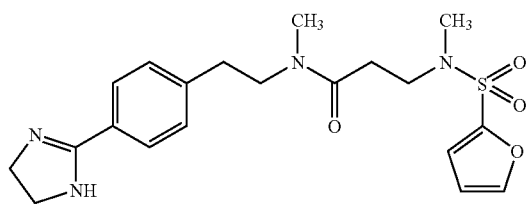

$C_{20}H_{26}N_4O_4S \times C_2HF_3O_2$ (532.54) Yield: 84% of theory Retention time (HPLC): 3.01 min

EXAMPLE 73

3-[(2-Chlorophenylmethanesulphonyl)methylamino]-N-{2-[4-(4,5-dihydro-1H-imidazol-2-yl)phenyl]ethyl}-N-methylpropionamide trifluoroacetate

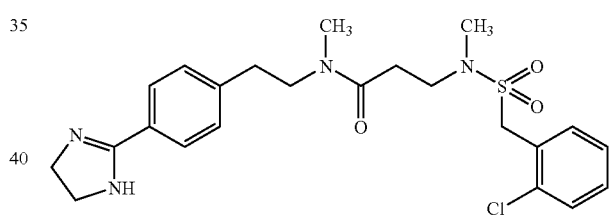

$C_{23}H_{29}ClN_4O_3S \times C_2HF_3O_2$ (591.05) Yield: 22% of theory Retention time (HPLC): 3.27 min

EXAMPLE 74

3-[(2,6-Dichlorobenzenesulphonyl)methylamino]-N-{2-[4-(4,5-dihydro-1H-imidazol-2-yl)phenyl]ethyl}-N-methylpropionamide trifluoroacetate

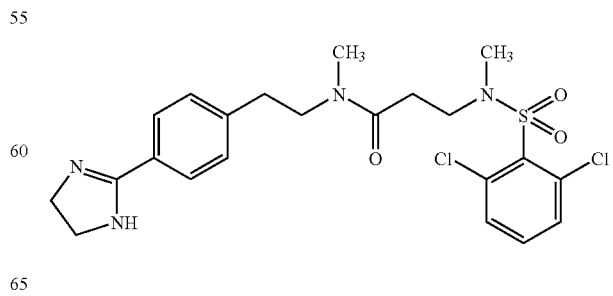

$C_{22}H_{26}Cl_2N_4O_3S \times C_2HF_3O_2$ (611.46) Yield: 63% of theory Retention time (HPLC): 3.30 min

EXAMPLE 75

N-{2-[4-(4,5-Dihydro-1H-imidazol-2-yl)phenyl]ethyl}-3-[(4-methoxy-2-nitrobenzenesulphonyl)methylamino]-N-methylpropionamide trifluoroacetate

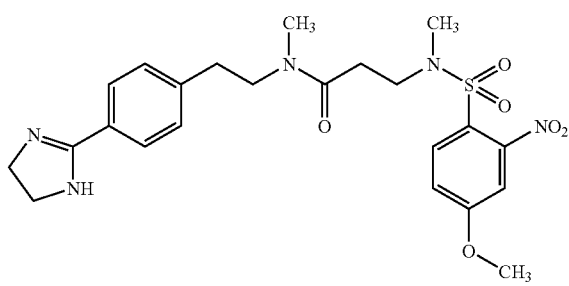

$C_{23}H_{29}N_5O_6S \times C_2HF_3O_2$ (617.60) Yield: 48% of theory
Retention time (HPLC): 3.26 min

EXAMPLE 76

N-{2-[4-(4,5-Dihydro-1H-imidazol-2-yl)phenyl]ethyl}-N-methyl-3-[methyl(thiophene-3-sulphonyl)amino]propionamide trifluoroacetate

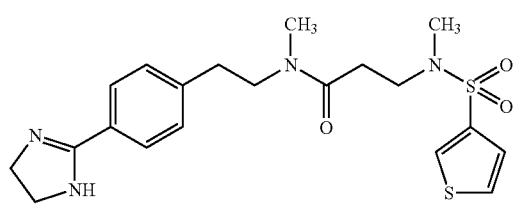

$C_{20}H_{26}N_4O_3S \times C_2HF_3O_2$ (548.60) Yield: 70% of theory
Retention time (HPLC): 3.03 min

EXAMPLE 77

3-[(Benzo[b]thiophene-3-sulphonyl)methylamino]-N-{2-[4-(4,5-dihydro-1H-imidazol-2-yl)phenyl]ethyl}-N-methylpropionamide trifluoroacetate

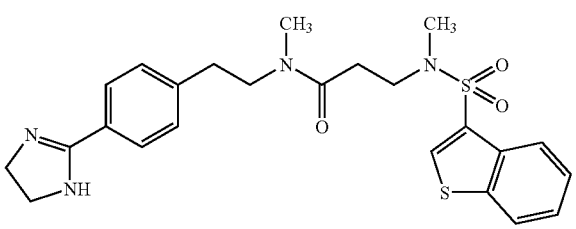

$C_{24}H_{28}N_4O_3S_2 \times C_2HF_3O_2$ (598.66) Yield: 52% of theory
Retention time (HPLC): 3.36 min

EXAMPLE 78

N-{2-[4-(4,5-Dihydro-1H-imidazol-2-yl)phenyl]ethyl}-3-[(5-dimethylaminonaphthalene-1-sulphonyl)methylamino]-N-methylpropionamide trifluoroacetate

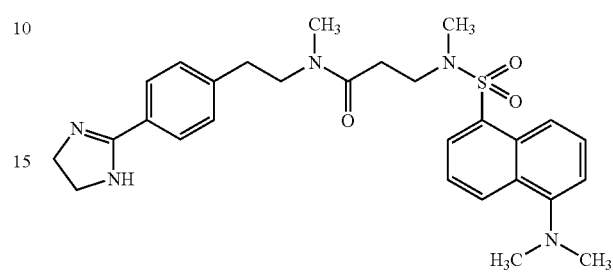

$C_{28}H_{35}N_5O_3S \times C_2HF_3O_2$ (635.70) Yield: 79% of theory
Retention time (HPLC): 3.09 min

EXAMPLE 79

N-{2-[4-(4,5-Dihydro-1H-imidazol-2-yl)phenyl]ethyl}-N-methyl-3-[methyl(toluene-2-sulphonyl)amino]propionamide trifluoroacetate

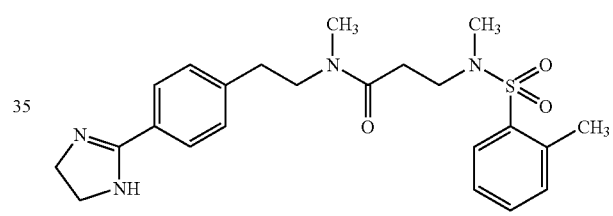

$C_{23}H_{30}N_4O_3S \times C_2HF_3O_2$ (556.60) Yield: 53% of theory
Retention time (HPLC): 3.22 min

EXAMPLE 80

N-{2-[4-(4,5-Dihydro-1H-imidazol-2-yl)phenyl]ethyl}-N-methyl-3-[methyl-(4-phenoxybenzenesulphonyl)amino]propionamide trifluoroacetate

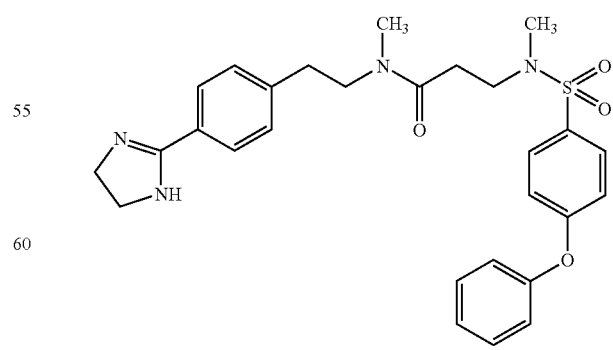

$C_{28}H_{32}N_4O_4S \times C_2HF_3O_2$ (634.67) Yield: 60% of theory
Retention time (HPLC): 3.61 min

EXAMPLE 81

3-[(2,4-Dichlorophenylmethanesulphonyl)methylamino]-N-{2-[4-(4,5-dihydro-1H-imidazol-2-yl)phenyl]ethyl}-N-methylpropionamide trifluoroacetate

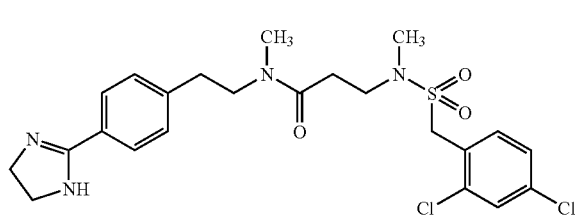

$C_{23}H_{28}Cl_2N_4O_3S \times C_2HF_3O_2$ (625.49) Yield: 25% of theory Retention time (HPLC): 3.46 min

EXAMPLE 82

N-{2-[4-(4,5-Dihydro-1H-imidazol-2-yl)phenyl]ethyl}-3-[(4-methoxy-2,3,6-trimethylbenzenesulphonyl)methylamino]-N-methylpropionamide trifluoroacetate

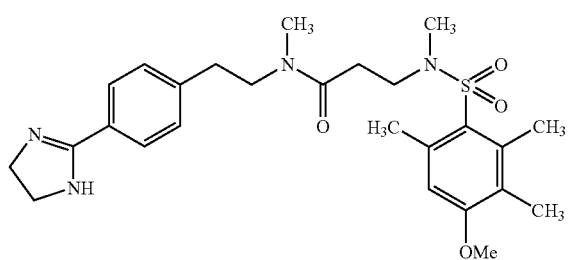

$C_{26}H_{36}N_4O_4S \times C_2HF_3O_2$ (614.68) Yield: 53% of theory Retention time (HPLC): 3.46 min

EXAMPLE 83

N-{2-[4-(4,5-Dihydro-1H-imidazol-2-yl)phenyl]ethyl}-N-methyl-3-[methyl-(4-nitro-3-trifluoromethylbenzenesulphonyl)amino]propionamide trifluoroacetate

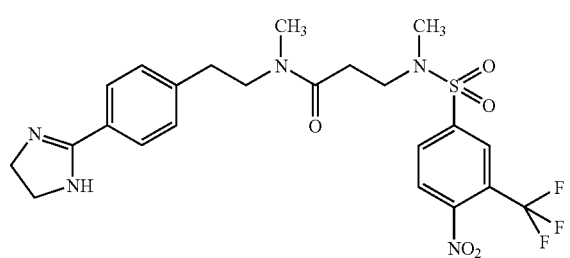

$C_{23}H_{26}F_3N_5O_5S \times C_2HF_3O_2$ (655.57) Yield: 60% of theory Retention time (HPLC): 3.53 min The following compounds were also prepared analogously to Example 41:

EXAMPLE 84

4-[(5-Chlorothiophene-2-sulphonyl)methylamino]-N-{2-[4-(4,5-dihydro-1H-imidazol-2-yl)phenyl]ethyl}-N-methylbutyramide trifluoroacetate

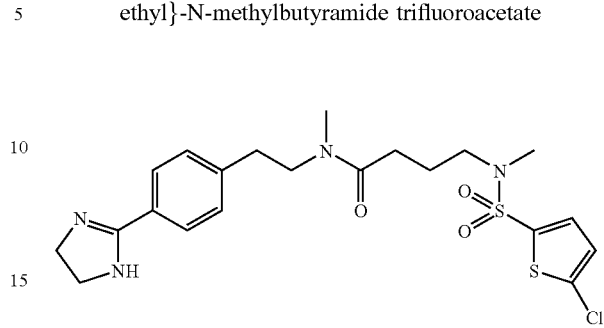

$C_{21}H_{27}ClN_4O_3S_2 \times C_2HF_3O_2$ (597.07) Yield: 22% of theory $^1$H-NMR (d$_6$-DMSO): δ=1.60/1.69 (2m, 2H, rotamers), 2.11/2.28 (2t, 2H, rotamers), 2.67/2.71 (2s, 3H, rotamers), 2.81/2.91 (2s, 3H, rotamers), 2.83-3.02 (m, 4H), 3.54 (m, 2H), 4.00 (s, 4H), 7.35 (d, 1H), 7.50-7.58 (m, 3H), 7.85/7.88 (2d, 2H, rotamers), 10.42 (s br, 1H) ppm

EXAMPLE 85

4-[(2-Chlorobenzenesulphonyl)methylamino]-N-{2-[4-(4,5-dihydro-1H-imidazol-2-yl)phenyl]ethyl}-N-methylbutyramide trifluoroacetate

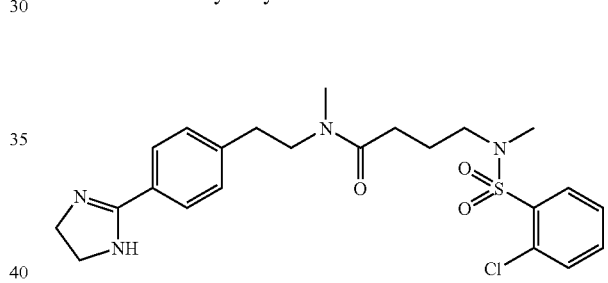

$C_{23}H_{29}ClN_4O_3S \times C_2HF_3O_2$ (591.04) Yield: 31% of theory $^1$H-NMR (d$_6$-DMSO): δ=1.60/1.69 (2m, 2H, rotamers), 2.08/2.22 (2t, 2H, rotamers), 2.77/2.81 (2s, 3H, rotamers), 2.80/2.88 (2s, 3H, rotamers), 2.83/2.94 (2t, 2H, rotamers), 3.10/3.18 (2t, 2H, rotamers), 3.52 (t, 2H), 4.00 (s, 4H), 7.50-7.58 (m, 3H), 7.67 (m, 2H), 7.85/7.87 (2d, 2H, rotamers), 7.94 (m, 1H), 10.42 (s br, 1H) ppm

EXAMPLE 86

N-{2-[4-(4,5-Dihydro-1H-imidazol-2-yl)phenyl]ethyl}-4-[(2,5-dimethylbenzenesulphonyl)methylamino]-N-methylbutyramide trifluoroacetate

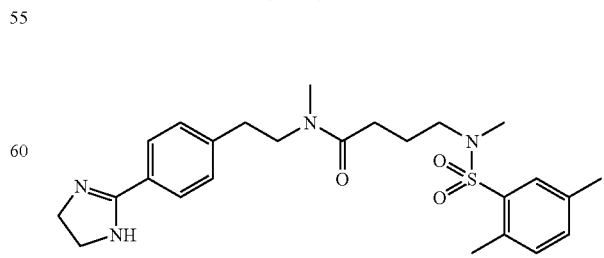

$C_{25}H_{34}N_4O_3S \times C_2HF_3O_2$ (584.65) Yield: 30% of theory $^1$H-NMR (d$_6$-DMSO): δ=1.60/1.68 (2m, 2H, rotamers), 2.08/2.22 (2t, 2H, rotamers), 2.34 (s, 3H), 2.46/2.47 (2s, 3H, rotamers), 2.69/2.73 (2s, 3H, rotamers), 2.80/2.88 (2s, 3H, rotamers), 2.85/2.94 (2t, 2H, rotamers), 3.03/3.10 (2t, 2H, rotamers), 3.52 (t, 2H), 4.00 (s, 4H), 7.31/7.36 (2d, 2H, rotamers), 7.49-7.58 (m, 3H), 7.85/7.88 (2d, 2H, rotamers), 10.42/10.43 (2s, 1H, rotamers) ppm

EXAMPLE 87

N-{2-[4-(4,5-Dihydro-1H-imidazol-2-yl)phenyl]ethyl}-4-[(1,2-dimethyl-1H-imidazole-4-sulphonyl)methylamino]-N-methylbutyramide tifluoroacetate

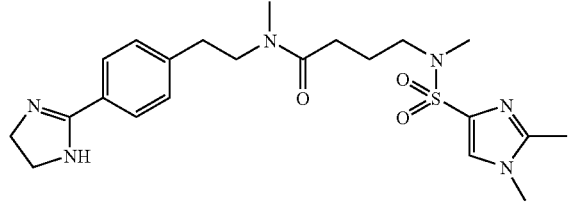

$C_{22}H_{32}N_6O_3S \times C_2HF_3O_2$ (574.62) Yield: 22% of theory $^1$H-NMR (d$_6$-DMSO): δ=1.57/1.67 (2m, 2H, rotamers), 2.09/2.27 (2t, 2H, rotamers), 2.30 (s, 3H), 2.61/2.65 (2s, 3H, rotamers), 2.81/2.91 (2s, 3H, rotamers), 2.83-3.00 (m, 4H), 3.60 (s, 3H), 4.00 (s, 4H), 7.53/7.58 (2d, 2H, rotamers), 7.68 (s, 1H), 7.85/7.88 (2d, 2H, rotamers), 10.41/10.44 (2s, 1H, rotamers) ppm

EXAMPLE 88

N-{2-[4-(4,5-Dihydro-1H-imidazol-2-yl)phenyl]ethyl}-4-[(4-methanesulphonylbenzenesulphonyl)methylamino]-N-methylbutyramide trifluoroacetate

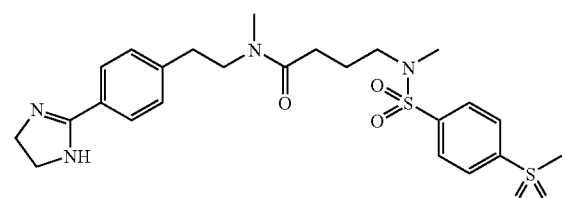

$C_{24}H_{32}N_4O_5S_2 \times C_2HF_3O_2$ (634.69) Yield: 32% of theory $^1$H-NMR (d$_6$-DMSO): δ=1.58/1.67 (2m, 2H, rotamers), 2.12/2.27 (2t, 2H, rotamers), 2.68/2.72 (2s, 3H, rotamers), 2.81/2.90 (2s, 3H, rotamers), 2.83-3.04 (m, 4H), 3.33 (s, 3H), 3.54 (m, 2H), 4.00 (s, 4H), 7.53/7.56 (2d, 2H, rotamers), 7.85/7.89 (2d, 2H, rotamers), 8.00/8.02 (2d, 2H, rotamers), 8.17 (d, 2H), 10.42/10.44 (2s, 1H, rotamers) ppm

EXAMPLE 89

4-[(3-Bromobenzenesulphonyl)methylamino]-N-{2-[4-(4,5-dihydro-1H-imidazol-2-yl)phenyl]ethyl}-N-methylbutyramide trifluoroacetate

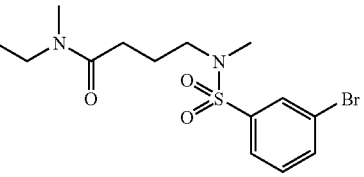

$C_{23}H_{29}BrN_4O_3S \times C_2HF_3O_2$ (635.50) Yield: 23% of theory $^1$H-NMR (d$_6$-DMSO): δ=1.57/1.66 (2m, 2H, rotamers), 2.11/2.26 (2t, 2H, rotamers), 2.65/2.68 (2s, 3H, rotamers), 2.81/2.91 (2s, 3H, rotamers), 2.83-3.01 (m, 4H), 3.54 (m, 2H), 4.00 (s, 4H), 7.50-7.63 (m, 3H), 7.76 (t, 1H), 7.83-7.95 (m, 4H), 10.41/10.43 (2s, 1H, rotamers) ppm

EXAMPLE 90

4-[(4-Bromo-5-chlorothiophene-2-sulphonyl)methylamino]-N-{2-[4-(4,5-dihydro-1H-imidazol-2-yl)phenyl]ethyl}-N-methylbutyramide trifluoroacetate $C_{21}H_{26}BrClN_4O_3S_2 \times C_2HF_3O_2$ (675.97) Yield: 27% of theory Retention time (HPLC): 3.51 min

EXAMPLE 91

4-[(3-Bromo-5-chlorothiophene-2-sulphonyl)methylamino]-N-{2-[4-(4,5-dihydro-1H-imidazol-2-yl)phenyl]ethyl}-N-methylbutyramide trifluoroacetate $C_{21}H_{26}BrClN_4O_3S_2 \times C_2HF_3O_2$ (675.97) Yield: 32% of theory Retention time (HPLC): 3.41 min

EXAMPLE 92

4-[(4,5-Dichlorothiophene-2-sulphonyl)methylamino]-N-{2-[4-(4,5-dihydro-1H-imidazol-2-yl)phenyl]ethyl}-N-methylbutyramide trifluoroacetate

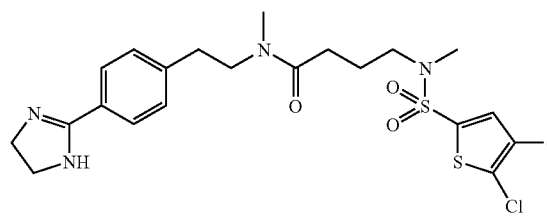

$C_{21}H_{26}Cl_2N_4O_3S_2 \times C_2HF_3O_2$ (631.52) Yield: 23% of theory Retention time (HPLC): 3.50 min

EXAMPLE 93

N-{2-[4-(4,5-Dihydro-1H-imidazol-2-yl)phenyl]ethyl}-4-[(2,4-dimethylthiazole-5-sulphonyl)methylamino]-N-methylbutyramide trifluoroaetate

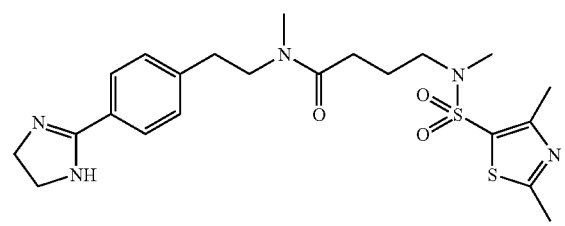

$C_{22}H_{31}N_5O_3S_2 \times C_2HF_3O_2$ (591.67) Yield: 19% of theory Retention time (HPLC): 2.97 min

EXAMPLE 94

4-[(5-Chloro-1,3-dimethyl-1H-pyrazole-4-sulphonyl)methylamino]-N-{2-[4-(4,5-dihydro-1H-imidazol-2-yl)phenyl]ethyl}-N-methylbutyramide trifluoroacetate

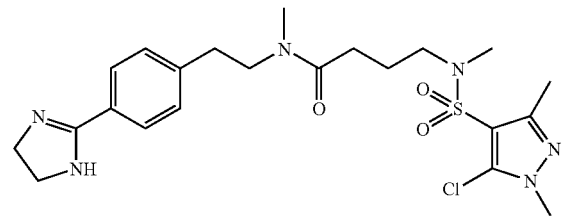

$C_{22}H_{31}ClN_6O_3S \times C_2HF_3O_2$ (609.07) Yield: 40% of theory Retention time (HPLC): 2.97 min

EXAMPLE 95

4-[(4-Amino-3,5-dichlorobenzenesulphonyl)methylamino]-N-{2-[4-(4,5-dihydro-1H-imidazol-2-yl)phenyl]ethyl}-N-methylbutyramide trifluoroatate

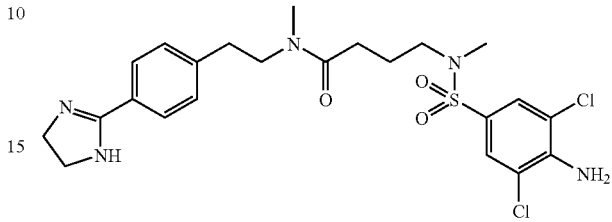

$C_{23}H_{29}Cl_2N_5O_3S \times C_2HF_3O_2$ (640.51) Yield: 38% of theory Retention time (HPLC): 3.21 min

EXAMPLE 96

N-{2-[4-(4,5-Dihydro-1H-imidazol-2-yl)phenyl]ethyl}-N-methyl-4-[methyl-(2,4,5-trichlorobenzenesulphonyl)amino]butyramide trifluoroacetate

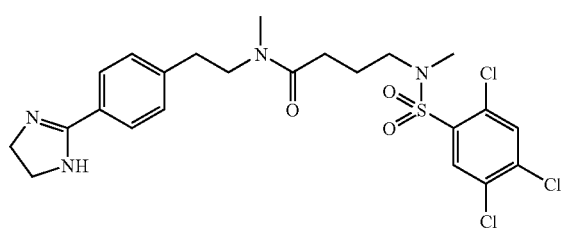

$C_{23}H_{27}Cl_3N_4O_3S \times C_2HF_3O_2$ (659.94) Yield: 25% of theory Retention time (HPLC): 3.51 min

EXAMPLE 97

4-[(2,5-Dichlorobenzenesulphonyl)methylamino]-N-{2-[4-(4,5-dihydro-1H-imidazol-2-yl)phenyl]ethyl}-N-methylbutyramide trifluoroacetate

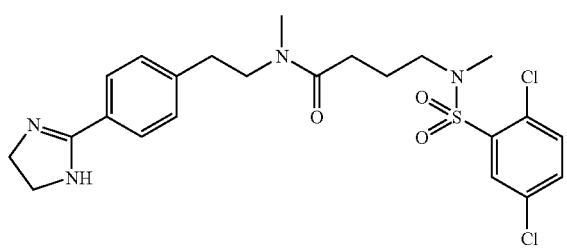

$C_{23}H_{28}Cl_2N_4O_3S \times C_2HF_3O_2$ (625.49) Yield: 32% of theory Retention time (HPLC): 3.32 min

EXAMPLE 98

4-[(3,4-Dichlorobenzenesulphonyl)methylamino]-N-{2-[4-(4,5-dihydro-1H-imidazol-2-yl)phenyl]ethyl}-N-methylbutyramide trifluoacetate

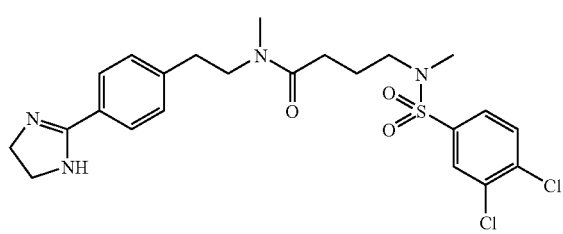

$C_{23}H_{28}Cl_2N_4O_3S \times C_2HF_3O_2$ (625.49) Yield: 26% of theory Retention time (HPLC): 3.42 min

EXAMPLE 99

4-[(4-Bromobenzenesulphonyl)methylamino]-N-{2-[4-(4,5-dihydro-1H-imidazol-2-yl)phenyl]ethyl}-N-methylbutyramide trifluorcetate

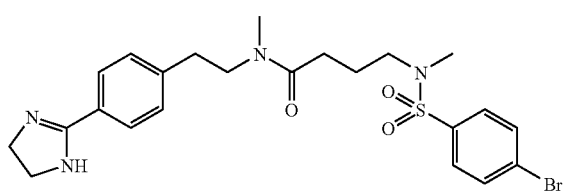

$C_{23}H_{29}BrN_4O_3S \times C_2HF_3O_2$ (635.50) Yield: 34% of theory Retention time (HPLC): 3.29 min

EXAMPLE 100

4-[(4-Fluorobenzenesulphonyl)methylamino]-N-{2-[4-(4,5-dihydro-1H-imidazol-2-yl)phenyl]ethyl}-N-methylbutyramide trifluoroacetate

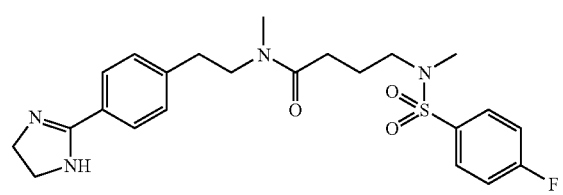

$C_{23}H_{29}FN_4O_3S \times C_2HF_3O_2$ (574.59) Yield: 30% of theory Retention time (HPLC): 3.11 min

EXAMPLE 101

4-[(3-Fluorobenzenesulphonyl)methylamino]-N-{2-[4-(4,5-dihydro-1H-imidazol-2-yl)phenyl]ethyl}-N-methylbutyramide trifluoroacetate

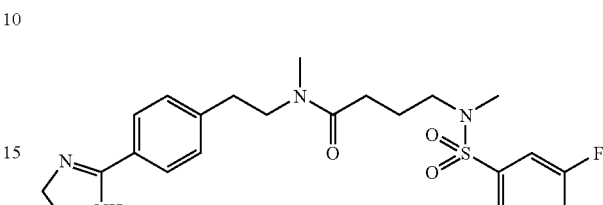

$C_{23}H_{29}FN_4O_3S \times C_2HF_3O_2$ (574.59) Yield: 33% of theory Retention time (HPLC): 3.14 min

EXAMPLE 102

4-[(4-Chlorobenzenesulphonyl)methylamino]-N-{2-[4-(4,5-dihydro-1H-imidazol-2-yl)phenyl]ethyl}-N-methylbutyramide trifluorocetate

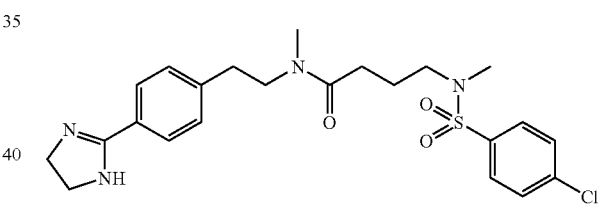

$C_{23}H_{29}ClN_4O_3S \times C_2HF_3O_2$ (591.05) Yield: 28% of theory Retention time (HPLC): 3.24 min

EXAMPLE 103

N-{2-[4-(4,5-Dihydro-1H-imidazol-2-yl)phenyl]ethyl}-N-methyl-4-[methyl-(2-trifluoromethylbenzenesulphonyl)amino]butyramide trifluoroacetate

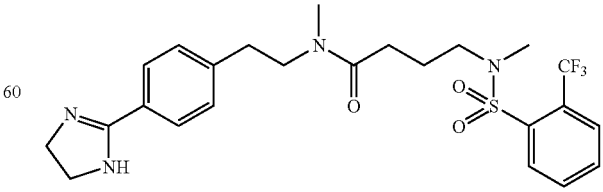

$C_{24}H_{29}F_3N_4O_3S \times C_2HF_3O_2$ (624.60) Yield: 36% of theory Retention time (HPLC): 3.24 min

EXAMPLE 104

4-[(5-Chloro-2-methoxybenzenesulphonyl)methylamino]-N-{2-[4-(4,5-dihydro-1H-imidazol-2-yl)phenyl]ethyl}-N-methylbutyramide trifluoroacetate

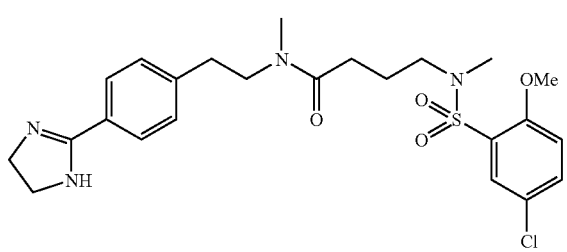

$C_{24}H_{31}ClN_4O_4S \times C_2HF_3O_2$ (621.07) Yield: 31% of theory Retention time (HPLC): 3.25 min

EXAMPLE 105

N-{2-[4-(4,5-Dihydro-1H-imidazol-2-yl)phenyl]ethyl}-N-methyl-4-[methyl(toluene-3-sulphonyl)amino]butyramide trifluoroacetate

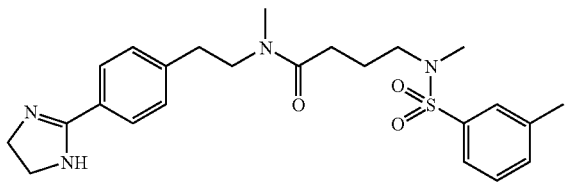

$C_{24}H_{32}N_4O_3S \times C_2HF_3O_2$ (570.63) Yield: 21% of theory Retention time (HPLC): 3.19 min

EXAMPLE 106

N-{2-[4-(4,5-Dihydro-1H-imidazol-2-yl)phenyl]ethyl}-4-[(4-methoxybenzenesulphonyl)methylamino]-N-methylbutyramide trifluoroacetate

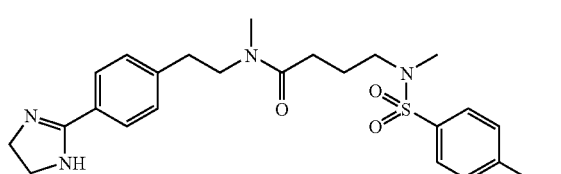

$C_{24}H_{32}FN_4O_4S \times C_2HF_3O_2$ (586.63) Yield: 32% of theory Retention time (HPLC): 3.10 min

EXAMPLE 107

4-[(4-Acetylamino-3-chlorobenzenesulphonyl)methylamino]-N-{2-[4-(4,5-dihydro-1H-imidazol-2-yl)phenyl]ethyl}-N-methylbutyramide trifluoroacetate

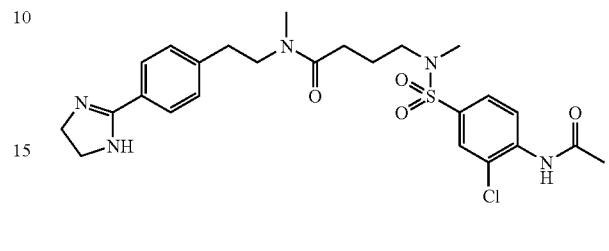

$C_{25}H_{32}ClN_5O_4S \times C_2HF_3O_2$ (648.10) Yield: 34% of theory Retention time (HPLC): 2.98 min

EXAMPLE 108

N-{2-[4-(4,5-Dihydro-1H-imidazol-2-yl)phenyl]ethyl}-4-[(2,5-dimethoxybenzenesulphonyl)methylamino]-N-methylbutyramide trifluoroacette

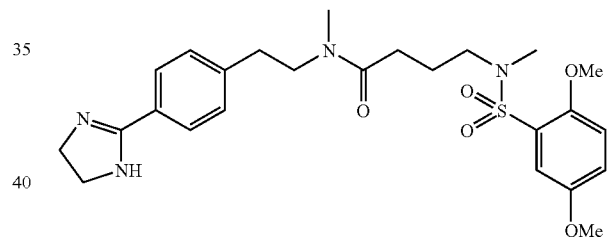

$C_{25}H_{34}N_4O_5S \times C_2HF_3O_2$ (616.65) Yield: 33% of theory Retention time (HPLC): 3.09 min

EXAMPLE 109

N-{2-[4-(4,5-Dihydro-1H-imidazol-2-yl)phenyl]ethyl}-4-[(3,4-dimethoxybenzenesulphonyl)methylamino]-N-methylbutyramide trifluoroacetate

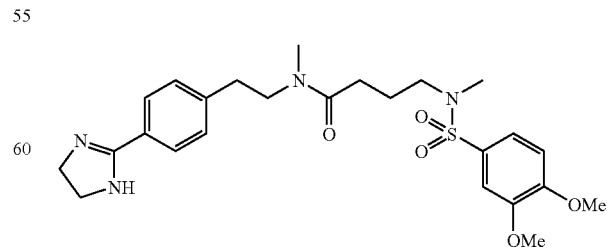

$C_{25}H_{34}N_4O_5S \times C_2HF_3O_2$ (616.65) Yield: 37% of theory Retention time (HPLC): 3.02 min

EXAMPLE 110

N-{2-[4-(4,5-Dihydro-1H-imidazol-2-yl)phenyl]ethyl}-N-methyl-4-[methyl-(2,4,6-trimethylbenzenesulphonyl)amino]butyramide trifluoroacetate

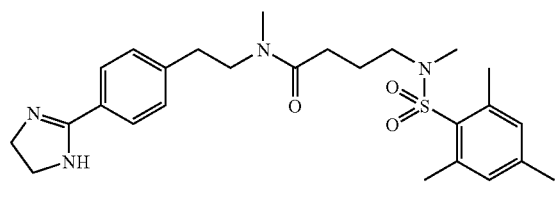

$C_{26}H_{36}N_4O_3S \times C_2HF_3O_2$ (598.68) Yield: 32% of theory
Retention time (HPLC): 3.37 min

EXAMPLE 111

N-{2-[4-(4,5-Dihydro-1H-imidazol-2-yl)phenyl]ethyl}-N-methyl-4-[methyl(naphthalene-2-sulphonyl)amino]butyramide trifluoroacetate

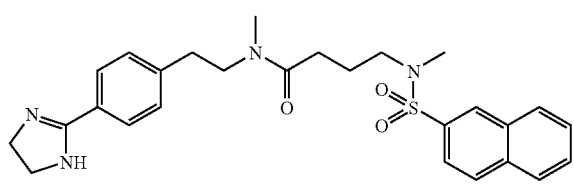

$C_{27}H_{32}N_4O_3S \times C_2HF_3O_2$ (606.66) Yield: 28% of theory
Retention time (HPLC): 3.35 min

EXAMPLE 112

N-{2-[4-(4,5-Dihydro-1H-imidazol-2-yl)phenyl]ethyl}-N-methyl-4-[methyl-(2,3,5,6-tetramethylbenzenesulphonyl)amino]butyramide trifluoroacetate

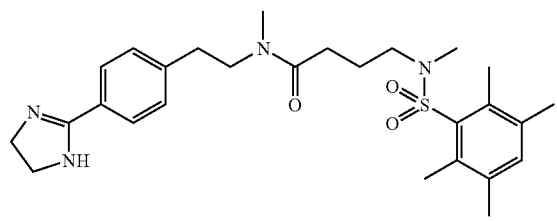

$C_{27}H_{38}N_4O_3S \times C_2HF_3O_2$ (612.71) Yield: 29% of theory
Retention time (HPLC): 3.46 min

EXAMPLE 113

N-{2-[4-(4,5-Dihydro-1H-imidazol-2-yl)phenyl]ethyl}-N-methyl-4-[methyl-(2-nitromethylbenzenesulphonyl)amino]butyramide trifluoroacetate

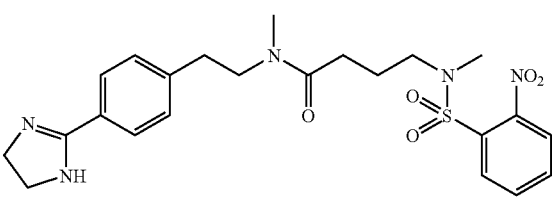

$C_{23}H_{29}N_5O_5S \times C_2HF_3O_2$ (601.60) Yield: 2% of theory
Retention time (HPLC): 3.11 min

EXAMPLE 114

4-[(4-Cyanobenzenesulphonyl)methylamino]-N-{2-[4-(4,5-dihydro-1H-imidazol-2-yl)phenyl]ethyl}-N-methylbutyramide trifluoroacetate

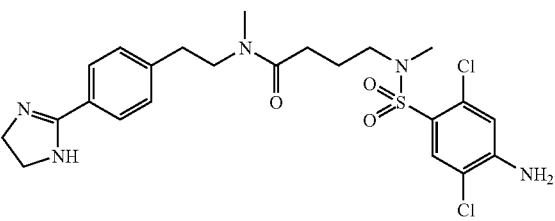

$C_{24}H_{29}N_5O_3S \times C_2HF_3O_2$ (581.61) Yield: 2% of theory
Retention time (HPLC): 3.06 min

EXAMPLE 115

4-[(4-Amino-2,5-dichlorobenzenesulphonyl)methylamino]-N-{2-[4-(4,5-dihydro-1H-imidazol-2-yl)phenyl]ethyl}-N-methylbutyramide trifluoroacetate $C_{23}H_{29}Cl_2N_5O_3S \times C_2HF_3O_2$ (640.51) Yield: 2% of theory
Retention time (HPLC): 3.15 min

EXAMPLE 116

4-[(4-tert.-Butylbenzenesulphonyl)methylamino]-N-{2-[4-(4,5-dihydro-1H-imidazol-2-yl)phenyl]ethyl}-N-methylbutyramide trifluorocetate

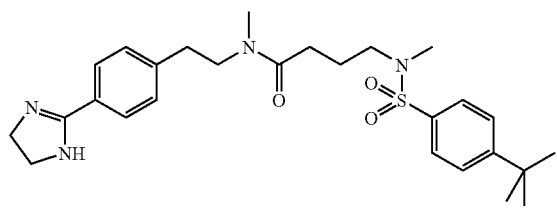

$C_{27}H_{38}N_4O_3S \times C_2HF_3O_2$ (612.71) Yield: 18% of theory Retention time (HPLC): 3.53 min

EXAMPLE 117

4-[(4-Butoxybenzenesulphonyl)methylamino]-N-{2-[4-(4,5-dihydro-1H-imidazol-2-yl)phenyl]ethyl}-N-methylbutyramide trifluoroacetate

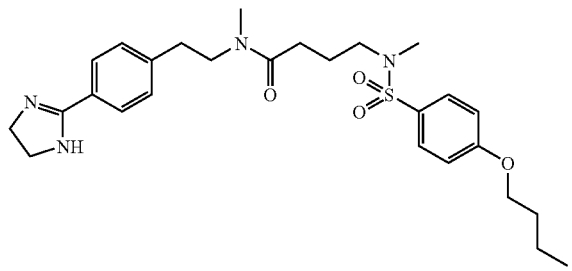

$C_{27}H_{38}N_4O_4S \times C_2HF_3O_2$ (628.71) Yield: 30% of theory Retention time (HPLC): 3.58 min

EXAMPLE 118

4-[(2,4-Dichlorobenzenesulphonyl)methylamino]-N-{2-[4-(4,5-dihydro-1H-imidazol-2-yl)phenyl]ethyl}-N-methylbutyramide trifluoroacetate

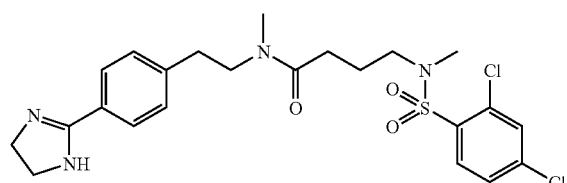

$C_{23}H_{28}Cl_2N_4O_3S \times C_2HF_3O_2$ (625.49) Yield: 27% of theory Retention time (HPLC): 3.37 min

EXAMPLE 119

4-[(2-Chloro-4-fluorobenzenesulphonyl)methylamino]-N-{2-[4-(4,5-dihydro-1H-imidazol-2-yl)phenyl]ethyl}-N-methylbutyramide trifluoroacetate

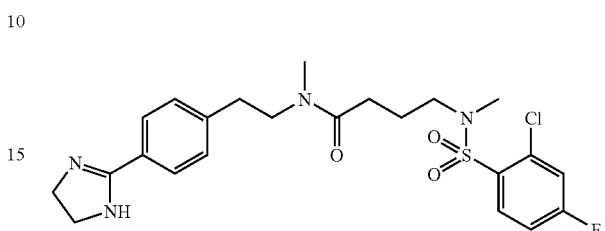

$C_{23}H_{28}ClFN_4O_3S \times C_2HF_3O_2$ (609.04) Yield: 21% of theory Retention time (HPLC): 3.22 min

EXAMPLE 120

N-{2-[4-(4,5-Dihydro-1H-imidazol-2-yl)phenyl]ethyl}-4-[(5-fluoro-2-methylbenzenesulphonyl)methylamino]-N-methylbutyraide trifluoroacetate

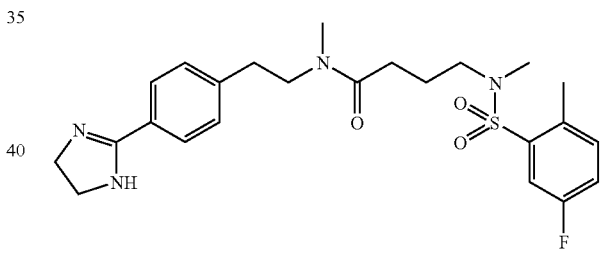

$C_{24}H_{31}FN_4O_3S \times C_2HF_3O_2$ (588.62) Yield: 25% of theory Retention time (HPLC): 3.22 min

EXAMPLE 121

N-{2-[4-(4,5-Dihydro-1H-imidazol-2-yl)phenyl]ethyl}-4-[(4-methoxy-2-nitrobenzenesulphonyl)methylamino]-N-methylbutyramide trifluoroacetate

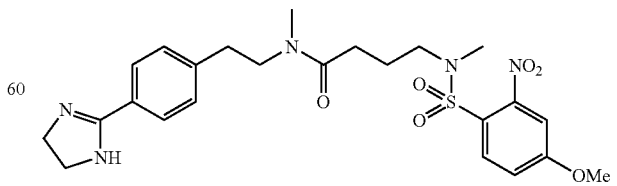

$C_{24}H_{31}N_5O_6S \times C_2HF_3O_2$ (631.62) Yield: 42% of theory Retention time (HPLC): 3.20 min

EXAMPLE 122

N-{2-[4-(4,5-Dihydro-1H-imidazol-2-yl)phenyl]ethyl}-N-methyl-4-[methyl(toluene-2-sulphonyl)amino]butyramide trifluoroacetate

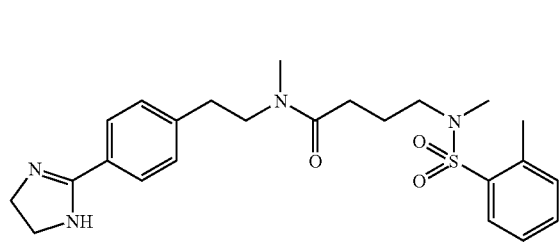

$C_{24}H_{32}N_4O_3S \times C_2HF_3O_2$ (570.63) Yield: 24% of theory Retention time (HPLC): 3.16 min

EXAMPLE 123

N-{2-[4-(4,5-Dihydro-1H-imidazol-2-yl)phenyl]ethyl}-4-[(4-methoxy-2,3,6-tri-methylbenzenesulphonyl)methylamino]-N-methylbutyramide trifluoroacetate

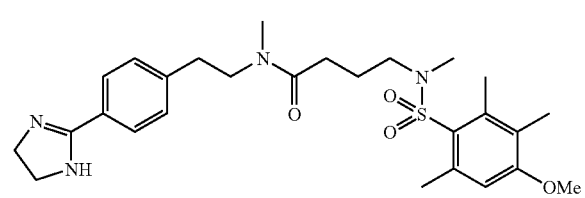

$C_{27}H_{38}N_4O_4S \times C_2HF_3O_2$ (628.71) Yield: 37% of theory Retention time (HPLC): 3.37 min

EXAMPLE 124

N-{2-[4-(4,5-Dihydro-1H-imidazol-2-yl)phenyl]ethyl}-N-methyl-4-[methyl-(4-propylbenzenesulphonyl)amino]butyramide trifluoroacetate

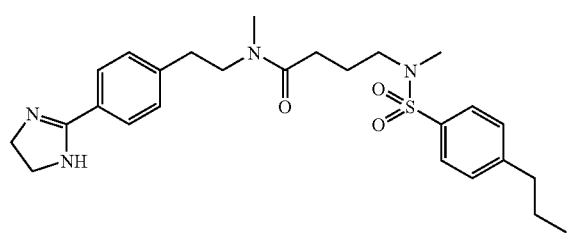

$C_{26}H_{36}N_4O_3S \times C_2HF_3O_2$ (598.68) Yield: 16% of theory Retention time (HPLC): 3.48 min

EXAMPLE 125

4-[(2,4-Dichloro-5-methylbenzenesulphonyl)methylamino]-N-{2-[4-(4,5-dihydro-1H-imidazol-2-yl)phenyl]ethyl}-N-methylbutyramide trifluoroacetate

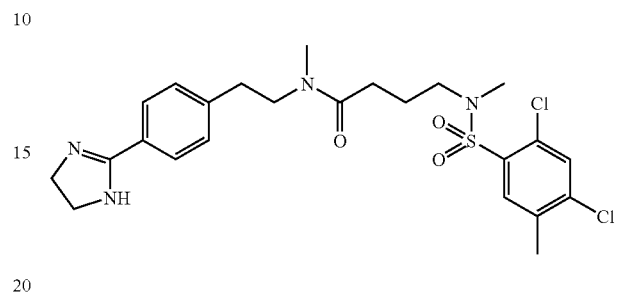

$C_{24}H_{30}Cl_2N_4O_3S \times C_2HF_3O_2$ (639.52) Yield: 37% of theory Retention time (HPLC): 3.45 min

EXAMPLE 126

4-[(3,4-Difluorobenzenesulphonyl)methylamino]-N-{2-[4-(4,5-dihydro-1H-imidazol-2-yl)phenyl]ethyl}-N-methylbutyramide trifluoroacetate

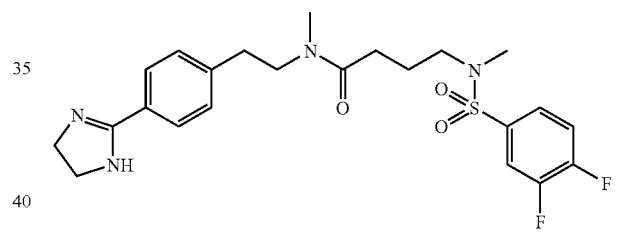

$C_{23}H_{28}F_2N_4O_3S \times C_2HF_3O_2$ (592.58) Yield: 19% of theory Retention time (HPLC): 3.21 min

EXAMPLE 127

N-{2-[4-(4,5-Dihydro-1H-imidazol-2-yl)phenyl]ethyl}-N-methyl-4-[methyl-(4-pentylbenzenesulphonyl)amino]butyramide trifluoroacetate

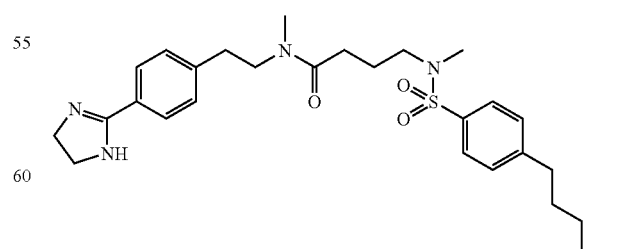

$C_{28}H_{40}N_4O_3S \times C_2HF_3O_2$ (626.74) Yield: 32% of theory Retention time (HPLC): 3.77 min

EXAMPLE 128

4-[(2-Chloro-4-cyanobenzenesulphonyl)methylamino]-N-{2-[4-(4,5-dihydro-1H-imidazol-2-yl)phenyl]ethyl}-N-methylbutyramide trifluoroacetate

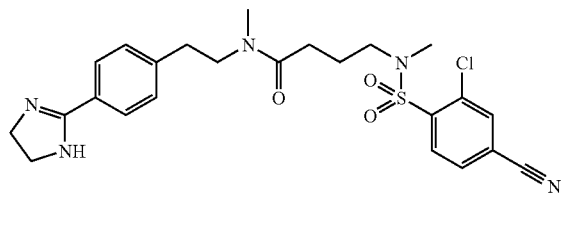

$C_{24}H_{28}ClN_5O_3S \times C_2HF_3O_2$ (616.06) Yield: 26% of theory Retention time (HPLC): 3.19 min

EXAMPLE 129

N-{2-[4-(4,5-Dihydro-1H-imidazol-2-yl)phenyl]ethyl}-N-methyl-4-[methyl-(4-nitromethylbenzenesulphonyl)amino]butyramide trifluoroacetate

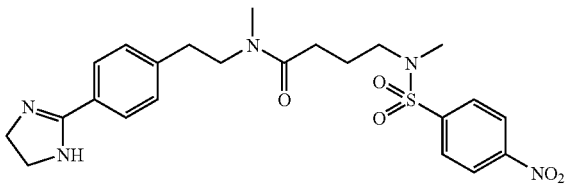

$C_{23}H_{29}N_5O_5S \times C_2HF_3O_2$ (601.60) Yield: 18% of theory Retention time (HPLC): 3.16 min

EXAMPLE 130

N-{2-[4-(4,5-Dihydro-1H-imidazol-2-yl)phenyl]ethyl}-4-[(furan-2-sulphonyl)methylamino]-N-methylbutyramide trifluoroacetate

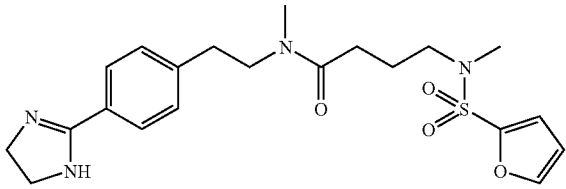

$C_{21}H_{28}N_4O_4S \times C_2HF_3O_2$ (546.56) Yield: 47% of theory Retention time (HPLC): 2.93 min

EXAMPLE 131

N-{2-[4-(4,5-Dihydro-1H-imidazol-2-yl)phenyl]ethyl}-4-[(furan-3-sulphonyl)methylamino]-N-methylbutyramide trifluoroacetate

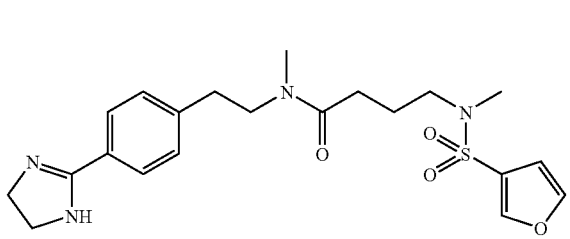

$C_{21}H_{28}N_4O_4S \times C_2HF_3O_2$ (546.56) Yield: 42% of theory Retention time (HPLC): 2.89 min

EXAMPLE 132

N-{2-[4-(4,5-Dihydro-1H-imidazol-2-yl)phenyl]ethyl}-4-[(thiophene-3-sulphonyl)methylamino]-N-methylbutyramide trifluoroacetate

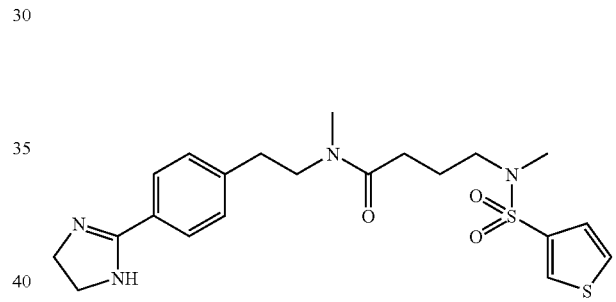

$C_{21}H_{28}N_4O_3S_2 \times C_2HF_3O_2$ (562.63) Yield: 23% of theory Retention time (HPLC): 2.95 min

EXAMPLE 133

N-{2-[4-(4,5-Dihydro-1H-imidazol-2-yl)phenyl]ethyl}-N-methyl-4-[methyl-(4-phenoxybenzenesulphonyl)amino]butyramide trifluoroacetate

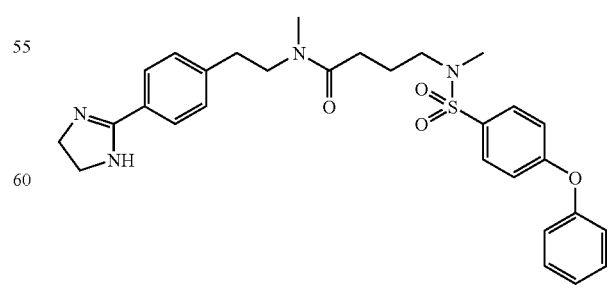

$C_{29}H_{34}N_4O_4S \times C_2HF_3O_2$ (648.70) Yield: 33% of theory Retention time (HPLC): 3.50 min

EXAMPLE 134

4-[(5-Chloronaphthalene-1-sulphonyl)methylamino]-N-{2-[4-(4,5-dihydro-1H-imidazol-2-yl)phenyl]ethyl}-N-methylbutyramide trifluoroacetate

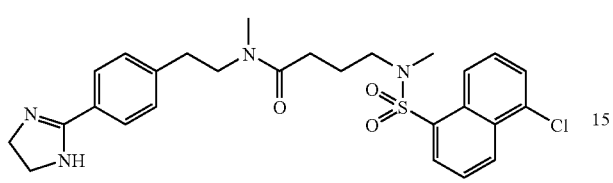

$C_{27}H_{31}ClN_4O_3S \times C_2HF_3O_2$ (641.11) Yield: 21% of theory Retention time (HPLC): 3.49 min

EXAMPLE 135

N-{2-[4-(4,5-Dihydro-1H-imidazol-2-yl)phenyl]ethyl}-N-methyl-4-{methyl-[4-(morpholine-4-sulphonyl)benzenesulphonyl]amino}butyramide trifluoroacetate

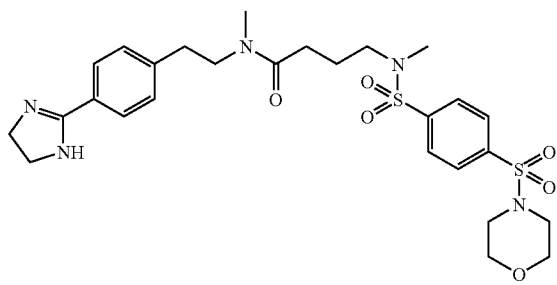

$C_{27}H_{37}N_5O_6S_2 \times C_2HF_3O_2$ (705.77) Yield: 45% of theory Retention time (HPLC): 3.09 min

EXAMPLE 136

4-[(2-Chloro-4-trifluoromethylbenzenesulphonyl)methylamino]-N-{2-[4-(4,5-dihydro-1H-imidazol-2-yl)phenyl]ethyl}-N-methylbutyramide trifluoroacetate

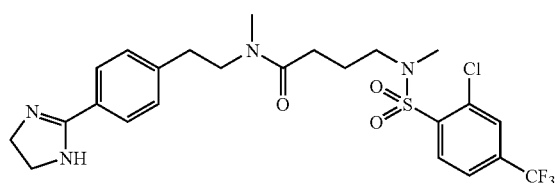

$C_{24}H_{28}ClF_3N_4O_3S \times C_2HF_3O_2$ (659.04) Yield: 31% of theory Retention time (HPLC): 3.45 min

EXAMPLE 137

4-[(3,5-Dichloro-4-hydroxybenzenesulphonyl)methylamino]-N-{2-[4-(4,5-dihydro-1H-imidazol-2-yl)phenyl]ethyl}-N-methylbutyramide trifluoroacetate

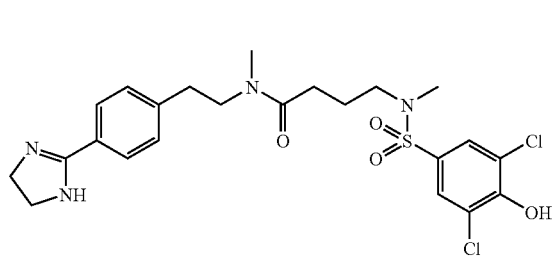

$C_{23}H_{28}Cl_2N_4O_4S \times C_2HF_3O_2$ (641.49) Yield: 28% of theory Retention time (HPLC): 3.11 min

EXAMPLE 138

N-{2-[4-(4,5-Dihydro-1H-imidazol-2-yl)phenyl]ethyl}-N-methyl-4-[methyl-(3,5-dimethylbenzenesulphonyl)amino]butyramide trifluoroacetate

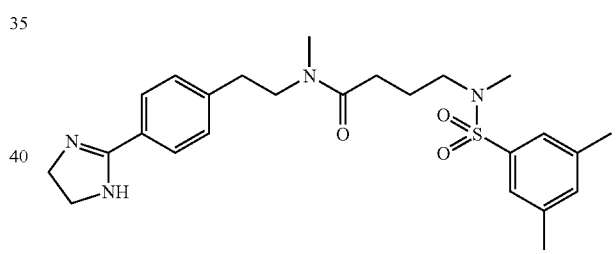

$C_{25}H_{34}N_4O_3S \times C_2HF_3O_2$ (584.66) Yield: 28% of theory Retention time (HPLC): 3.31 min

EXAMPLE 139

N-{2-[4-(4,5-Dihydro-1H-imidazol-2-yl)phenyl]ethyl}-4-[(3-methane-sulphonylbenzenesulphonyl)methylamino]-N-methylbutyramide trifluoroacetate

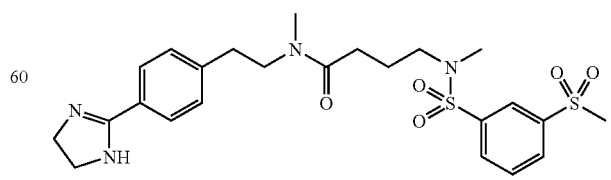

$C_{24}H_{32}N_4O_5S_2 \times C_2HF_3O_2$ (634.69) Yield: 22% of theory Retention time (HPLC): 2.91 min

EXAMPLE 140

N-{2-[4-(4,5-Dihydro-1H-imidazol-2-yl)phenyl]ethyl}-4-{[4-(3,3-dimethylurea)benzenesulphonyl]methylamino}-N-methylbutyramide trifluoroacetate

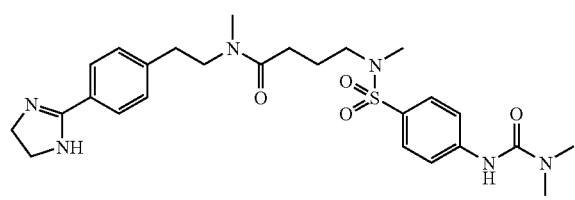

$C_{26}H_{36}N_6O_4S \times C_2HF_3O_2$ (642.69) Yield: 57% of theory Retention time (HPLC): 2.91 min

EXAMPLE 141

4-[(Benzo[b]thiophene-3-sulphonyl)methylamino]-N-{2-[4-(4,5-dihydro-1H-imidazol-2-yl)phenyl]ethyl}-N-methylbutyramide trifluoroacetate

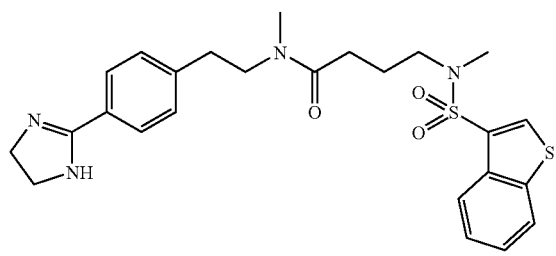

$C_{25}H_{30}N_4O_3S_2 \times C_2HF_3O_2$ (612.69) Yield: 35% of theory Retention time (HPLC): 3.31 min

EXAMPLE 142

N-{2-[4-(4,5-Dihydro-1H-imidazol-2-yl)phenyl]ethyl}-N-methyl-4-[methyl-(4-nitro-3-trifluoromethylbenzenesulphonyl)amino]butyramide trifluoroacetate

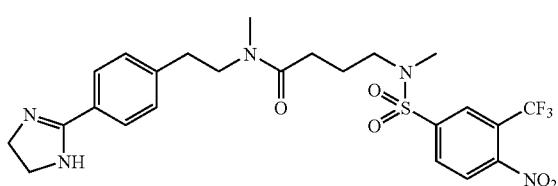

$C_{24}H_{28}F_3N_5O_5S \times C_2HF_3O_2$ (669.60) Yield: 23% of theory Retention time (HPLC): 3.41 min

EXAMPLE 143

4-[(4-Chloro-3-nitrobenzenesulphonyl)methylamino]-N-{2-[4-(4,5-dihydro-1H-imidazol-2-yl)phenyl]ethyl}-N-methylbutyramide trifluoroacetate

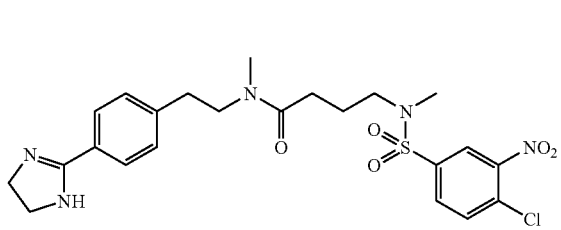

$C_{23}H_{28}ClN_5O_5S \times C_2HF_3O_2$ (636.04) Yield: 34% of theory Retention time (HPLC): 3.29 min

EXAMPLE 144

N-{2-[4-(4,5-Dihydro-1H-imidazol-2-yl)phenyl]ethyl}-N-methyl-4-[methyl(toluene-4-sulphonyl)amino]butyramide trifluoroacette

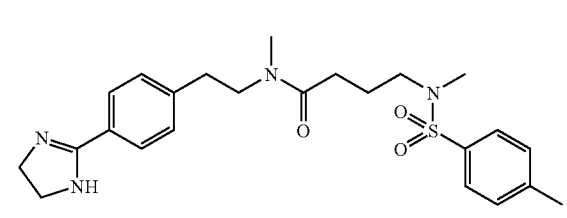

$C_{24}H_{32}N_4O_3S \times C_2HF_3O_2$ (570.63) Yield: 25% of theory Retention time (HPLC): 3.18 min

EXAMPLE 145

4-[(4-Acetylaminobenzenesulphonyl)methylamino]-N-{2-[4-(4,5-dihydro-1H-imidazol-2-yl)phenyl]ethyl}-N-methylbutyramide trifluoroacetate

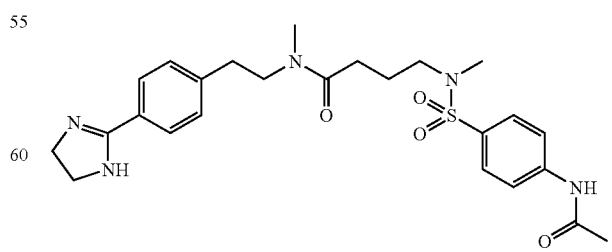

$C_{25}H_{33}N_5O_4S \times C_2HF_3O_2$ (613.65) Yield: 58% of theory Retention time (HPLC): 2.86 min

EXAMPLE 146

N-{2-[4-(4,5-Dihydro-1H-imidazol-2-yl)phenyl]ethyl}-N-methyl-4-[methyl-(3-nitromethylbenzenesulphonyl)amino]butyramide trifluoroacetate

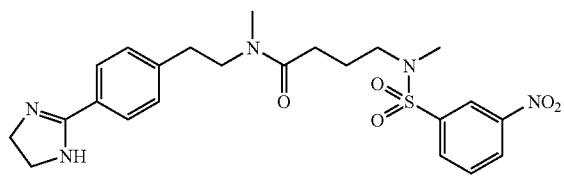

$C_{23}H_{29}N_5O_5S \times C_2HF_3O_2$ (601.60) Yield: 32% of theory
Retention time (HPLC): 3.12 min

EXAMPLE 147

4-(Benzenesulphonylmethylamino)-N-{2-[4-(4,5-dihydro-1H-imidazol-2-yl)phenyl]ethyl}-N-methylbutyramide trifluoroacetate

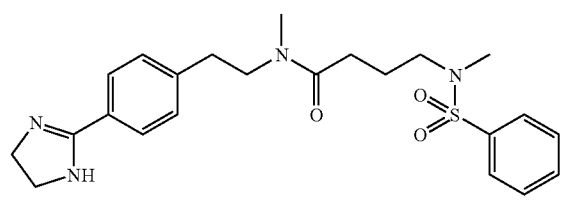

$C_{23}H_{30}N_4O_3S \times C_2HF_3O_2$ (556.60) Yield: 21% of theory
Retention time (HPLC): 3.04 min

EXAMPLE 148

N-{2-[4-(4,5-Dihydro-1H-imidazol-2-yl)phenyl]ethyl}-N-methyl-4-[methyl(naphthalene-1-sulphonyl)amino]butyramide trifluoroacetate

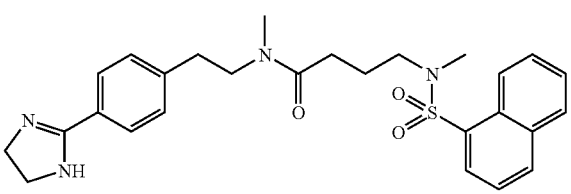

$C_{27}H_{32}N_4O_3S \times C_2HF_3O_2$ (606.66) Yield: 16% of theory
Retention time (HPLC): 3.27 min

EXAMPLE 149

4-(Biphenyl-4-sulphonylmethylamino)-N-{2-[4-(4,5-dihydro-1H-imidazol-2-yl)phenyl]ethyl}-N-methylbutyramide trifluoroacetate

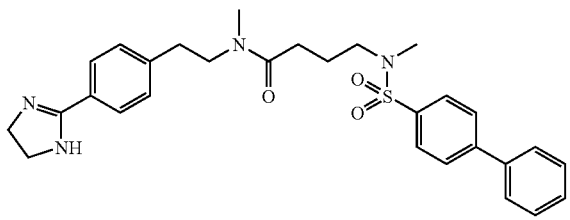

$C_{29}H_{34}N_4O_3S \times C_2HF_3O_2$ (632.70) Yield: 17% of theory
Retention time (HPLC): 3.50 min

EXAMPLE 150

N-{2-[4-(4,5-Dihydro-1H-imidazol-2-yl)phenyl]ethyl}-N-methyl-4-[methyl-(4-trifluoromethylbenzenesulphonyl)amino]butyramide trifluoroacetate

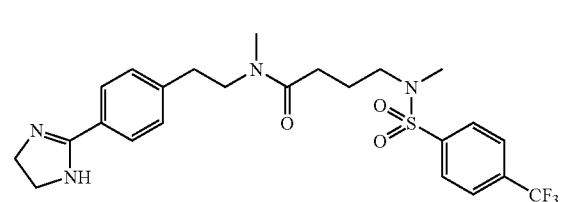

$C_{24}H_{29}F_3N_4O_3S \times C_2HF_3O_2$ (624.60) Yield: 27% of theory Retention time (HPLC): 3.35 min

EXAMPLE 151

4-[(2,6-Dichlorobenzenesulphonyl)methylamino]-N-{2-[4-(4,5-dihydro-1H-imidazol-2-yl)phenyl]ethyl}-N-methylbutyramide trifluoroacetate

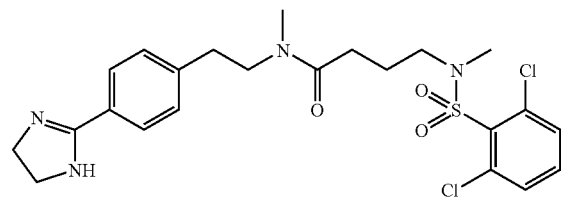

$C_{23}H_{28}Cl_2N_4O_3S \times C_2HF_3O_2$ (625.49) Yield: 28% of theory Retention time (HPLC): 3.21 min

EXAMPLE 152

N-{2-[4-(4,5-Dihydro-1H-imidazol-2-yl)phenyl]ethyl}-4-[(5-dimethylaminonaphthalene-1-sulphonyl)methylamino]-N-methylbutyramide trifluoroacetate

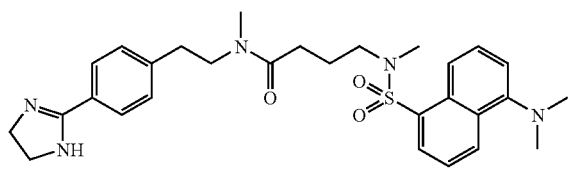

$C_{29}H_{37}N_5O_3S \times C_2HF_3O_2$ (649.73) Yield: 36% of theory
Retention time (HPLC): 3.00 min

EXAMPLE 153

N-{2-[4-(4,5-Dihydro-1H-imidazol-2-yl)phenyl]ethyl}-4-[(thiophene-2-sulphonyl)methylamino]-N-methylbutyramide trifluoroacetate

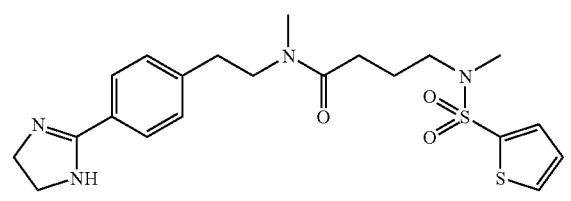

$C_{21}H_{28}N_4O_3S_2 \times C_2HF_3O_2$ (562.63) Yield: 39% of theory
Retention time (HPLC): 3.01 min

EXAMPLE 154

Methyl 3-(4-{[3-({2-[4-(4,5-dihydro-1H-imidazol-2-yl)phenyl]ethyl}methylcarbamoyl)propyl]methylsulphamoyl}phenyl)propionate trifluoroacetate

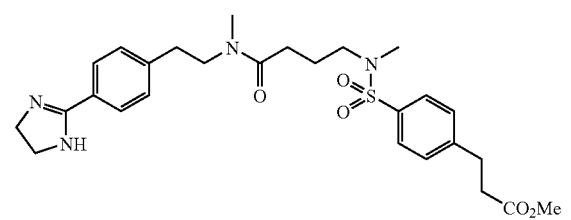

$C_{27}H_{36}N_4O_5S \times C_2HF_3O_2$ (642.69) Yield: 22% of theory
Retention time (HPLC): 3.16 min

EXAMPLE 155

N-{2-[4-(4,5-Dihydro-1H-imidazol-2-yl)phenyl]ethyl}-N-methyl-4-[methyl(pyridine-2-sulphonyl)amino]butyramide trifluoroacetate

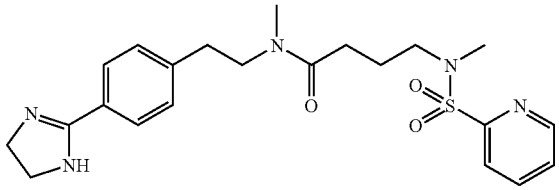

$C_{22}H_{29}N_5O_3S \times C_2HF_3O_2$ (557.59) Yield: 11% of theory
Retention time (HPLC): 2.81 min

EXAMPLE 156

4-[(3-Chloro-2-methylbenzenesulphonyl)methylamino]-N-{2-[4-(4,5-dihydro-1H-imidazol-2-yl)phenyl]ethyl}-N-methylbutyramide trfluoroacetate

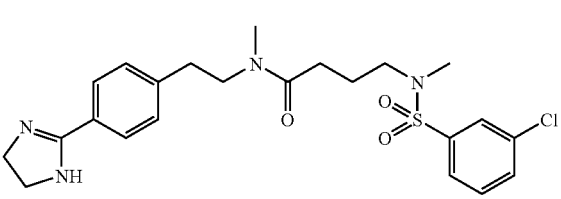

$C_{24}H_{31}ClN_4O_3S \times C_2HF_3O_2$ (605.07) Yield: 26% of theory Retention time (HPLC): 3.32 min

EXAMPLE 157

4-[(3-Chlorobenzenesulphonyl)methylamino]-N-{2-[4-(4,5-dihydro-1H-imidazol-2-yl)phenyl]ethyl}-N-methylbutyramide trifluoroacetate $C_{23}H_{29}ClN_4O_3S \times C_2HF_3O_2$ (591.05) Yield: 28% of theory Retention time (HPLC): 3.23 min

EXAMPLE 158

N-{2-[4-(4,5-Dihydro-1H-imidazol-2-yl)phenyl]ethyl}-N-methyl-4-[methyl-(3-trifluoromethylbenzenesulphonyl)amino]butyramide trifluoroacetate

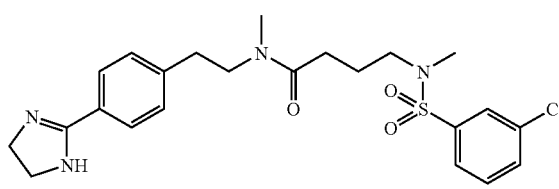

$C_{24}H_{29}F_3N_4O_3S \times C_2HF_3O_2$ (624.60) Yield: 30% of theory Retention time (HPLC): 3.32 min

EXAMPLE 159

N-{2-[4-(4,5-Dihydro-1H-imidazol-2-yl)phenyl]ethyl}-4-[(3,5-dimethylisoxazole-4-sulphonyl)methylamino]-N-methylbutyramide trifluoroacetate

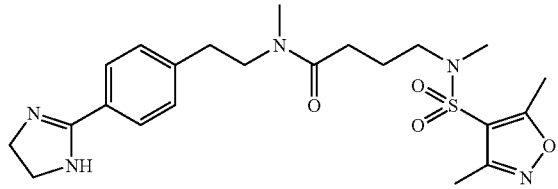

$C_{22}H_{31}N_5O_4S \times C_2HF_3O_2$ (575.60) Yield: 17% of theory Retention time (HPLC): 2.99 min

EXAMPLE 160

N-{2-[4-(4,5-Dihydro-1H-imidazol-2-yl)phenyl]ethyl}-N-methyl-4-[methyl-(1-methyl-1H-imidazole-4-sulphonyl)amino]butyramide trifluoroacetate

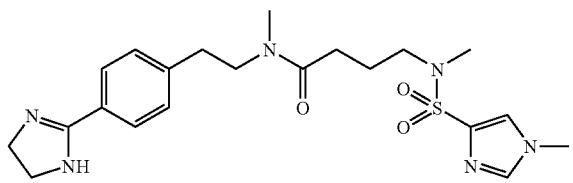

$C_{21}H_{30}N_6O_3S \times C_2HF_3O_2$ (560.59) Yield: 29% of theory Retention time (HPLC): 2.62 min

EXAMPLE 161

4-[(2,3-Dichlorobenzenesulphonyl)methylamino]-N-{2-[4-(4,5-dihydro-1H-imidazol-2-yl)phenyl]ethyl}-N-propylbutyramide

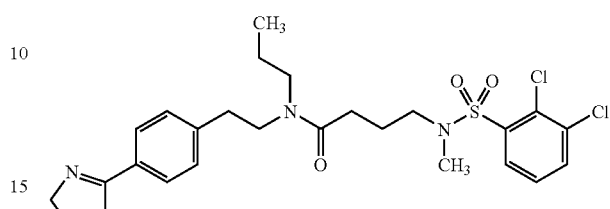

Prepared analogously to Example 13b from N-[2-(4-cyanophenyl)ethyl]-4-[(2,3-dichlorobenzenesulphonyl)methylamino]-N-propylbutyramide.

$C_{25}H_{32}Cl_2N_4O_3S$ (539.52) Yield: 48% of theory $[M+H]^+$= 539/541/543

EXAMPLE 162

4-[(2,3-Dichlorobenzenesulphonyl)methylamino]-N-{2-[4-(4,5-dihydro-1H-imidazol-2-yl)phenyl]ethyl}-N-isopropylbutyramide

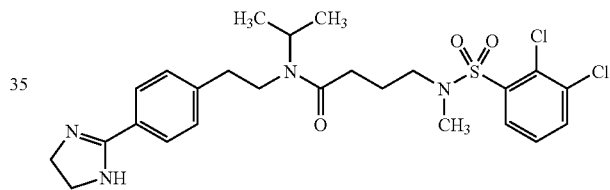

Prepared analogously to Example 13b from N-[2-(4-cyanophenyl)ethyl]-4-[(2,3-dichlorobenzenesulphonyl)methylamino]-N-isopropylbutyramide.

$C_{25}H_{32}Cl_2N_4O_3S$ (539.52) Yield: 28% of theory $[M+H]^+$= 539/541/543

EXAMPLE 163

4-[(2,3-Dichlorobenzenesulphonyl)methylamino]-N-{2-[4-(4,5-dihydro-1H-imidazol-2-yl)phenyl]ethyl}-N-(2,2,2-trifluoroethyl)butyramide

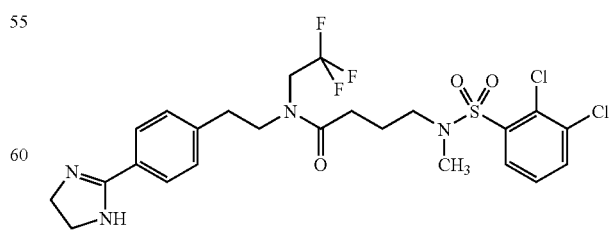

Prepared analogously to Example 13b from N-[2-(4-cyanophenyl)ethyl]-4-[(2,3-dichlorobenzenesulphonyl)methylamino]-N-(2,2,2-trifluoroethyl)butyramide.

$C_{24}H_{27}Cl_2F_3N_4O_3S$ (579.46) Yield: 53% of theory [M+H]$^+$=579/581/583

The following compounds can also be prepared analogously to the above-mentioned examples:

EXAMPLE 164

4-[(2,3-Dichlorobenzenesulphonyl)methylamino]-N-{2-[4-(4,5-dihydro-1H-imidazol-2-yl)phenyl]ethyl}-N-(2-fluoroethyl)butyramide

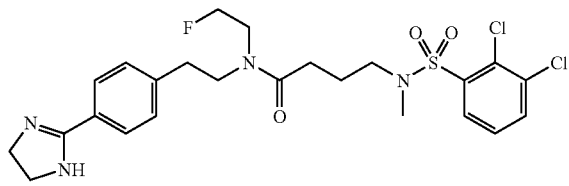

Prepared analogously to Example 13b) from N-[2-(4-cyanophenyl)ethyl]4-[(2,3-dichlorobenzenesulphonyl)methylamino]-N-(2-fluoroethyl)butyramide.
$C_{24}H_{25}Cl_2FN_4O_3S$ (543.48) [M+H]+=543/545/547

EXAMPLE 165

4-[(2,3-Dichlorobenzenesulphonyl)methylamino]-N-(2,2-difluoroethyl)-N-{2-[4-(4,5-dihydro-1H-imidazol-2-yl)phenyl]ethyl}butyramide

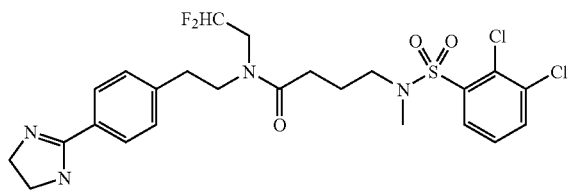

EXAMPLE 166

4-[(2,3-Dichlorobenzenesulphonyl)methylamino]-N-{2-[4-(4,5-dihydro-1H-imidazol-2-yl)phenyl]ethyl}-N-phenylbutyramide

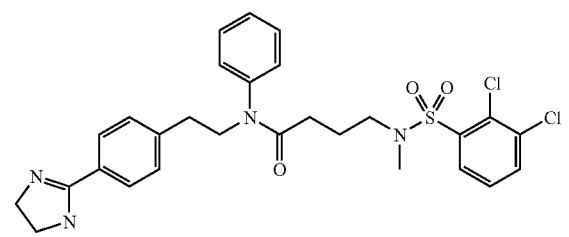

Prepared analogously to Example 13b) from N-[2-(4-cyanophenyl)ethyl]4-[(2,3-dichlorobenzenesulphonyl)methylamino]-N-phenylbutyramide.
$C_{28}H_{30}Cl_2N_4O_3S$ (573.53) [M+H]+=573/575/577

The examples below describe pharmaceutical administration forms comprising, as active compound, any compound of the formula I:

EXAMPLE I

Dry Ampoule with 75 mg of Active Compound per 10 ml

Composition:

| | |
|---|---|
| Active compound | 75.0 mg |
| Mannitol | 50.0 mg |
| Water for injection | ad 10.0 ml |

Production:

Active compound and mannitol are dissolved in water. The charged ampoules are freeze dried. Water for injection is used to dissolve to give the solution ready for use.

EXAMPLE II

Tablet with 50 mg of Active Compound

Composition:

| | |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 9 mm.

EXAMPLE III

Tablet with 350 mg of Active Compound

Composition:

| | |
|---|---|
| (1) Active compound | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 12 mm.

EXAMPLE IV

Capsule with 50 mg of Active Compound

Composition:

|     |                    |          |
| --- | ------------------ | -------- |
| (1) | Active compound    | 50.0 mg  |
| (2) | Maize starch dried | 58.0 mg  |
| (3) | Lactose powdered   | 50.0 mg  |
| (4) | Magnesium stearate | 2.0 mg   |
|     |                    | 160.0 mg |

Production:

(1) is triturated with (3). This trituration is added to the mixture of (2) and (4) with vigorous mixing.

This powder mixture is packed into hard gelatin two-piece capsules of size 3 in a capsule-filling machine.

EXAMPLE V

Capsule with 350 mg of Active Compound

Composition:

|     |                    |          |
| --- | ------------------ | -------- |
| (1) | Active compound    | 350.0 mg |
| (2) | Maize starch dried | 46.0 mg  |
| (3) | Lactose powdered   | 30.0 mg  |
| (4) | Magnesium stearate | 4.0 mg   |
|     |                    | 430.0 mg |

Production:

(1) is triturated with (3). This trituration is added to the mixture of (2) and (4) with vigorous stirring.

This powder mixture is packed into hard gelatin two-piece capsules of size 0 in a capsule-filling machine.

EXAMPLE VI

Suppositories with 100 mg of Active Compound 1 suppository comprises:

| Active compound                  | 100.0 mg  |
| -------------------------------- | --------- |
| Polyethylene glycol (M.W. 1500)  | 600.0 mg  |
| Polyethylene glycol (M.W. 6000)  | 460.0 mg  |
| Polyethylene sorbitan monostearate | 840.0 mg |
|                                  | 2000.0 mg |

What is claimed is:

1. A compound of the formula

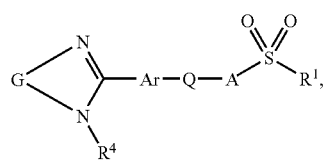

in which

R$^1$ is a phenyl, naphthyl or heteroaryl group, a phenyl-C$_{1-3}$-alkyl or C$_{3-7}$-cycloalkyl group, R$^4$ is a hydrogen atom or a C$_{1-6}$-alkyl group, G is the group —(CH$_2$)$_m$—, in which m is the number 2 or 3 and in which one to three hydrogen atoms independently of one another may be replaced by C$_{1-3}$-alkyl groups, Ar is a phenylene or heteroarylene group, Q is the group —(CH$_2$)$_p$—, in which p is the number 2 or 3 and in which one to three hydrogen atoms independently of one another may be replaced by C$_{1-3}$-alkyl groups, A is a group, attached via a nitrogen atom to the sulphonyl group in formula (I), of the formulae (IIa) to (IIi)

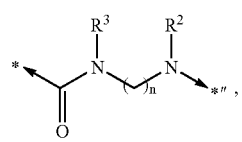

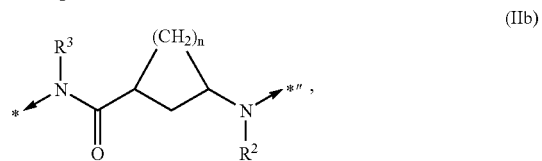

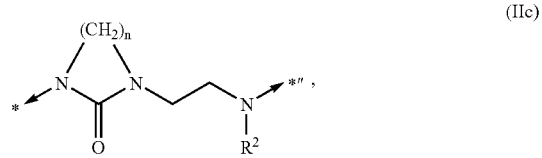

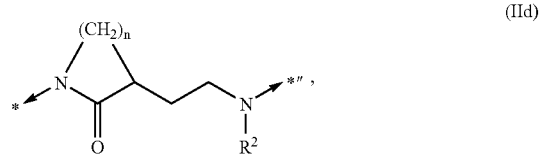

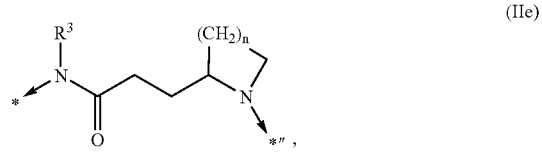

-continued

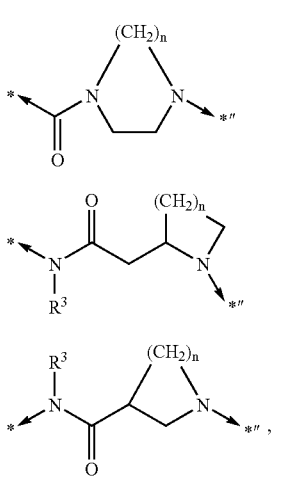

(IIg)

(IIh)

(IIi)

where the groups (IIa) to (IIi) are preferably attached to the sulphonyl group in formula (I) via the position marked *", n is the number 2 or 3, o is the number 1, 2 or 3, $R^2$ is a hydrogen atom, a $C_{1-6}$alkyl, $C_{2-5}$-alkenyl-methyl, $C_{2-5}$-alkynyl-methyl, $C_{3-7}$-cycloalkyl or a phenyl group and $R^3$ is a hydrogen atom, a phenyl, $C_{1-6}$-alkyl, $C_{2-5}$-alkenyl-methyl, $C_{2-5}$-alkynyl-methyl or $C_{3-7}$-cycloalkyl group or a group —$CH_2$—$CF_3$, —$CH_2$—$CHF_2$ or —$CH_2$—$CH_2F$, where the phenyl and phenylene groups present in the definitions mentioned above may be mono-, di-, tri- or tetrasubstituted by fluorine, chlorine, bromine or iodine atoms, by $C_{1-5}$-alkyl, trifluoromethyl, amino, $C_{1-3}$-alkylamino, di-($C_{1-3}$-alkyl)-amino, di-($C_{1-3}$-alkyl)-amino-carbonylamino, nitro, cyano, $C_{1-3}$-alkylcarbonyl, $C_{1-3}$-alkylsulphonyl, aminocarbonyl, $C_{1-3}$-alkylaminocarbonyl, di-($C_{1-3}$-alkyl)-aminocarbonyl, aminosulphonyl, $C_{1-3}$-alkylaminosulphonyl, di-($C_{1-3}$-alkyl)-aminosulphonyl, $C_{1-3}$-alkylcarbonylamino, carboxy-$C_{1-3}$-alkyl, $C_{1-3}$-alkyloxycarbonyl-$C_{1-3}$-alkyl, phenyl, phenyloxy, hydroxyl, $C_{1-4}$-alkyloxy, monofluoromethyloxy, difluoromethyloxy or trifluoromethyloxy groups or by N-pyrrolidinocarbonyl, N-pyrrolidinosulphonyl, N-piperidinocarbonyl or N-piperidinosulphonyl, where the methylene group present in the piperidine rings mentioned above may be replaced in the 4-position by O, S, SO, $SO_2$, NH or N($C_{1-3}$-alkyl), and the substituents may be identical or different, except for substitution by two, three or four nitro groups, where the naphthyl groups present in the definitions mentioned above may be mono- or disubstituted by fluorine, chlorine, bromine or iodine atoms, by $C_{1-3}$-alkyl, amino or di-($C_{1-3}$-alkyl)-amino groups and the substituents may be identical or different, where, unless indicated otherwise, a heteroaryl group mentioned above is a monocyclic 5-membered heteroaryl group attached via a carbon or nitrogen atom which contains an imino group which is optionally substituted by a $C_{1-3}$-alkyl, phenyl or phenyl-$C_{1-3}$-alkyl group, an oxygen or sulphur atom or an imino group which is optionally substituted by a $C_{1-3}$-alkyl, phenyl, amino-$C_{2-3}$-alkyl, $C_{1-3}$-alkylamino-$C_{2-3}$-alkyl or di-($C_{1-3}$-alkyl)-amino-$C_{2-3}$-alkyl group, by a 4- to 7-membered cycloalkyleneimino-$C_{1-3}$-alkyl or phenyl-$C_{1-3}$-alkyl group or an oxygen atom or sulphur atom and additionally a nitrogen atom or an imino group which is optionally substituted by a $C_{1-3}$-alkyl or phenyl-$C_{1-3}$-alkyl group and two or three nitrogen atoms, or a monocyclic 6-membered heteroaryl group which contains one, two or three nitrogen atoms, or a bicyclic 9-membered heteroaryl group consisting of one of the 5-membered heteroaryl groups mentioned above which is fused to one of the 6-membered heteroaryl groups mentioned above via two adjacent carbon atoms or a carbon and an adjacent nitrogen atom forming a bicycle, where the 5-membered heteroaryl group may also be replaced by a cyclopentadienyl group or the 6-membered heteroaryl group may also be replaced by a phenyl ring, or a bicyclic 10-membered heteroaryl group which consists of a phenyl ring and one of the 6-membered heteroaryl groups mentioned above or of two of the 6-membered heteroaryl groups mentioned above which are in each case condensed via two adjacent carbon atoms forming a bicycle, where the mono- and bicyclic heteroaryl groups mentioned above may additionally be mono-, di- or trisubstituted in the carbon skeleton by fluorine, chlorine, bromine or iodine atoms or by $C_{1-3}$-alkyl groups and where the substituents may be identical or different, and the term "heteroarylene group" mentioned above in the definitions is to be understood as meaning the mono- or bicyclic heteroaryl groups mentioned above which, however, are attached to the adjacent groups via two carbon atoms or via one carbon and one nitrogen atom, where the alkyl and alkoxy groups present in the definitions mentioned above which have more than two carbon atoms may, unless indicated otherwise, be straight-chain or branched, and where some or all of the hydrogen atoms of the methyl or ethyl groups present in the definitions mentioned above may be replaced by fluorine atoms, or a tautomer or a salt thereof.

2. A compound of the formula I according to claim 1 in which $R^1$ is a phenyl, naphthyl or heteroaryl group, a phenyl-$C_{1-3}$-alkyl or $C_{3-6}$-cycloalkyl group, $R^4$ is a hydrogen atom or a $C_{1-4}$-alkyl group, G is the group —$(CH_2)_m$—, in which m is the number 2 or 3 and in which one to three hydrogen atoms independently of one another may be replaced by $C_{1-3}$-alkyl groups, Ar is a phenylene group or a monocyclic 6-membered heteroarylene group or a monocyclic 5-membered heteroarylene group, attached via a carbon or nitrogen atom, Q is the group —$(CH_2)_p$—, in which p is the number 2 or 3 and in which one to three hydrogen atoms independently of one another may be replaced by $C_{1-3}$-alkyl groups, A is a group of the formula (IIa), (IIb), (IIc), (IId), (IIe), (IIf), (IIg), (IIh) or (IIi) attached via a nitrogen atom to the sulphonyl group in formula (I), where the groups (IIa) to (IIi) are preferably attached to the sulphonyl group in formula (I) via the position marked *" and n is the number 2 or 3, o is the number 1, 2 or 3, $R^2$ is a hydrogen atom, a $C_{1-4}$-alkyl, $C_{2-5}$-alkenylmethyl, $C_{3-6}$-cycloalkyl or a phenyl group and $R^3$ is a hydrogen atom, a $C_{1-4}$-alkyl, $C_{2-5}$-alkenylmethyl or $C_{3-6}$-cycloalkyl group or a $C_{1-3}$-alkyl group in which each methyl group may be substituted by up to three and each methylene group by up to two fluorine atoms, where the phenyl and phenylene groups present in the definitions mentioned above may be mono-, di-, tri- or tetrasubstituted by fluorine, chlorine or bromine atoms, by $C_{1-5}$-alkyl, trifluoromethyl, amino, $C_{1-3}$-alkylamino, di-($C_{1-3}$-alkyl)-amino, di-($C_{1-3}$-alkyl)-amino-carbonylamino, nitro, cyano, $C_{1-3}$-alkylcarbonyl, $C_{1-3}$-alkylsulphonyl, aminocarbonyl, $C_{1-3}$-alkylaminocarbonyl, di-($C_{1-3}$-alkyl)-aminocarbonyl, aminosulphonyl, $C_{1-3}$-alkylaminosulphonyl, di-($C_{1-3}$-alkyl)-aminosulphonyl, $C_{1-3}$-alkylcarbonylamino, phenyl, phenyloxy, hydroxyl, $C_{1-4}$-alkyloxy, monofluoromethyloxy, difluoromethyloxy or trifluoromethyloxy groups or by N-pyrrolidinocarbonyl, N-pyrrolidinosulphonyl, N-piperidinocarbonyl or N-piperidinosulphonyl, where the methylene group present in the piperidine rings mentioned above may be replaced in the 4-position by O, S, SO, $SO_2$, NH or N($C_{1-3}$-alkyl), and the substituents may be identical or different, except for substitution by two, three or four nitro groups, where the naphthyl groups present in the definitions mentioned above may be mono- or disubstituted by fluorine, chlorine or bromine atoms, by $C_{1-3}$-alkyl, amino or di-($C_{1-3}$-alkyl)-amino groups and the substituents may be identical or different, where, unless indicated otherwise, a heteroaryl group mentioned above is a monocyclic 5-membered heteroaryl group attached via a carbon or nitrogen atom which contains an imino group which is optionally substituted by a $C_{1-3}$-alkyl, phenyl or phenyl-$C_{1-3}$-alkyl group, an oxygen or sulphur atom or an imino group which is optionally substituted by a $C_{1-3}$-alkyl or phenyl group, by a 5- to 7-membered cycloalkyleneimino-$C_{1-3}$-alkyl or phenyl-$C_{1-3}$-alkyl group or an oxygen atom or sulphur atom and additionally a nitrogen atom or an imino group which is optionally substituted by a $C_{1-3}$-alkyl or phenyl-$C_{1-3}$-alkyl group and additionally two nitrogen atoms, or a monocyclic 6-membered heteroaryl group which contains one or two nitrogen atoms, or a bicyclic 9-membered heteroaryl group consisting of one of the 5-membered heteroaryl groups mentioned above which is fused to one of the 6-membered heteroaryl groups mentioned above via two adjacent carbon atoms or a carbon and an adjacent nitrogen atom forming a bicycle, where the 5-membered heteroaryl group may also be replaced by a cyclopentadienyl group or the 6-membered heteroaryl group may also be replaced by a phenyl ring, or a bicyclic 10-membered heteroaryl group which consists of a phenyl ring and one of the 6-membered heteroaryl groups mentioned above or of two of the 6-membered heteroaryl groups mentioned above which are in each case condensed via two adjacent carbon atoms forming a bicycle, where the mono- and bicyclic heteroaryl groups mentioned above may additionally be mono-, di- or trisubstituted in the carbon skeleton by fluorine, chlorine or bromine atoms or by $C_{1-3}$-alkyl groups and where the substituents may be identical or different, and the term "heteroarylene group" mentioned above in the definitions is to be understood as meaning the mono- or bicyclic heteroaryl groups mentioned above which, however, are attached to the adjacent groups via two carbon atoms or via one carbon and one nitrogen atom, where the alkyl and alkoxy groups present in the definitions mentioned above which have more than two carbon atoms may, unless indicated otherwise, be straight-chain or branched, and where some or all of the hydrogen atoms of the methyl or ethyl groups present in the definitions mentioned above may be replaced by fluorine atoms, or a tautomer or a salt thereof.

3. A compound of the formula I according to claim 1 in which $R^1$ is a phenyl or phenylmethyl group which is optionally mono-, di- or trisubstituted by fluorine, chlorine or bromine atoms, nitro, cyano, $C_{1-3}$-alkylsulphonyl, $C_{1-5}$-alkyl, trifluoromethyl, hydroxyl, $C_{1-5}$-alkyloxy, trifluoromethoxy, phenyloxy, morpholin-4-ylsulphonyl, phenyl, dimethylaminocarbonylamino, amino, methylcarbonylamino, dimethylamino, carboxy-$C_{1-3}$-alkyl or $C_{1-3}$-alkyloxycarbonyl-$C_{1-3}$-alkyl groups, where the substituents may be identical or different and polysubstitution by two or three nitro groups is excluded, a phenyl group which is optionally tetrasubstituted by fluorine, chlorine or bromine atoms, cyano, $C_{1-3}$-alkyl, trifluoromethyl, $C_{1-3}$-alkyloxy or trifluoromethoxy groups, where the substituents may be identical or different, a benzo[b]thiophenyl, quinolinyl, naphthyl, benz[1,2,5]oxadiazolyl, furanyl, thiophenyl, imidazolyl, thiazolyl, pyrazolyl, pyridinyl or isoxazolyl group which is optionally mono-, di- or trisubstituted by chlorine or bromine atoms or methyl, amino, methylamino or dimethylamino groups or a $C_{3-6}$-cycloalkyl group, for example the cyclopropyl group, $R^4$ is a hydrogen atom or a methyl group, G is the group —$(CH_2)_m$— in which m is the number 2 or 3 or the group —$(CH_2)_m$— in which m is the number 2 or 3 and in which one, two or three hydrogen atoms independently of one another are replaced by methyl or ethyl groups, Ar is a phenylene group, Q is the group —$(CH_2)_p$— in which p is the number 2 or the group —$(CH_2)_p$— in which p is the number 2 and in which one or two hydrogen atoms independently of one another are replaced by methyl or ethyl groups, A is a group of the formula (IIa), (IIb), (IIc), (IId), (IIe), (IIf), (IIg), (IIh) or (IIi) attached to the sulphonyl group in formula (I) via the position marked *", in which n is the number 2 or 3, o is the number 1, 2 or 3, R² is a hydrogen atom, a C₁₋₃-alkyl, cyclopropyl or a phenyl group and R³ is a hydrogen atom, a cyclopropyl group, a straight-chain or branched C₁₋₃-alkyl group, a F₃C—CH₂—, F₂CH—CH₂— or H₂FC—CH₂— group, a tautomer or a salt thereof.

4. A compound of the formula I according to claim 1 in which

R¹ is an isopropyl, cyclopropyl, phenyl, phenylmethyl, 2,4-dichlorophenylmethyl, 2-chlorophenyl, 3-chlorophenyl, 4-chlorophenyl, 2-bromophenyl, 3-bromophenyl, 4-bromophenyl, 3-fluorophenyl, 4-fluorophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,4,5-trichlorophenyl, 3,4-difluorophenyl, 2-chloro-4-fluorophenyl, 2-chloro-4-cyanophenyl, 5-fluoro-2-methylphenyl, 2-chloro-6-methylphenyl, 2-chloro-4-trifluoromethylphenyl, 3-chloro-2-methylphenyl, 4-amino-3,5-dichlorophenyl, 4-amino-2,5-dichlorophenyl, 4-chloro-2,5-dimethylphenyl, 2,4-dichloro-5-methylphenyl, 3,5-dichloro-4-hydroxyphenyl, 4-(morpholin-4-ylsulphonyl)phenyl, 4-chloro-3-nitrophenyl, 3-methylsulphonylphenyl, 4-methylsulphonylphenyl, 4-cyanophenyl, 2-nitrophenyl, 3-nitrophenyl, 4-nitrophenyl, 4-nitro-3-fluorophenyl, 4-nitro-3-trifluoromethylphenyl, 4-methoxy-2-nitrophenyl, 2-trifluoromethoxyphenyl, 2-methylphenyl, 3-methylphenyl, 4-methylphenyl, 2-trifluoromethylphenyl, 3-trifluoromethylphenyl, 4-trifluoromethylphenyl, 4-propylphenyl, 4-isopropylphenyl, 4-tert.-butylphenyl, 4-pentylphenyl, 4-(3-methoxycarbonylpropyl)phenyl, 2,4,6-trimethylphenyl, 2,5-dimethylphenyl, 3,5-dimethylphenyl, 2,3,5,6-tetramethylphenyl, 4-methoxy-2,3,6-trimethylphenyl, 4-butoxyphenyl, 4-methoxyphenyl, 4-trifluoromethoxyphenyl, 2,5-dimethoxyphenyl, 3,4-dimethoxyphenyl, 4-chloro-2-methoxyphenyl, 5-chloro-2-methoxyphenyl, 4-acetylaminophenyl, 4-acetylamino-3-chlorophenyl, 4-(3,3-dimethylureido)phenyl, 4-phenoxyphenyl, benzyl, 2-chlorobenzyl, 2,4-dichlorobenzyl, biphen-4-yl, benzo[b]thiophen-2-yl, benzo[b]thiophen-3-yl, quinolin-8-yl, isoquinolin-1-yl, isoquinolin-3-yl, naphthalen-1-yl, naphthalen-2-yl, 4-chloronaphthalen-1-yl, 5-chloronaphthalen-1-yl, 5-dimethylaminonaphthalen-1-yl, benz[1,2,5]oxadiazol-4-yl, furan-2-yl, furan-3-yl, thiophen-2-yl, thiophen-3-yl, 4,5-dichlorothiophen-2-yl, 5-chlorothiophen-2-yl, 1,2-dimethyl-1H-imidazol-4-yl, 2-methyl-1H-imidazol-4-yl, 4-bromo-5-chlorothiophen-2-yl, 3-bromo-5-chlorothiophen-2-yl, 2,4-dimethylthiazol-5-yl, 5-chloro-1,3-dimethyl-1H-pyrazol-4-yl, pyridin-2-yl, pyridin-3-yl, pyridin-4-yl, 3,5-dimethylisoxazol-4-yl or 1-methyl-1H-imidazol-4-yl group, R⁴ is a hydrogen atom or a methyl group, G is the group —(CH₂)ₘ— in which m is the number 2 or 3 or the group —(CH₂)ₘ— in which m is the number 2 or 3 and in which one or two hydrogen atoms independently of one another are replaced by methyl groups, Ar is a phenylene group which is optionally mono- or disubstituted independently of one another by fluorine, chlorine or bromine atoms, cyano, C₁₋₃-alkyl, trifluoromethyl, C₁₋₃-alkyloxy or trifluoromethoxy groups, but which is preferably unsubstituted, Q is the group —(CH₂)ₚ— in which p is the number 2 or the group —(CH₂)ₚ— in which p is the number 2 and in which one or two hydrogen atoms independently of one another are replaced by methyl groups, A is a group of the formula (IIa), (IIb), (IIc), (IId), (IIe), (IIf), (IIg), (IIh) or (IIi) attached to the sulphonyl group in formula (I) via the position marked *", and is preferably a group of the formula (IIa), (IIb), (IIc), (IIe), (IIf), (IIg), (IIh) or (IIi), in which n is the number 2 or 3, o is the number 1, 2 or 3, R² is a hydrogen atom, a methyl, ethyl, n-propyl, i-propyl, cyclopropyl or phenyl group and R³ is a hydrogen atom, a methyl, ethyl, n-propyl, i-propyl, 2-monofluoroethyl, 2,2-difluoroethyl, 2,2,2-trifluoroethyl or cyclopropyl group, where the phenyl groups mentioned above or the phenyl groups present in the groups mentioned above independently of one another may, unless indicated otherwise, be mono- or disubstituted by fluorine, chlorine or bromine atoms, cyano, C₁₋₃-alkyl, trifluoromethyl, C₁₋₃-alkyloxy or trifluoromethoxy groups, but are preferably unsubstituted, or a tautomer or a salt thereof.

5. A compound of the formula (I) according to claim 1 selected from the following group:

(1) 3-[(2,3-Dichlorobenzenesulphonyl)methylamino]-N-{2-[4-(4,5-dihydro-1H-imidazol-2-yl)phenyl]ethyl}-N-methylpropionamide, (2) 4-[(2,3-Dichlorobenzenesulphonyl)methylamino]-N-{2-[4-(4,5-dihydro-1H-imidazol-2-yl)phenyl]ethyl}-N-methylbutyramide, (3) 4-[(2,3-Dichlorobenzenesulphonyl)phenylamino]-N-{2-[4-(4,5-dihydro-1H-imidazol-2-yl)phenyl]ethyl}-N-methylbutyramide, (4) 4-[(2,3-Dichlorobenzenesulphonyl)isopropylamino]-N-{2-[4-(4,5-dihydro-1H-imidazol-2-yl)phenyl]ethyl}-N-methylbutyramide, (5) 4-[(2,3-Dichlorobenzenesulphonyl)cyclopropylamino]-N-{2-[4-(4,5-dihydro-1H-imidazol-2-yl)phenyl]ethyl}-N-methylbutyramide, (6) 2-(Benzenesulphonylmethylamino)-N-{2-[4-(4,5-dihydro-1H-imidazol-2-yl)phenyl]ethyl}-N-methylacetamide, (7) 3-(Benzenesulphonylmethylamino)-N-{2-[4-(4,5-dihydro-1H-imidazol-2-yl)phenyl]ethyl}-N-methylpropionamide, (8) 3-[1-(2,3-Dichlorobenzenesulphonyl)piperidin-2-yl]-N-{2-[4-(4,5-dihydro-1H-imidazol-2-yl)phenyl]ethyl}-N-methylpropionamide, (9) 3-[1-(4-Chloro-2,5-dimethylbenzenesulphonyl)piperidin-2-yl]-N-{2-[4-(4,5-dihydro-1H-imidazol-2-yl)phenyl]ethyl}-N-methylpropionamide,

(10) 3-(1-Benzenesulphonylpiperidin-2-yl)-N-{2-[4-(4,5-dihydro-1H-imidazol-2-yl)phenyl]ethyl}-N-methylpropionamide,

(11) 3-[1-(2,3-Dichlorobenzenesulphonyl)pyrrolidin-2(S)-yl]-N-{2-[4-(4,5-dihydro-1H-imidazol-2-yl)phenyl]ethyl}-N-methylpropionamide,

(12) 1-(2,3-Dichlorobenzenesulphonyl)piperidin-3-yl-N-{2-[4-(4,5-dihydro-1H-imidazol-2-yl)phenyl]ethyl}-N-methylcarboxamide,

(13) N-{3-[(2,3-Dichlorobenzenesulphonyl)methylamino]propyl}-3-[4-(4,5-dihydro-1H-imidazol-2-yl)phenyl]propionamide,

(14) N-{3-[(2,3-Dichlorobenzenesulphonyl)methylamino]propyl}-3-[4-(4,5-dihydro-1H-imidazol-2-yl)phenyl]-N-methylpropionamide,

(15) 3-[4-(4,5-Dihydro-1H-imidazol-2-yl)phenyl]-N-methyl-N-{3-[phenyl(toluene-4-sulphonyl)amino]propyl}propionamide,

(16) N-{2-[(4-Chloro-2,5-dimethylbenzenesulphonyl)methylamino]ethyl}-3-[4-(4,5-dihydro-1H-imidazol-2-yl)phenyl]propionamide,

(17) 2,3-Dichloro-N-[2-(3-{2-[4-(4,5-dihydro-1H-imidazol-2-yl)phenyl]ethyl}-2-oxoimidazolidin-1-yl)ethyl]-N-methylbenzenesulphonamide,

(18) 2,3-Dichloro-N-[2-(3-{2-[4-(4,5-dihydro-1H-imidazol-2-yl)phenyl]ethyl}-2-oxotetrahydropyrimidin-1-yl)ethyl]-N-methylbenzenesulphonamide,

(19) 4-[(2,3-Dichlorobenzenesulphonyl)methylamino]-N-methyl-N-{2-[4-(1-methyl-4,5-dihydro-1H-imidazol-2-yl)phenyl]ethyl}butyramide,

(20) 3-[(2,3-Dichlorobenzenesulphonyl)methylamino]cyclohexane-N-{2-[4-(4,5-dihydro-1H-imidazol-2-yl)phenyl]ethyl}-N-methyl-carboxamide,

(21) 3-[(2,3-Dichlorobenzenesulphonyl)methylamino]cyclopentane-N-{2-[4-(4,5-dihydro-1H-imidazol-2-yl)phenyl]ethyl}-N-methylcarboxamide,

(22) 4-[(2,3-Dichlorobenzenesulphonyl)methylamino]-N-{2-[4-(4,5-dihydro-1H-imidazol-2-yl)phenyl]ethyl}-N-ethylbutyramide,

(23) N-Cyclopropyl-4-[(2,3-dichlorobenzenesulphonyl)methylamino]-N-{2-[4-(4,5-dihydro-1H-imidazol-2-yl)phenyl]ethyl}butyramide,

(24) 4-[(2,3-Dichlorobenzenesulphonyl)methylamino]-N-{2-[4-(4,5-dihydro-1H-imidazol-2-yl)phenyl]ethyl}butyramide,

(25) 3-[(2,5-Dichlorobenzenesulphonyl)methylamino]-N-{2-[4-(4,5-dihydro-1H-imidazol-2-yl)phenyl]ethyl}-N-methylpropionamide,

(26) 3-[(Benzo[b]thiophene-2-sulphonyl)methylamino]-N-{2-[4-(4,5-dihydro-1H-imidazol-2-yl)phenyl]ethyl}-N-methylpropionamide,

(27) 3-[(2-Chlorobenzenesulphonyl)methylamino]-N-{2-[4-(4,5-dihydro-1H-imidazol-2-yl)phenyl]ethyl}-N-methylpropionamide,

(28) 2-[1-(2,3-Dichlorobenzenesulphonyl)pyrrolidin-2-yl]-N-{2-[4-(4,5-dihydro-1H-imidazol-2-yl)phenyl]ethyl}-N-methylacetamide,

(29) N-{2-[4-(4,5-Dihydro-1H-imidazol-2-yl)phenyl]ethyl}-N-methyl-3-[methyl-(2,4,6-trimethylbenzenesulphonyl)amino]propionamide,

(30) 3-[(2-Chloro-6-methylbenzenesulphonyl)methylamino]-N-{2-[4-(4,5-dihydro-1H-imidazol-2-yl)phenyl]ethyl}-N-methylpropionamide,

(31) N-{2-[4-(4,5-Dihydro-1H-imidazol-2-yl)phenyl]ethyl}-N-methyl-3-[methyl(quinoline-8-sulphonyl)amino]propionamide,

(32) 3-[4-(4,5-Dihydro-1H-imidazol-2-yl)phenyl]-N-methyl-N-{2-[methyl-(2,4,6-trimethylbenzenesulphonyl)amino]ethyl}propionamide,

(33) N-{2-[4-(4,5-Dihydro-1H-imidazol-2-yl)phenyl]ethyl}-3-[(4-trifluoro-methoxybenzenesulphonyl)methylamino]-N-methylpropionamide,

(34) N-{2-[(4-Chloro-2,5-dimethylbenzenesulphonyl)methylamino]ethyl}-3-[4-(4,5-dihydro-1H-imidazol-2-yl)phenyl]-N-methylpropionamide,

(35) 3-[(5-Chloro-2-methoxybenzenesulphonyl)methylamino]-N-{2-[4-(4,5-dihydro-1H-imidazol-2-yl)phenyl]ethyl}-N-methylpropionamide,

(36) N-{2-[(2,3-Dichlorobenzenesulphonyl)methylamino]ethyl}-3-[4-(4,5-dihydro-1H-imidazol-2-yl)phenyl]-N-methylpropionamide,

(37) 3-(Cyclopropanesulphonylmethylamino)-N-{2-[4-(4,5-dihydro-1H-imidazol-2-yl)phenyl]ethyl}-N-methylpropionamide,

(38) 1-[4-(2,3-Dichlorobenzenesulphonyl)-[1,4]diazepan-1-yl]-3-[4-(4,5-dihydro-1H-imidazol-2-yl)phenyl]propan-1-one,

(39) 1-[4-(2,3-Dichlorobenzenesulphonyl)piperazin-1-yl]-3-[4-(4,5-dihydro-1H-imidazol-2-yl)phenyl]propan-1-one,

(40) 2-[(2,3-Dichlorobenzenesulphonyl)methylamino]-N-{2-[4-(4,5-dihydro-1H-imidazol-2-yl)phenyl]ethyl}-N-methylacetamide,

(41) 3-[(3,5-Dichlorobenzenesulphonyl)methylamino]-N-[2-[4-(4,5-dihydro-1H-imidazol-2-yl)phenyl]ethyl}-N-methylpropionamide,

(42) 3-(Benzenesulphonylmethylamino)-N-{2-[4-(4,5-dihydro-1H-imidazol-2-yl)phenyl]ethyl}-N-methylpropionamide,

(43) N-{2-[4-(4,5-Dihydro-1H-imidazol-2-yl)phenyl]ethyl}-N-methyl-3-[methyl-(4-propylbenzenesulphonyl)amino]propionamide,

(44) 3-[(4-Chloro-3-nitrobenzenesulphonyl)methylamino]-N-{2-[4-(4,5-dihydro-1H-imidazol-2-yl)phenyl]ethyl}-N-methylpropionamide,

(45) 3-[(2-Chloro-6-methylbenzenesulphonyl)methylamino]-N-{2-[4-(4,5-dihydro-1H-imidazol-2-yl)phenyl]ethyl}-N-methylpropionamide,

(46) N-{2-[4-(4,5-Dihydro-1H-imidazol-2-yl)phenyl]ethyl}-3-[(4-isopropyl-benzenesulphonyl)methylamino]-N-methylpropionamide,

(47) 3-[(5-Chloronaphthalene-1-sulphonyl)methylamino]-N-{2-[4-(4,5-dihydro-1H-imidazol-2-yl)phenyl]ethyl}-N-methylpropionamide,

(48) N-{2-[4-(4,5-Dihydro-1H-imidazol-2-yl)phenyl]ethyl}-N-methyl-3-[methyl(toluene-4-sulphonyl)amino]propionamide,

(49) 3-[(2-Bromobenzenesulphonyl)methylamino]-N-{2-[4-(4,5-dihydro-1H-imidazol-2-yl)phenyl]ethyl}-N-methylpropionamide,

(50) 3-[(2,4-Dichloro-5-methylbenzenesulphonyl)methylamino]-N-{2-[4-(4,5-dihydro-1H-imidazol-2-yl)phenyl]ethyl}-N-methylpropionamide,

(51) N-{2-[4-(4,5-Dihydro-1H-imidazol-2-yl)phenyl]ethyl}-N-methyl-3-{methyl-[4-(morpholine-4-sulphonyl)benzenesulphonyl]amino}propionamide,

(52) N-{2-[4-(4,5-Dihydro-1H-imidazol-2-yl)phenyl]ethyl}-N-methyl-3-[methyl-(3-nitrobenzenesulphonyl)amino]propionamide,

(53) N-{2-[4-(4,5-Dihydro-1H-imidazol-2-yl)phenyl]ethyl}-N-methyl-3-[methyl-(2-trifluoromethoxybenzenesulphonyl)amino]propionamide,

(54) 3-[(Benz[1,2,5]oxadiazole-4-sulphonyl)methylamino]-N-{2-[4-(4,5-dihydro-1H-imidazol-2-yl)phenyl]ethyl}-N-methylpropionamide,

(55) 3-[(2-Chloro-4-trifluoromethylbenzenesulphonyl)methylamino]-N-{2-[4-(4,5-dihydro-1H-imidazol-2-yl)phenyl]ethyl}-N-methylpropionamide,

(56) 3-[(4-Butoxybenzenesulphonyl)methylamino]-N-{2-[4-(4,5-dihydro-1H-imidazol-2-yl)phenyl]ethyl}-N-methylpropionamide,

(57) 3-[(3,4-Difluorobenzenesulphonyl)methylamino]-N-{2-[4-(4,5-dihydro-1H-imidazol-2-yl)phenyl]ethyl}-N-methylpropionamide,

(58) 3-[(3,5-Dichloro-4-hydroxybenzenesulphonyl)methylamino]-N-{2-[4-(4,5-dihydro-1H-imidazol-2-yl)phenyl]ethyl}-N-methylpropionamide,
(59) N-{2-[4-(4,5-Dihydro-1H-imidazol-2-yl)phenyl]ethyl}-N-methyl-3-[methyl(naphthalene-1-sulphonyl)amino]propionamide,
(60) 3-[(2,4-Dichlorobenzenesulphonyl)methylamino]-N-{2-[4-(4,5-dihydro-1H-imidazol-2-yl)phenyl]ethyl}-N-methylpropionamide,
(61) N-{2-[4-(4,5-Dihydro-1H-imidazol-2-yl)phenyl]ethyl}-N-methyl-3-[methyl-(4-pentylbenzenesulphonyl)amino]propionamide,
(62) N-{2-[4-(4,5-Dihydro-1H-imidazol-2-yl)phenyl]ethyl}-3-[(3,5-dimethyl-benzenesulphonyl)methylamino]-N-methylpropionamide,
(63) N-{2-[4-(4,5-Dihydro-1H-imidazol-2-yl)phenyl]ethyl}-N-methyl-3-(methylphenylmethanesulphonylamino)propionamide,
(64) 3-[(2-Chloro-4-fluorobenzenesulphonyl)methylamino]-N-{2-[4-(4,5-dihydro-1H-imidazol-2-yl)phenyl]ethyl}-N-methylpropionamide,
(65) 3-[(2-Chloro-4-cyanobenzenesulphonyl)methylamino]-N-{2-[4-(4,5-dihydro-1H-imidazol-2-yl)phenyl]ethyl}-N-methylpropionamide,
(66) N-{2-[4-(4,5-Dihydro-1H-imidazol-2-yl)phenyl]ethyl}-3-[(3-methane-sulphonylbenzenesulphonyl)methylamino]-N-methylpropionamide,
(67) 3-[(Biphenyl-4-sulphonyl)methylamino]-N-{2-[4-(4,5-dihydro-1H-imidazol-2-yl)phenyl]ethyl}-N-methylpropionamide,
(68) N-{2-[4-(4,5-Dihydro-1H-imidazol-2-yl)phenyl]ethyl}-3-[(5-fluoro-2-methylbenzenesulphonyl)methylamino]-N-methylpropionamide,
(69) N-{2-[4-(4,5-Dihydro-1H-imidazol-2-yl)phenyl]ethyl}-N-methyl-3-[methyl-(4-nitrobenzenesulphonyl)amino]propionamide,
(70) N-{2-[4-(4,5-Dihydro-1H-imidazol-2-yl)phenyl]ethyl}-3-{[4-(3,3-dimethylureido)benzenesulphonyl]methylamino}-N-methylpropionamide,
(71) N-{2-[4-(4,5-Dihydro-1H-imidazol-2-yl)phenyl]ethyl}-N-methyl-3-[methyl-(4-trifluoromethylbenzenesulphonyl)amino]propionamide,
(72) N-{2-[4-(4,5-Dihydro-1H-imidazol-2-yl)phenyl]ethyl}-3-[(furan-2-sulphonyl)methylamino]-N-methylpropionamide,
(73) 3-[(2-Chlorophenylmethanesulphonyl)methylamino]-N-{2-[4-(4,5-dihydro-1H-imidazol-2-yl)phenyl]ethyl}-N-methylpropionamide,
(74) 3-[(2,6-Dichlorobenzenesulphonyl)methylamino]-N-{2-[4-(4,5-dihydro-1H-imidazol-2-yl)phenyl]ethyl}-N-methylpropionamide,
(75) N-{2-[4-(4,5-Dihydro-1H-imidazol-2-yl)phenyl]ethyl}-3-[(4-methoxy-2-nitrobenzenesulphonyl)methylamino]-N-methylpropionamide,
(76) N-{2-[4-(4,5-Dihydro-1H-imidazol-2-yl)phenyl]ethyl}-N-methyl-3-[methyl(thiophene-3-sulphonyl)amino]propionamide,
(77) 3-[(Benzo[b]thiophene-3-sulphonyl)methylamino]-N-{2-[4-(4,5-dihydro-1H-imidazol-2-yl)phenyl]ethyl}-N-methylpropionamide,
(78) N-{2-[4-(4,5-Dihydro-1H-imidazol-2-yl)phenyl]ethyl}-3-[(5-dimethyl-aminonaphthalene-1-sulphonyl)methylamino]-N-methylpropionamide,
(79) N-{2-[4-(4,5-Dihydro-1H-imidazol-2-yl)phenyl]ethyl}-N-methyl-3-[methyl(toluene-2-sulphonyl)amino]propionamide,
(80) N-{2-[4-(4,5-Dihydro-1H-imidazol-2-yl)phenyl]ethyl}-N-methyl-3-[methyl-(4-phenoxybenzenesulphonyl)amino]propionamide,
(81) 3-[(2,4-Dichlorophenylmethanesulphonyl)methylamino]-N-{2-[4-(4,5-dihydro-1H-imidazol-2-yl)phenyl]ethyl}-N-methylpropionamide,
(82) N-{2-[4-(4,5-Dihydro-1H-imidazol-2-yl)phenyl]ethyl}-3-[(4-methoxy-2,3,6-trimethylbenzenesulphonyl)methylamino]-N-methylpropionamide,
(83) N-{2-[4-(4,5-Dihydro-1H-imidazol-2-yl)phenyl]ethyl}-N-methyl-3-[methyl-(4-nitro-3-trifluoromethylbenzenesulphonyl)amino]propionamide,
(84) 4-[(5-Chlorothiophene-2-sulphonyl)methylamino]-N-{2-[4-(4,5-dihydro-1H-imidazol-2-yl)phenyl]ethyl}-N-methylbutyramide,
(85) 4-[(2-Chlorobenzenesulphonyl)methylamino]-N-{2-[4-(4,5-dihydro-1H-imidazol-2-yl)phenyl]ethyl}-N-methylbutyramide,
(86) N-{2-[4-(4,5-Dihydro-1H-imidazol-2-yl)phenyl]ethyl}-4-[(2,5-dimethyl-benzenesulphonyl)methylamino]-N-methylbutyramide,
(87) N-{2-[4-(4,5-Dihydro-1H-imidazol-2-yl)phenyl]ethyl}-4-[(1,2-dimethyl-1H-imidazole-4-sulphonyl)methylamino]-N-methylbutyramide,
(88) N-{2-[4-(4,5-Dihydro-1H-imidazol-2-yl)phenyl]ethyl}-4-[(4-methane-sulphonylbenzenesulphonyl)methylamino]-N-methylbutyramide,
(89) 4-[(3-Bromobenzenesulphonyl)methylamino]-N-{2-[4-(4,5-dihydro-1H-imidazol-2-yl)phenyl]ethyl}-N-methylbutyramide,
(90) 4-[(4-Bromo-5-chlorothiophene-2-sulphonyl)methylamino]-N-{2-[4-(4,5-dihydro-1H-imidazol-2-yl)phenyl]ethyl}-N-methylbutyramide,
(91) 4-[(3-Bromo-5-chlorothiophene-2-sulphonyl)methylamino]-N-{2-[4-(4,5-dihydro-1H-imidazol-2-yl)phenyl]ethyl}-N-methylbutyramide,
(92) 4-[(4,5-Dichlorothiophene-2-sulphonyl)methylamino]-N-{2-[4-(4,5-dihydro-1H-imidazol-2-yl)phenyl]ethyl}-N-methylbutyramide,
(93) N-{2-[4-(4,5-Dihydro-1H-imidazol-2-yl)phenyl]ethyl}-4-[(2,4-dimethylthiazole-5-sulphonyl)methylamino]-N-methylbutyramide,
(94) 4-[(5-Chloro-1,3-dimethyl-1H-pyrazole-4-sulphonyl)methylamino]-N-{2-[4-(4,5-dihydro-1H-imidazol-2-yl)phenyl]ethyl}-N-methylbutyramide,
(95) 4-[(4-Amino-3,5-dichlorobenzenesulphonyl)methylamino]-N-{2-[4-(4,5-dihydro-1H-imidazol-2-yl)phenyl]ethyl}-N-methylbutyramide,
(96) N-{2-[4-(4,5-Dihydro-1H-imidazol-2-yl)phenyl]ethyl}-N-methyl-4-[methyl-(2,4,5-trichlorobenzenesulphonyl)amino]butyramide,
(97) 4-[(2,5-Dichlorobenzenesulphonyl)methylamino]-N-{2-[4-(4,5-dihydro-1H-imidazol-2-yl)phenyl]ethyl}-N-methylbutyramide,
(98) 4-[(3,4-Dichlorobenzenesulphonyl)methylamino]-N-{2-[4-(4,5-dihydro-1H-imidazol-2-yl)phenyl]ethyl}-N-methylbutyramide,
(99) 4-[(4-Bromobenzenesulphonyl)methylamino]-N-{2-[4-(4,5-dihydro-1H-imidazol-2-yl)phenyl]ethyl}-N-methylbutyramide,
(100) 4-[(4-Fluorobenzenesulphonyl)methylamino]-N-{2-[4-(4,5-dihydro-1H-imidazol-2-yl)phenyl]ethyl}-N-methylbutyramide,
(101) 4-[(3-Fluorobenzenesulphonyl)methylamino]-N-{2-[4-(4,5-dihydro-1H-imidazol-2-yl)phenyl]ethyl}-N-methylbutyramide, (102) 4-[(4-Chlorobenzenesulphonyl)methylamino]-N-{2-[4-(4,5-dihydro-1H-imidazol-2-yl)phenyl]ethyl}-N-methylbutyramide,
(103) N-{2-[4-(4,5-Dihydro-1H-imidazol-2-yl)phenyl]ethyl}-N-methyl-4-[methyl-(2-trifluoromethylbenzenesulphonyl)amino]butyramide,
(104) 4-[(5-Chloro-2-methoxybenzenesulphonyl)methylamino]-N-{2-[4-(4,5-dihydro-1H-imidazol-2-yl)phenyl]ethyl}-N-methylbutyramide,
(105) N-{2-[4-(4,5-Dihydro-1H-imidazol-2-yl)phenyl]ethyl}-N-methyl-4-[methyl(toluene-3-sulphonyl)amino]butyramide,
(106) N-{2-[4-(4,5-Dihydro-1H-imidazol-2-yl)phenyl]ethyl}-4-[(4-methoxy-benzenesulphonyl)methylamino]-N-methylbutyramide,
(107) 4-[(4-Acetylamino-3-chlorobenzenesulphonyl)methylamino]-N-{2-[4-(4,5-dihydro-1H-imidazol-2-yl)phenyl]ethyl}-N-methylbutyramide,
(108) N-{2-[4-(4,5-Dihydro-1H-imidazol-2-yl)phenyl]ethyl}-4-[(2,5-dimethoxybenzenesulphonyl)methylamino]-N-methylbutyramide,
(109) N-{2-[4-(4,5-Dihydro-1H-imidazol-2-yl)phenyl]ethyl}-4-[(3,4-dimethoxybenzenesulphonyl)methylamino]-N-methylbutyramide,
(110) N-{2-[4-(4,5-Dihydro-1H-imidazol-2-yl)phenyl]ethyl}-N-methyl-4-[methyl-(2,4,6-trimethylbenzenesulphonyl)amino]butyramide,
(111) N-{2-[4-(4,5-Dihydro-1H-imidazol-2-yl)phenyl]ethyl}-N-methyl-4-[methyl(naphthalene-2-sulphonyl)amino]butyramide,
(112) N-{2-[4-(4,5-Dihydro-1H-imidazol-2-yl)phenyl]ethyl}-N-methyl-4-[methyl-(2,3,5,6tetramethylbenzenesulphonyl)amino]butyramide,
(113) N-{2-[4-(4,5-Dihydro-1H-imidazol-2-yl)phenyl]ethyl}-N-methyl-4-[methyl-(2-nitromethylbenzenesulphonyl)amino]butyramide,
(114) 4-[(4-Cyanobenzenesulphonyl)methylamino]-N-{2-[4-(4,5-dihydro-1H-imidazol-2-yl)phenyl]ethyl}-N-methylbutyramide,
(115) 4-[(4-Amino-2,5-dichlorobenzenesulphonyl)methylamino]-N-{2-[4-(4,5-dihydro-1H-imidazol-2-yl)phenyl]ethyl}-N-methylbutyramide,
(116) 4-[(4-tert.-Butylbenzenesulphonyl)methylamino]-N-{2-[4-(4,5-dihydro-1H-imidazol-2-yl)phenyl]ethyl}-N-methylbutyramide,
(117) 4-[(4-Butoxybenzenesulphonyl)methylamino]-N-{2-[4-(4,5-dihydro-1H-imidazol-2-yl)phenyl]ethyl}-N-methylbutyramide,
(118) 4-[(2,4-Dichlorobenzenesulphonyl)methylamino]-N-{2-[4-(4,5-dihydro-1H-imidazol-2-yl)phenyl]ethyl}-N-methylbutyramide,
(119) 4-[(2-Chloro-4-fluorobenzenesulphonyl)methylamino]-N-{2-[4-(4,5-dihydro-1H-imidazol-2-yl)phenyl]ethyl}-N-methylbutyramide,
(120) N-{2-[4-(4,5-Dihydro-1H-imidazol-2-yl)phenyl]ethyl}-4-[(5-fluoro-2-methylbenzenesulphonyl)methylamino]-N-methylbutyramide,
(121) N-{2-[4-(4,5-Dihydro-1H-imidazol-2-yl)phenyl]ethyl}-4-[(4-methoxy-2-nitrobenzenesulphonyl)methylamino]-N-methylbutyramide,
(122) N-{2-[4-(4,5-Dihydro-1H-imidazol-2-yl)phenyl]ethyl}-N-methyl-4-[methyl(toluene-2-sulphonyl)amino]butyramide,
(123) N-{2-[4-(4,5-Dihydro-1H-imidazol-2-yl)phenyl]ethyl}-4-[(4-methoxy-2,3,6-trimethylbenzenesulphonyl)methylamino]-N-methylbutyramide,
(124) N-{2-[4-(4,5-Dihydro-1H-imidazol-2-yl)phenyl]ethyl}-N-methyl-4-[methyl-(4-propylbenzenesulphonyl)amino]butyramide,
(125) 4-[(2,4-Dichloro-5-methylbenzenesulphonyl)methylamino]-N-{2-[4-(4,5-dihydro-1H-imidazol-2-yl)phenyl]ethyl}-N-methylbutyramide,
(126) 4-[(3,4-Difluorobenzenesulphonyl)methylamino]-N-{2-[4-(4,5-dihydro-1H-imidazol-2-yl)phenyl]ethyl}-N-methylbutyramide,
(127) N-{2-[4-(4,5-Dihydro-1H-imidazol-2-yl)phenyl]ethyl}-N-methyl-4-[methyl-(4-pentylbenzenesulphonyl)amino]butyramide,
(128) 4-[(2-Chloro-4-cyanobenzenesulphonyl)methylamino]-N-{2-[4-(4,5-dihydro-1H-imidazol-2-yl)phenyl]ethyl}-N-methylbutyramide,
(129) N-{2-[4-(4,5-Dihydro-1H-imidazol-2-yl)phenyl]ethyl}-N-methyl-4-[methyl-(4-nitromethylbenzenesulphonyl)amino]butyramide,
(130) N-{2-[4-(4,5-Dihydro-1H-imidazol-2-yl)phenyl]ethyl}-4-[(furan-2-sulphonyl)methylamino]-N-methylbutyramide,
(131) N-{2-[4-(4,5-Dihydro-1H-imidazol-2-yl)phenyl]ethyl}4-[(furan-3-sulphonyl)methylamino]-N-methylbutyramide,
(132) N-{2-[4-(4,5-Dihydro-1H-imidazol-2-yl)phenyl]ethyl}-4-[(thiophene-3-sulphonyl)methylamino]-N-methylbutyramide,
(133) N-{2-[4-(4,5-Dihydro-1H-imidazol-2-yl)phenyl]ethyl}-N-methyl-4-[methyl-(4-phenoxybenzenesulphonyl)amino]butyramide,
(134) 4-[(5-Chloronaphthalene-1-sulphonyl)methylamino]-N-{2-[4-(4,5-dihydro-1H-imidazol-2-yl)phenyl]ethyl}-N-methylbutyramide,
(135) N-{2-[4-(4,5-Dihydro-1H-imidazol-2-yl)phenyl]ethyl}-N-methyl-4-{methyl-[4-(morpholine-4-sulphonyl)benzenesulphonyl]amino}butyramide,
(136) 4-[(2-Chloro-4-trifluoromethylbenzenesulphonyl)methylamino]-N-{2-[4-(4,5-dihydro-1H-imidazol-2-yl)phenyl]ethyl}-N-methylbutyramide,
(137) 4-[(3,5-Dichloro-4-hydroxybenzenesulphonyl)methylamino]-N-{2-[4-(4,5-dihydro-1H-imidazol-2-yl)phenyl]ethyl}-N-methylbutyramide,
(138) N-{2-[4-(4,5-Dihydro-1H-imidazol-2-yl)phenyl]ethyl}-N-methyl-4-[methyl-(3,5-dimethylbenzenesulphonyl)amino]butyramide,
(139) N-{2-[4-(4,5-Dihydro-1H-imidazol-2-yl)phenyl]ethyl}-4-[(3-methane-sulphonylbenzenesulphonyl)methylamino]-N-methylbutyramide,
(140) N-{2-[4-(4,5-Dihydro-1H-imidazol-2-yl)phenyl]ethyl}-4-{[4-(3,3-dimethylurea)benzenesulphonyl]methylamino}-N-methylbutyramide,
(141) 4-[(Benzo[b]thiophene-3-sulphonyl)methylamino]-N-{2-[4-(4,5-dihydro-1H-imidazol-2-yl)phenyl]ethyl}-N-methylbutyramide,
(142) N-{2-[4-(4,5-Dihydro-1H-imidazol-2-yl)phenyl]ethyl}-N-methyl-4-[methyl-(4-nitro-3-trifluoromethylbenzenesulphonyl)amino]butyramide,
(143) 4-[(4-Chloro-3-nitrobenzenesulphonyl)methylamino]-N-{2-[4-(4,5-dihydro-1H-imidazol-2-yl)phenyl]ethyl}-N-methylbutyramide,
(144) N-{2-[4-(4,5-Dihydro-1H-imidazol-2-yl)phenyl]ethyl}-N-methyl-4-[methyl(toluene-4-sulphonyl)amino]butyramide,
(145) 4-[(4-Acetylaminobenzenesulphonyl)methylamino]-N-{2-[4-(4,5-dihydro-1H-imidazol-2-yl)phenyl]ethyl}-N-methylbutyramide, (146) N-{2-[4-(4,5-Dihydro-1H-imidazol-2-yl)phenyl]ethyl}-N-methyl-4-[methyl-(3-nitromethylbenzenesulphonyl)amino]butyramide,
(147) 4-(Benzenesulphonylmethylamino)-N-{2-[4-(4,5-dihydro-1H-imidazol-2-yl)phenyl]ethyl}-N-methylbutyramide,
(148) N-{2-[4-(4,5-Dihydro-1H-imidazol-2-yl)phenyl]ethyl}-N-methyl-4-[methyl([naphthalene-1-sulphonyl)amino]butyramide,
(149) 4-(Biphenyl-4-sulphonylmethylamino)-N-{2-[4-(4,5-dihydro-1H-imidazol-2-yl)phenyl]ethyl}-N-methylbutyramide,
(150) N-{2-[4-(4,5-Dihydro-1H-imidazol-2-yl)phenyl]ethyl}-N-methyl-4-[methyl-(4trifluoromethylbenzenesulphonyl)amino]butyramide,
(151) 4-[(2,6-Dichlorobenzenesulphonyl)methylamino]-N-{2-[4-(4,5-dihydro-1H-imidazol-2-yl)phenyl]ethyl}-N-methylbutyramide,
(152) N-{2-[4-(4,5-Dihydro-1H-imidazol-2-yl)phenyl]ethyl}4-[(5-dimethyl-aminonaphthalene-1-sulphonyl)methylamino]-N-methylbutyramide,
(153) N-{2-[4-(4,5-Dihydro-1H-imidazol-2-yl)phenyl]ethyl}-4-[(thiophene-2-sulphonyl)methylamino]-N-methylbutyramide,
(154) Methyl 3-(4-{[3-({2-[4-(4,5-dihydro-1H-imidazol-2-yl)phenyl]ethyl-methyl-carbamoyl)propyl]methylsulphamoyl}phenyl)propionate,
(155) N-{2-[4-(4,5-Dihydro-1H-imidazol-2-yl)phenyl]ethyl}-N-methyl-4-[methyl(pyridine-2-sulphonyl)amino]butyramide,
(156) 4-[(3-Chloro-2-methylbenzenesulphonyl)methylamino]-N-{2-[4-(4,5-dihydro-1H-imidazol-2-yl)phenyl]ethyl}-N-methylbutyramide,
(157) 4-[(3-Chlorobenzenesulphonyl)methylamino]-N-{2-[4-(4,5-dihydro-1H-imidazol-2-yl)phenyl]ethyl}-N-methylbutyramide,
(158) N-{2-[4-(4,5-Dihydro-1H-imidazol-2-yl)phenyl]ethyl}-N-methyl-4-[methyl-(3-trifluoromethylbenzenesulphonyl)amino]butyramide,
(159) N-{2-[4-(4,5-Dihydro-1H-imidazol-2-yl)phenyl]ethyl}-4-[(3,5-dimethylisoxazole-4-sulphonyl)methylamino]-N-methylbutyramide,
(160) N-{2-[4-(4,5-Dihydro-1H-imidazol-2-yl)phenyl]ethyl}-N-methyl-4-[methyl-(1-methyl-1H-imidazole-4-sulphonyl)amino]butyramide,
(161) 4-[(2,3-Dichlorobenzenesulphonyl)methylamino]-N-{2-[4-(4,5-dihydro-1H-imidazol-2-yl)phenyl]ethyl}-N-propylbutyramide,
(162) 4-[(2,3-Dichlorobenzenesulphonyl)methylamino]-N-{2-[4-(4,5-dihydro-1H-imidazol-2-yl)phenyl]ethyl}-N-isopropylbutyramide,
(163) 4-[(2,3-Dichlorobenzenesulphonyl)methylamino]-N-{2-[4-(4,5-dihydro-1H-imidazol-2-yl)phenyl]ethyl}-N-(2,2,2-trifluoroethyl)butyramide,
(164) 4-[(2,3-Dichlorobenzenesulphonyl)methylamino]-N-{2-[4-(4,5-dihydro-1H-imidazol-2-yl)phenyl]ethyl}-N-(2-fluoroethyl)butyramide,
(165) 4-[(2,3-Dichlorobenzenesulphonyl)methylamino]-N-(2,2-difluoroethyl)-N-{2-[4-(4,5-dihydro-1H-imidazol-2-yl)phenyl]ethyl}butyramide, and
(166) 4-[(2,3-Dichlorobenzenesulphonyl)methylamino]-N-{2-[4-(4,5-dihydro-1H-imidazol-2-yl)phenyl]ethyl}-N-phenylbutyramide, or a tautomer or salt thereof.

6. A physiologically acceptable salt of a compound according to claim 1, 2, 3, 4 or 5 with an inorganic or organic acid or base.

7. A pharmaceutical composition which comprises a compound according to claim 1, 2, 3, 4 or 5 or a physiologically acceptable salt thereof and additionally one or more inert carriers and/or diluents.

8. A method for treating pain, a neurotic skin disease, irritable bladder, irritable colon, asthma, chronic obstructive lung disease, irritations of the skin, and stomach inflammation, which method comprises administering to a host suffering from the same a therapeutically effective amount of a compound according to claim 1, 2, 3, 4 or 5 or a physiologically acceptable salt thereof.

* * * * *